(12) United States Patent
Bresnick et al.

(10) Patent No.: US 9,512,430 B2
(45) Date of Patent: Dec. 6, 2016

(54) COMPOSITIONS AND METHODS TO PROMOTE ERYTHROPOIESIS

(71) Applicant: WISCONSIN ALUMNI RESEARCH FOUNDATION, Madison, WI (US)

(72) Inventors: Emery H. Bresnick, Middleton, WI (US); Yoon A. Kang, San Francisco, CA (US); Skye McIver, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 21 days.

(21) Appl. No.: 14/323,175

(22) Filed: Jul. 3, 2014

(65) Prior Publication Data

US 2015/0011606 A1  Jan. 8, 2015

Related U.S. Application Data

(60) Provisional application No. 61/842,569, filed on Jul. 3, 2013.

(51) Int. Cl.
| | | |
|---|---|---|
| *C07H 21/02* | (2006.01) | |
| *C07H 21/04* | (2006.01) | |
| *A61K 48/00* | (2006.01) | |
| *C12N 15/11* | (2006.01) | |
| *C12N 15/113* | (2010.01) | |

(52) U.S. Cl.
CPC ......... *C12N 15/1137* (2013.01); *C12N 15/113* (2013.01); *C12Y 301/13* (2013.01); *C12N 2310/11* (2013.01); *C12N 2310/12* (2013.01); *C12N 2310/14* (2013.01); *C12N 2310/15* (2013.01); *C12N 2320/30* (2013.01)

(58) Field of Classification Search
USPC ............................................ 514/44; 536/24.5
See application file for complete search history.

(56) References Cited

U.S. PATENT DOCUMENTS

2005/0255487 A1    11/2005   Khvorova et al.

FOREIGN PATENT DOCUMENTS

| WO | 8804300 A1 | 6/1988 |
| WO | 2004045543 A2 | 6/2004 |

OTHER PUBLICATIONS

McIver et al. (Blood, 2014 vol. 124(14):2285-2297).*
Kang et al.; "Autophagy Driven by a Master Regulator of Hematopoiesis"; Mol. Cell. Biol. 32(1); pp. 226-239; (2011).
Tomecki et al.; "The Human Core Exosome Interacts with Differentially Localized Processive RNases: hDIS3 and hDIS3L"; The EMBO Journal; 29; pp. 2342-2357; (2010).
Wasmuth et al.; "Structure of an Rrp6-RNA Exosome Complex Bound to Poly(A) RNA"; Nature; Jul. 6; pp. 1-17; (2014); doi:10.1038/nature13406, epub ahead of print.

* cited by examiner

*Primary Examiner* — Terra C Gibbs
(74) *Attorney, Agent, or Firm* — Cantor Colburn LLP

(57) ABSTRACT

Described herein are compositions and methods for enhancing erythropoiesis in an individual in need thereof. Specifically agents that decrease the expression of Exosc8, Exosc9, Dis3, Dis3L or Exosc10, such as inhibitory nucleic acid molecules, produce an increase in red blood cell production in the individual.

10 Claims, 19 Drawing Sheets

Figure 37

| Gene | Function |
|---|---|
| Cdkn1b/ p27kip1 | Controls cyclin dependant kinase levels/ activity causing G1 arrest |
| Ddit3/CHOP | DNA damage inducible, inhibits G1/S transition |
| Gas2l1/ Gar22 | Lengthens cell cycle, downregulates Gata2 and c-kit in erythroid cells |
| Trp53inp1 | Acts downstream of p53 to induce G1 arrest and apoptosis |
| Gadd45a | Inhibits CDK1/CyclinB1 kinase activity to cause cell cycle arrest at G2/M checkpoint |
| Ern1 | Component of the unfolded protein response, which induces chaperone expression, decreased protein synthesis, and G1 arrest |

Figure 38

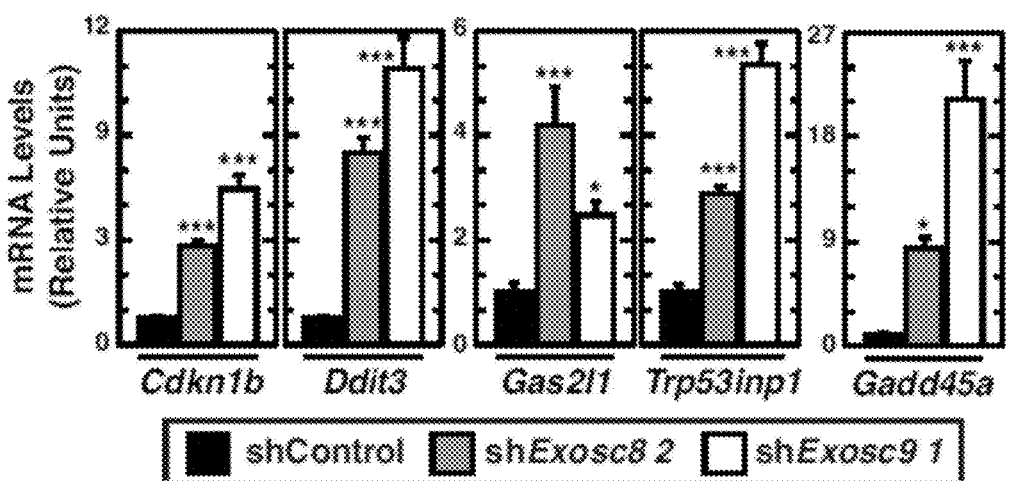

US 9,512,430 B2

SEQUENCE LISTING

<160> NUMBER OF SEQ ID NOS: 32

<210> SEQ ID NO 1
<211> LENGTH: 1427
<212> TYPE: DNA
<213> ORGANISM: Homo sapiens

<400> SEQUENCE: 1

```
agtcacagca ccagctcttt tataaagagg gagacccgct ccttctttaa cagcagattc      60
gtcaaaatac gtccaaggca aggaaaccta gaaaggcgtc tgggcagggg aaagtcgatg     120
cgagggcggg ccagggacct ttcgtcgcgt ccccaccttg gcatttcccg tggcgtgagc     180
ggccccggca tccgtgtcga aagtgcggcg gcggaacagg cgcgcaggag aggagcggcg     240
caggcgcaga cgcgcgggcg ggaagatggc ggctgggttc aaaaccgtgg aacctctgga     300
gtattacagg agatttctga aagagaactg ccgtcctgat ggaagagaac ttggtgaatt     360
cagaaccaca actgtcaaca tcggttcaat tagtaccgca gatggttctg ctttagtgaa     420
gttgggaaat actacagtaa tctgtggagt taaagcagaa tttgcagcac catcaacaga     480 tgccctgat aaaggatacg ttgttcctaa tgtggatcta ccacccctgt gttcatcgag     540
attccggtct ggacctcctg gagaagaggc ccaagtggct agccagttca ttgcagatgt     600
```

```
cattgaaaat tcacagataa ttcagaaaga ggacttatgc atttctccag gaaagcttgt      660
ctgggttcta tactgtgatc tcatttgcct cgactacgat ggaaacattt tggatgcctg      720
cacatttgct ttgctagcgg cttttaaaaaa tgtacagttg cctgaagtta ctataaatga    780
agaaactgct ttagcagaag ttaatttaaa gaagaaaagt tatttgaata ttagaactca     840
tccagttgca acttcctttg ctgtgtttga tgacactttg cttatagttg accctactgg     900
agaggaggaa catctggcaa caggaacctt aacaatagta atggatgagg aaggcaaact     960
ctgttgtctt cacaaaccag gtggaagtgg gctaactgga gctaaacttc aggactgtat    1020
gagccgagca gttacaagac acaaagaagt taaaaaactg atggatgaag taattaagag    1080
tatgaaaccc aaataaacag ccaccacatt ttcaaaacag atttgtaaaa attgtatttg    1140
ttaacactgt gcacaaacgt tttatactaa ataaatatca aactacattc ttctgaaaga    1200
tgtttctatt atttcttagg tcacttccat atatattatg tatagtgaaa ccattttaa     1260
aaagcaatga cttaggcaaa ccaacccttag tttgttaaac catttccctg tttttattta    1320
aaaatgataa ggttgtgctt ctgtataaag tttgtacatc tagcaatgta aaatactgac    1380
acattaaaaa aaacaaaaag tagaaactca aaaaaaaaaa aaaaaa                   1427
```

<210> SEQ ID NO 2
<211> LENGTH: 1644
<212> TYPE: DNA
<213> ORGANISM: Homo sapiens

<400> SEQUENCE: 2

```
gatgacgtaa ttttcctgcg cctcggggcg agcagcggcg cgcaaggaaa gatcgggttc      60
cgttttttccc gcggattctg gtgcctgtgg ggccggtgac ccaacaccat gaaggaaacg    120
ccactctcaa actgcgaacg ccgcttccta ctccgtgcca tcgaagagaa gaagcggctg    180
gatggcagac aaacctatga ttataggaac atcaggatct catttggaac agattacgga    240
tgctgcattg tggaacttgg aaaaacaaga gttcttggac aggtttcctg tgaacttgtg    300
tctccaaaac tcaatcgggc aacagaaggt attcttttt ttaaccttga actctctcag    360
atggccgctc cagcttttcga acctggcagg cagtcagatc tcttggtgaa gttgaatcga    420
ctcatggaaa gatgtctaag aaattcgaag tgtatagaca ctgagtctct ctgtgttgtt    480
gctggtgaaa aggtttggca aatacgtgta gacctacatt tattaaatca tgatggaaat    540
attattgatg ctgccagcat tgctgcaatc gtggccttat gtcatttccg aagacctgat    600
gtctctgtcc aaggagatga agtaacactg tatacacctg aagagcgtga tcctgtacca    660
ttaagtatcc accacatgcc catttgtgtc agttttgcct ttttccagca aggaacatat    720
ttattggtgg atcccaatga acgagaagaa cgtgtgatgg atggcttgct ggtgattgcc    780
atgaacaaac atcgagagat ttgtactatc cagtccagtg gtgggataat gctactaaaa    840
gatcaagttc tgagatgcag taaaatcgct ggtgtgaaag tagcagaaat tacagagcta    900
atattgaaag ctttggagaa tgaccaaaaa gtaaggaaag aaggtggaaa gtttggtttt    960
gcagagtcta tagcaaatca aaggatcaca gcatttaaaa tggaaaaggc ccctattgat   1020
acctcggatg tagaagaaaa agcagaagaa atcattgctg aagcagaacc tccttcagaa   1080
gttgtttcta cacctgtgct atggactcct ggaactgccc aaattggaga gggagtagaa   1140
aactcctggg gtgatcttga agactctgag aaggaagatg atgaaggcgg tggtgatcaa   1200
gctatcattc ttgatggtat aaaaatggac actggagtag aagtctctga tattggaagc   1260
caagagctgg ggtttcacca tgttggccag actggactcg agttcctgac ctcagatgct   1320
```

-continued

```
cccataatac tctcagatag tgaagaagaa gaaatgatca ttttggaacc agacaagaat   1380
ccaaagaaaa taagaacaca gaccaccagt gcaaacaag aaaaagcacc aagtaaaaag    1440
ccagtgaaaa aagaaaaaaa gaagagagct gccaattaaa gctaacagtt gtatatctgt   1500
atatataact attaaaaggg atatttattc cattctgaga accctgggta ttttttattc   1560
acaaatccat tataaaatct agcaggattt taaaaatagt tttttgtttt taatgtgctt   1620
taaaataata aaccttctgg agca                                         1644
```

<210> SEQ ID NO 3
<211> LENGTH: 1593
<212> TYPE: DNA
<213> ORGANISM: Homo sapiens

<400> SEQUENCE: 3

```
gatgacgtaa ttttcctgcg cctcggggcg agcagcggcg cgcaaggaaa gatcgggttc     60 cgttttccc gcggattctg gtgcctgtgg ggccggtgac ccaacaccat gaaggaaacg     120
ccactctcaa actgcgaacg ccgcttccta ctccgtgcca tcgaagagaa gaagcggctg    180
gatggcagac aaacctatga ttataggaac atcaggatct catttggaac agattacgga    240
tgctgcattg tggaacttgg aaaaacaaga gttcttggac aggtttcctg tgaacttgtg    300
tctccaaaac tcaatcgggc aacagaaggt attcttttt ttaaccttga actctctcag    360
atggccgctc cagctttcga acctggcagg cagtcagatc tcttggtgaa gttgaatcga    420
ctcatggaaa gatgtctaag aaattcgaag tgtatagaca ctgagtctct ctgtgttgtt    480
gctggtgaaa aggtttggca aatacgtgta gacctacatt tattaaatca tgatggaaat    540
attattgatg ctgccagcat tgctgcaatc gtggccttat gtcatttccg aagacctgat    600
gtctctgtcc aaggagatga agtaacactg tatacacctg aagagcgtga tcctgtacca    660
ttaagtatcc accacatgcc catttgtgtc agttttgcct ttttccagca aggaacatat    720
ttattggtgg atcccaatga acgagaagaa cgtgtgatgg atggcttgct ggtgattgcc    780
atgaacaaac atcgagagat ttgtactatc cagtccagtg gtgggataat gctactaaaa    840
gatcaagttc tgagatgcag taaaatcgct ggtgtgaaaa tagcagaaat tacagagcta    900
atattgaaag cttttggagaa tgaccaaaaa gtaaggaaag aaggtggaaa gtttggtttt    960
gcagagtcta tagcaaatca aaggatcaca gcatttaaaa tggaaaaggc ccctattgat   1020
acctcggatg tagaagaaaa agcagaagaa atcattgctg aagcagaacc tccttcagaa   1080
gttgttccta cacctgtgct atggactcct ggaactgccc aaattggaga gggagtagaa   1140
aactcctggg gtgatcttga agactctgag aaggaagatg atgaaggcgg tggtgatcaa   1200
gctatcattc ttgatggtat aaaaatggac actggagtag aagtctctga tattggaagc   1260
caagatgctc ccataatact ctcagatagt gaagaagaag aaatgatcat tttggaacca   1320
gacaagaatc caaagaaaat aagaacacag accaccagtg caaacaaga aaaagcacca   1380 agtaaaaagc cagtgaaaag aagaaaaaag aagagagctg ccaattaaag ctaacagttg   1440
tatatctgta tataactta ttaaagggga tatttattcc attctgagaa ccctgggtat   1500
tttttattca caaatccatt ataaaatcta gcaggatttt aaaaatagtt ttttgttttt   1560
aatgtgcttt aaaataataa accttctgga gca                               1593
```

<210> SEQ ID NO 4
<211> LENGTH: 7589
<212> TYPE: DNA

<213> ORGANISM: Homo sapiens

<400> SEQUENCE: 4

| | | | | | |
|---|---|---|---|---|---|
| gatgttccga | ggagcggaaa | gcaacacacg | ttgtgaggtg | gcgtccagaa | ggaagccccg | 60 |
| cctaggccac | gggcggaaat | ggctcctcgc | cttgctttgc | cgcccctccc | cactctcgcc | 120 |
| caatccccgc | ggccgtcaga | gagccaacca | atgtttatct | cggcattttc | ccgcgagaag | 180 |
| tgttactaat | atccgggaat | ggaaagggaa | gaacctccgg | ggttaggcgt | attctagatt | 240 |
| gacgcctttt | gctggaagag | cgctgctggg | gttaggattc | tgcgcggcga | ggcaagatgc | 300 |
| tcaagtccaa | gacgttctta | aaaaagaccc | gggcgggcgg | cgtgatgaag | atcgtgcgcg | 360 |
| agcactacct | gcgagacgac | atcggctgcg | gtgcgcccgg | gtgcgcagcg | tgtggagggg | 420 |
| cgcacgaggg | gccggccctg | gagccgcagc | cccaggaccc | ggcgagcagc | gtctgcccgc | 480 |
| aaccgcacta | cttgctgccc | gacactaatg | tgttactgca | ccagattgat | gttcttgagg | 540 |
| accctgccat | caggaatgta | attgtgctac | aaacagttct | tcaagaagtg | agaaatcgca | 600 |
| gtgcccccgt | atataaacgc | atccgagatg | tgactaataa | ccaagagaag | catttctata | 660 |
| ctttcactaa | tgagcaccat | agagaaacct | atgtagaaca | agaacaggga | gaaaatgcta | 720 |
| atgacaggaa | tgatagagcg | attcgagtag | cagcaaaatg | gtacaatgaa | catttgaaaa | 780 |
| aaatgtcagc | agacaaccag | ctgcaagtta | tcttcataac | aaatgacagg | agaaacaaag | 840 |
| agaaagccat | agaagaagga | ataccagctt | tcacttgtga | agaatatgta | aagagcctaa | 900 |
| ctgctaaccc | cgaactcata | gatcgtcttg | cttgtttgtc | tgaagaaggg | aatgaaatag | 960 |
| aaagtggaaa | ataatatttt | tcagagcatc | ttcccttaag | taagctacag | caaggcataa | 1020 |
| aatctggtac | ataccttcaa | ggaacattta | gagctagcag | ggaaaattac | ttggaagcta | 1080 |
| cagtatggat | tcatggcgac | aatgaagaaa | ataagagat | aatcttacag | ggacttaaac | 1140 |
| atttaaacag | agctgttcac | gaagatattg | tggctgtgga | gcttctcccc | aagagtcagt | 1200 |
| gggtagcacc | atcttctgtg | gttttacatg | atgaaggtca | aaatgaagaa | gatgtggaga | 1260 |
| aagaagaaga | gacagaacga | atgcttaaga | ctgctgtaag | cgagaaaatg | ttgaagccta | 1320 |
| caggtagagt | tgtaggaata | ataaaaagga | attggagacc | atattgtggc | atgctttcca | 1380 |
| agtctgacat | taaggagtca | agaagacatc | tctttacacc | tgctgataag | agaatccctc | 1440 |
| gaattcgcat | agaaaccaga | caggcttcca | cattagaagg | acggagaatt | attgttgcta | 1500 |
| ttgatggttg | gcccagaaat | tccagatatc | caaatggaca | ctttgtgaga | aatttaggtg | 1560 |
| atgttggaga | gaaagagact | gaaacagaag | ttttgttact | tgaacacgat | gttccccatc | 1620 |
| agccttttc | acaggctgtt | cttagttttc | tgccaaagat | gccctggagc | attactgaaa | 1680 |
| aggacatgaa | aaaccgagaa | gacctgaggc | atctgtgtat | ttgtagtgta | gacccaccag | 1740 |
| gatgtactga | tatagacgat | gctctacatt | gtcgagaact | cgaaaatgga | aatttggagg | 1800 |
| ttggtgttca | tattgctgat | gtgagccatt | ttattaggcc | aggaaatgcc | ttggatcaag | 1860 |
| aatcagccag | aagaggaaca | actgtgtatc | tttgtgaaaa | gaggattgac | atggttccag | 1920 |
| agttgcttag | ctctaacttg | tgttccttaa | aatgtgacgt | ggacaggctg | gcatttcat | 1980 |
| gtatttggga | aatgaatcac | aatgctgaaa | tcttaaaaac | gaagtttacc | aaaagtgtta | 2040 |
| ttaattcaaa | ggcatctctg | acgtatgctg | aagctcagtt | gagaattgat | tcagcaaaca | 2100 |
| tgaatgatga | tattaccact | agtctccgtg | gactgaataa | actagccaaa | attctgaaga | 2160 |
| aaagaaggat | tgaaaagggg | gctttgactc | tatcctctcc | tgaagttcga | ttccacatgg | 2220 |
| acagtgaaac | tcacgatcct | atagatctgc | agaccaagga | acttagggaa | acaaattcca | 2280 |

```
tggttgaaga atttatgtta cttgccaata tttctgttgc aaaaaaaatt catgaggaat    2340
tttctgaaca tgctctgctt cgaaaacatc ctgctccacc tccatcaaat tatgaaattc    2400
ttgttaaggc agccaggtca aggaatttgg aaattaagac tgatacagcc aagtctttgg    2460
ctgagtcttt ggatcaggcc gaatctccta cttttccata tctaaacact ctgttgagaa    2520
tattagccac tcgctgtatg atgcaagctg tgtacttctg ttctggaatg gataatgatt    2580
ttcatcacta tggcttagcg tctccaatat acacacattt tacttcaccc attagaagat    2640
acgcagatgt cattgttcat cggcttttgg ctgtggctat tggggctgac tgtacttatc    2700
cagagttgac agacaaacac aagcttgcag atatatgtaa aaatctaaat ttccggcaca    2760
aaatggctca atatgcccaa cgtgcatcag tggcttttca tacccagtta ttcttcaaaa    2820
gcaaaggaat agtaagtgaa gaagcctata ttttatttgt aagaaagaat gccattgtgg    2880
tattaattcc aaagtatggt ttagaaggga cagtcttttt tgaagaaaag gacaaaccaa    2940
acccacagct tatttatgat gatgagatac cctcacttaa aatagaagat acagtgttcc    3000
atgtatttga taaagttaaa gtgaaaatca tgttagactc atctaatctt caacatcaga    3060
agatccgaat gtccctggta gaaccacaga taccaggaat aagcattcct actgatactt    3120
caaacatgga ccttaatgga ccaaagaaaa agaagatgaa gcttggaaaa tagctatatt    3180
caacaaaaat cttcaaagac tggtttcttt tttaaaagaa aaacttgaa agaacacttc    3240 taagcctaag tgtgtgatac agtttgttac ttttaagtac attttaataa tttcagacat    3300
ctgcattttt attgaacagt tgactgtatc tgacccatca tactactata cttctgggtt    3360
gaacagaatt atttatgcag aataattcaa ttgaatatcc atcacttaaa tacagtgaca    3420
ggacagcaac ttcagggatc tgtaaagatc atttaaatgg agtgctcatc tcattgagga    3480
gcagattaat tttgcgtaag tactttgatt atttaatatt tgtaagaaaa aactttcatt    3540
ttcctacaga ggaaaataga acaattttag aagcaaggaa caatctcttt tctaagtctt    3600
ggaagctgtc agtgttgagg atgtaatctc ctttgccatc tttaattcac ctaacttaca    3660
ctaggtgttc tcttactgtc tttaaaagct tcctgtattt tattagtggt ccttgaaaaa    3720
ctgtgaatgt ttgggaattg gtagaaaggc aaaaagtagg atattttgac ctgactggaa    3780
agatggttgt gtttttattg ccaggtaata agtgtgatca ttgttgaact tcagctccag    3840
tgtctctcca gaataagaca ttggcattca aatgtctata tcttgttact tacaaaataa    3900
aaaacagatt aattagtggc ttttaaattg tagttatatc agtgtatata cacgagggga    3960
actgtataaa gacatactaa agggaacaga ttaaaataag tattattaat aaaatttggt    4020
gtgccagact gactacttcc cttgctaatc acagagatta gtaatgatta aattaatatc    4080
ttcaggaata ttttgggata gggttgcctt aaaacatttt acttggctta ttcaatttct    4140
aaagcactta cgttgtgcca ggttccactc aagtaaatta tctctgcctt caaggagctt    4200
gcagtatagt gagaaaagcc tgccaagtaa atcagcaggt atactaaata ggtagtcatt    4260
taggcactca ataaatgttg actaattttt ccagtttcct attactgagg aaaacctcca    4320
tacactgagg cagaaacttg tgtcagttgg aggaaaatag acttgagtag tctttggtcc    4380
aggtaaaatg ggtcagtgac actgaaacag tagagtagga gtcaaaaaac cttttctgtg    4440
aagtgctaga acatttaga ctttgttggc tatggtctgt attgcaacta tagtacacaa    4500
ctctgccgtt gatagtgtgt aaggagccat atacaatatg taaacaaatc aacatgactg    4560
tgtttcaaca aggcctgatt tgttaagttt catatatagt catatgtcac ttaatgacag    4620
```

```
ggatatgttc tgagacatgt cacttggcaa tttcatcatt gtgtgaaaat catgatgtag    4680
ttacacaaac ctagatggta taccctatgg tatcctatat gggatagcct attgctccta    4740
acctacaaac ctgtatggca tattactgta ctgattactg taggcggttg taacacagtg    4800
ctaagtattt gtgtatctaa acatatctaa acatagaaaa ggtacagtaa aaatatatat    4860
atagatatat ataagatata aaatggtaca cctatttagg acatttacca tgaacaagtt    4920
ggcaggactg gaagctggct ctgggtgagt cagtaagtgg ttagtgaatg tgaaggccat    4980
gatattactg tgcactactg tagactttta taaacactat atacttaggc tacataaagt    5040
aatttcacta tgatgttacc atggctgtgt ccccaggcaa taggaatttt tcagctccat    5100
tgtaatctta cgggatcatc atcgtatatt tggccattgt tgaccaaaag ttatgcagca    5160
catcattata attttgatgt gtcacaaaac attactcatt tgatttcccc cacccccgcc    5220
aaccatttaa aaaagtttgc cggctaggtg cggtggctca tgcctgtaat cctagcattt    5280
tgggaggacg aggcgggtgg atcactcgat gtcaggagtt tgagaccagc ctggccaaca    5340
tggtaaaacg ccgtctctac taaaaataca aaaacttagc tgggtgtaac ggcggatgcc    5400
tgtaatccca gctacttggg aggctgaggc aggagaatcg cttgaacctg ggaggcggaa    5460
gttgcagtga gccgagattg caccactgca gttcagcctg gatgatgaga gtgagactcc    5520
atcgcaaaaa aaaaaaaaaa aaagaaaag aaaattagcc aggtgtggtg gcaagtgcct    5580
ttaatcccac ctcaggaggc tgaggcagga gaatcgcttg aacctgggag gcagaggttg    5640
cagtgagcca agatcgcgcc actgcactcc agcctgggtg acagaacaag actgtctcaa    5700 aaaaaaaaa agaagagaaa aactgcctac aggccatagt taacctgcaa tagagaagaa    5760
agggaagtag ggcagtgcat gactggcctt aggttttttc tttccaagtt tattttcttg    5820
tgcttcagct actagaaagg tttaattcag ggataagtcc caattgagta gttcaagatg    5880
atcagagact ttgctatttt cccctaagtt ctattccata atctaaaatg ttctgtttct    5940
agtgccagtt cttatgctaa gcaggttacg tggaatatat cacttaactc aaaaagccct    6000
gttaagccag gactgttatc tccatttaac agatgagaaa atggaggttt atggtctgtt    6060
ctcacactgc tacgaagaaa taccccaaac tgggtaatta ttataaagga aagaggttta    6120
atggactcag ttccgcattg ctggtgaggc ctcaggacac ttacacaatc atggcagaaa    6180
aaggagaagc aggcaccttt ttcacagggc ggcaggatga aaatgactgc cagcagtgga    6240
aatgccagac gcttataaaa ccttcagatc tcatgagacc ggctcactat cacaggaaca    6300
gcatggagga aaccgccccc atgatccagt tacctccacc tggtcccacc cttgacacgt    6360
ggggattgct acaattcaag gttagatttg ggtgaggaca cagagccata ccatatcagc    6420
ccagatcaag tagtgacaga gtagggattt gaatacaggt tatagtcact attgtgttat    6480
ttcttgactt ttgtactatt aaaaaactgt agccagtgag gcttctaccc ttagtaccca    6540
gaactccttt taggtatagc aattgttttt aggtaaattt atattgagtt taacacctgt    6600
gtgattaaag acaactttcc aatgtagtat ctgtagccat gtccctaat ggctattagt    6660 gttcatggtt agtgtgttga agatgagcca ggtacataac gcggcacatt ttctgcaggt    6720
cagcagtaag gtttcaaggt acagttatgg aggaaagaag aaaatgacac attgataaca    6780
caggtcttta ttcccttttg aatgagacag ttttttaaaag ttgatttata aatacaaaaa    6840
tacattctcc aaagatagta tttccaaact gttatatacc catctactcc caacatggat    6900
ataagttttt taaaaaaata gttgtatata acatacatat ctgccccagt gttacttcac    6960
aggcctatgc cctacgggaa ctccactctc ccagccccac ttttttctctt ggttctccca    7020
```

```
cattcttatt ctcccacatc cctacccacg tttgagctgg aaaggatgtc cctaccctag    7080
gcatgaggta tattttattc tgggcaccac acatttgccc catagataac aatacacgtg    7140
atgatgtcac tagtactacc tttctagtat ttacatactt aaaagtagta actagaacag    7200
ttatcactgg aactaagaat tttccccaca gaggtgaaca gaccaagaac taaaatttca    7260
ggaaacctgt ttaatttctt ttgtatcttt gaaaagttag ttttatatct aagatttctt    7320
cacataggtt ataattcatc tgtatgttca agcttttatg taaaaatata tagtgccttc    7380
agttttaaca tagtttcaca tgttctcaga actgctaaat tcagtgctac cagtaaggct    7440
taataagtag ttcattgacc ctgtaagata ggagcactca gctctgtcac aatttgttgt    7500
taaacacatc actcaatgta agtataaaaa tatttattga taaaaaataa acttataatt    7560
cagcaaaaaa aaaaaaaaaa aaaaaaaaa                                     7589

<210> SEQ ID NO 5
<211> LENGTH: 7499
<212> TYPE: DNA
<213> ORGANISM: Homo sapiens

<400> SEQUENCE: 5
gatgttccga ggagcggaaa gcaacacacg ttgtgaggtg gcgtccagaa ggaagccccg      60
cctaggccac gggcggaaat ggctcctcgc cttgctttgc cgcccctccc cactctcgcc     120
caatccccgc ggccgtcaga gagccaacca atgtttatct cggcattttc ccgcgagaag     180
tgttactaat atccgggaat ggaaagggaa gaacctccgg ggttaggcgt attctagatt     240
gacgcctttt gctggaagag cgctgctggg gttaggattc tgcgcggcga ggcaagatgc     300
tcaagtccaa gacgttctta aaaaagaccc gggcgggcgg cgtgatgaag atcgtgcgcg     360
agcactacct gcgagacgac atcggctgcg gtgcgcccgg gtgcgcagcg tgtggagggg     420
cgcacgaggg gccggccctg gagccgcagc cccaggaccc ggcgagcagc gtctgcccgc     480
aaccgcacta cttgctgccc gacactaatg tgttactgca ccagattgta agtgcctgga     540
ggccggggac ctgggcttct gtggcctcca gcctgcgact cccaggcagc ttagaaacct     600
atgtagaaca agaacaggga gaaaatgcta atgacaggaa tgatagagcg attcgagtag     660
cagcaaaatg gtacaatgaa catttgaaaa aaatgtcagc agacaaccag ctgcaagtta     720
tcttcataac aaatgacagg agaaacaaag agaaagccat agaagaagga ataccagctt     780
tcacttgtga agaatatgta aagagcctaa ctgctaaccc cgaactcata gatcgtcttg     840
cttgtttgtc tgaagaaggg aatgaaatag aaagtggaaa aataatattt tcagagcatc     900
ttcccttaag taagctacag caaggcataa aatctggtac ataccttcaa ggaacattta     960
gagctagcag ggaaaattac ttggaagcta cagtatggat tcatggcgac aatgaagaaa    1020
ataaagagat aatcttacag ggacttaaac atttaaacag agctgttcac gaagatattg    1080
tggctgtgga gcttctcccc aagagtcagt gggtagcacc atcttctgtg gttttacatg    1140
atgaaggtca aaatgaagaa gatgtggaga agaagaagaa gacagaacga atgcttaaga    1200
ctgctgtaag cgagaaaatg ttgaagccta caggtagagt tgtaggaata ataaaaagga    1260
attggagacc atattgtggc atgctttcca agtctgacat taaggagtca agaagacatc    1320
tctttacacc tgctgataag agaatccctc gaattcgcat agaaaccaga caggcttcca    1380
cattagaagg acgagaatt attgttgcta ttgatggttg gccagaaat tccagatatc    1440 caaatggaca ctttgtgaga aatttaggtg atgttggaga gaaagagact gaaacagaag    1500
```

```
ttttgttact tgaacacgat gttccccatc agccttttc acaggctgtt cttagttttc    1560
tgccaaagat gccctggagc attactgaaa aggacatgaa aaaccgagaa gacctgaggc    1620
atctgtgtat ttgtagtgta gacccaccag gatgtactga tatagacgat gctctacatt    1680
gtcgagaact cgaaaatgga aatttggagg ttggtgttca tattgctgat gtgagccatt    1740
ttattaggcc aggaaatgcc ttggatcaag aatcagccag aagaggaaca actgtgtatc    1800
tttgtgaaaa gaggattgac atggttccag agttgcttag ctctaacttg tgttccttaa    1860
aatgtgacgt ggacaggctg gcattttcat gtatttggga aatgaatcac aatgctgaaa    1920
tcttaaaaac gaagtttacc aaaagtgtta ttaattcaaa ggcatctctg acgtatgctg    1980
aagctcagtt gagaattgat tcagcaaaca tgaatgatga tattaccact agtctccgtg    2040
gactgaataa actagccaaa attctgaaga aagaaggat tgaaaaaggg ctttgactc      2100 tatcctctcc tgaagttcga ttccacatgg acagtgaaac tcacgatcct atagatctgc    2160
agaccaagga acttagggaa acaaattcca tggttgaaga atttatgtta cttgccaata    2220
tttctgttgc aaaaaaaatt catgaggaat tttctgaaca tgctctgctt cgaaaacatc    2280
ctgctccacc tccatcaaat tatgaaattc ttgttaaggc agccaggtca aggaatttgg    2340
aaattaagac tgatacagcc aagtcttttgg ctgagtcttt ggatcaggcc gaatctccta    2400
cttttccata tctaaacact ctgttgagaa tattagccac tcgctgtatg atgcaagctg    2460
tgtacttctg ttctggaatg gataatgatt ttcatcacta tggcttagcg tctccaatat    2520
acacacattt tacttcaccc attagaagat acgcagatgt cattgttcat cggcttttgg    2580
ctgtggctat tggggctgac tgtacttatc cagagttgac agacaaacac aagcttgcag    2640
atatatgtaa aaatctaaat ttccggcaca aaatggctca atatgcccaa cgtgcatcag    2700
tggcttttca tacccagtta ttcttcaaaa gcaaaggaat agtaagtgaa gaagcctata    2760
ttttatttgt aagaaagaat gccattgtgg tattaattcc aaagtatggt ttagaaggga    2820
cagtcttttt tgaagaaaag gacaaaccaa acccacagct tatttatgat gatgagatac    2880
cctcacttaa aatagaagat acagtgttcc atgtatttga taaagttaaa gtgaaaatca    2940
tgttagactc atctaatctt caacatcaga agatccgaat gtccctggta gaaccacaga    3000
taccaggaat aagcattcct actgatactt caaacatgga ccttaatgga ccaaagaaaa    3060
agaagatgaa gcttggaaaa tagctatatt caacaaaaat cttcaaagac tggtttcttt    3120
tttaaaagaa aaaacttgaa agaacacttc taagcctaag tgtgtgatac agtttgttac    3180
ttttaagtac attttaataa tttcagacat ctgcattttt attgaacagt tgactgtatc    3240
tgacccatca tactactata cttctggggtt gaacagaatt atttatgcag aataattcaa    3300
ttgaatatcc atcacttaaa tacagtgaca ggacagcaac ttcagggatc tgtaaagatc    3360
atttaaatgg agtgctcatc tcattgagga gcagattaat tttgcgtaag tactttgatt    3420
atttaatatt tgtaagaaaa aactttcatt ttcctacaga ggaaaataga acaattttag    3480
aagcaaggaa caatctcttt tctaagtctt ggaagctgtc agtgttgagg atgtaatctc    3540
ctttgccatc tttaattcac ctaacttaca ctaggtgttc tcttactgtc tttaaaagct    3600
tcctgtattt tattagtggt ccttgaaaaa ctgtgaatgt ttgggaattg gtagaaaggc    3660
aaaaagtagg atatttgac ctgactggaa agatggttgt gttttattg ccaggtaata    3720 agtgtgatca ttgttgaact tcagctccag tgtctctcca gaataagaca ttggcattca    3780
aatgtctata tcttgttact tacaaaataa aaaacagatt aattagtggc ttttaaattg    3840
tagttatatc agtgtatata cacgaggga actgtataaa gacatactaa agggaacaga    3900
```

```
ttaaaataag tattattaat aaaatttggt gtgccagact gactacttcc cttgctaatc    3960
acagagatta gtaatgatta aattaatatc ttcaggaata ttttgggata gggttgcctt    4020
aaaacatttt acttggctta ttcaatttct aaagcactta cgttgtgcca ggttccactc    4080
aagtaaatta tctctgcctt caaggagctt gcagtatagt gagaaaagcc tgccaagtaa    4140
atcagcaggt atactaaata ggtagtcatt taggcactca ataaatgttg actaattttt    4200
ccagtttcct attactgagg aaaacctcca tacactgagg cagaaacttg tgtcagttgg    4260
aggaaaatag acttgagtag tctttggtcc aggtaaaatg ggtcagtgac actgaaacag    4320
tagagtagga gtcaaaaaac cttttctgtg aagtgctaga acattttaga ctttgttggc    4380
tatggtctgt attgcaacta tagtacacaa ctctgccgtt gatagtgtgt aaggagccat    4440
atacaatatg taaacaaatc aacatgactg tgtttcaaca aggcctgatt tgttaagttt    4500
catatatagt catatgtcac ttaatgacag ggatatgttc tgagacatgt cacttggcaa    4560
tttcatcatt gtgtgaaaat catgatgtag ttacacaaac ctagatggta tacccctatgg   4620 tatcctatat gggatagcct attgctccta acctacaaac ctgtatggca tattactgta    4680
ctgattactg taggcggttg taacacagtg ctaagtattt gtgtatctaa acatatctaa    4740
acatagaaaa ggtacagtaa aaatatatat atagatatat ataagatata aatggtaca     4800 cctatttagg acatttacca tgaacaagtt ggcaggactg gaagctggct ctgggtgagt    4860
cagtaagtgg ttagtgaatg tgaaggccat gatattactg tgcactactg tagacttttta   4920 taaacactat atacttaggc tacataaagt aatttcacta tgatgttacc atggctgtgt    4980
ccccaggcaa taggaatttt tcagctccat tgtaatctta cgggatcatc atcgtatatt    5040
tggccattgt tgaccaaaag ttatgcagca catcattata attttgatgt gtcacaaaac    5100
attactcatt tgatttcccc cacccccgcc aaccatttaa aaaagtttgc cggctaggtg    5160
cggtggctca tgcctgtaat cctagcattt gggaggacg aggcgggtgg atcactcgat     5220
gtcaggagtt tgagaccagc ctggccaaca tggtaaaacg ccgtctctac taaaaataca    5280
aaaacttagc tgggtgtaac ggcggatgcc tgtaatccca gctacttggg aggctgaggc    5340
aggagaatcg cttgaacctg ggaggcggaa gttgcagtga ccgagattg caccactgca     5400 gttcagcctg gatgatgaga gtgagactcc atcgcaaaaa aaaaaaaaaa aaaagaaaag    5460
aaaattagcc aggtgtggtg gcaagtgcct ttaatcccac ctcaggaggc tgaggcagga    5520
gaatcgcttg aacctgggag gcagaggttg cagtgagcca agatcgcgcc actgcactcc    5580
agcctgggtg acagaacaag actgtctcaa aaaaaaaaaa agagaagaaa aactgcctac    5640
aggccatagt taacctgcaa tagagaagaa agggaagtag ggcagtgcat gactggcctt    5700 aggtttttttc tttccaagtt tattttcttg tgcttcagct actagaaagg tttaattcag    5760
ggataagtcc caattgagta gttcaagatg atcagagact ttgctatttt cccctaagtt    5820
ctattccata atctaaaatg ttctgtttct agtgccagtt cttatgctaa gcaggttacg    5880
tggaatatat cacttaactc aaaaagccct gttaagccag gactgttatc tccatttaac    5940
agatgagaaa atggaggttt atggtctgtt ctcacactgc tacgaagaaa taccccaaac    6000
tgggtaatta ttataaagga aagaggttta atggactcag ttccgcattg ctggtgaggc    6060
ctcaggacac ttacacaatc atggcagaaa aaggagaagc aggcaccttt ttcacagggc    6120
ggcaggatga aaatgactgc cagcagtgga aatgccagac gcttataaaa ccttcagatc    6180
tcatgagacc ggctcactat cacaggaaca gcatggagga aaccgccccc atgatccagt    6240
```

```
tacctccacc tggtcccacc cttgacacgt ggggattgct acaattcaag gttagatttg      6300
ggtgaggaca cagagccata ccatatcagc ccagatcaag tagtgacaga gtagggattt      6360
gaatacaggt tatagtcact attgtgttat ttcttgactt ttgtactatt aaaaaactgt      6420
agccagtgag gcttctaccc ttagtaccca gaactccttt taggtatagc aattgttttt      6480
aggtaaattt atattgagtt taacacctgt gtgattaaag acaactttcc aatgtagtat      6540
ctgtagccat gtccctaat ggctattagt gttcatggtt agtgtgttga agatgagcca       6600
ggtacataac gcggcacatt ttctgcaggt cagcagtaag gtttcaaggt acagttatgg      6660
aggaaagaag aaaatgacac attgataaca caggtcttta ttcccttttg aatgagacag      6720
tttttaaaag ttgatttata aatacaaaaa tacattctcc aaagatagta tttccaaact      6780
gttatatacc catctactcc caacatggat ataagttttt taaaaaaata gttgtatata      6840
acatacatat ctgccccagt gttacttcac aggcctatgc cctacgggaa ctccactctc      6900
ccagccccac ttttttctctt ggttctccca cattcttatt ctcccacatc cctacccacg      6960
tttgagctgg aaaggatgtc cctaccctag gcatgaggta tatttattc tgggcaccac       7020 acatttgccc catagataac aatacacgtg atgatgtcac tagtactacc tttctagtat      7080
ttacatactt aaaagtagta actagaacag ttatcactgg aactaagaat tttccccaca      7140
gaggtgaaca gaccaagaac taaaatttca ggaaacctgt ttaatttctt ttgtatctttt     7200 gaaaagttag ttttatatct aagatttctt cacataggtt ataattcatc tgtatgttca      7260
agcttttatg taaaaatata tagtgccttc agtttttaaca tagtttcaca tgttctcaga    7320
actgctaaat tcagtgctac cagtaaggct taataagtag ttcattgacc ctgtaagata     7380
ggagcactca gctctgtcac aatttgttgt taaacacatc actcaatgta agtataaaaa     7440
tatttattga taaaaaataa acttataatt cagcaaaaaa aaaaaaaaaa aaaaaaaa       7499

<210> SEQ ID NO 6
<211> LENGTH: 3795
<212> TYPE: DNA
<213> ORGANISM: Homo sapiens

<400> SEQUENCE: 6
gggagacacg ccgccatgct gcagaagcgg gagaaggtgc tgctgctgag gaccttccag        60
ggccgcacgc tgcggatcgt gcgcgagcac tacctgcggc cctgcgtgcc ctgccacagc       120
ccgctctgcc cgcagcccgc cgcctgcagc cacgatggga aactcttgtc tagtgatgtg       180
actcattacg tgatcccaga ctggaaagtt gttcaagatt atcttgagat ccttgagttt       240
cctgagttga agggaattat tttcatgcag acagcttgtc aagctgtgca gcatcaaaga       300
ggcaggagac agtataacaa actgcgaaac ctgctgaagg atgcgcgtca tgattgcatt       360
ctctttgcta atgaattcca gcaatgctgc tatctgccac gggaagagg agagtccatg        420 gagaagtggc agaccaggag catatacaac gcagctgttt ggtactatca tcactgccag       480
gacaggatgc caattgttat ggtgacagaa gatgaagagg caattcagca gtatggaagt       540
gaaacagaag gagtattcgt gattactttc aagaattacc tggacaattt ctggcctgat       600
ttaaaagctg cccacgagct ttgtgattct atccttcagt ctcgacggga gagagagaat       660
gagagtcagg agagccatgg gaaggagtac ccagaacatc ttcccctgga agtgttagaa       720
gctgggatta aatctggacg ctatatccag ggaattctga atgtcaacaa acacagagcc       780
caaatagaag cttttgttcg acttcaagga gccagcagta aagattcaga tttagtcagt       840
gacatcctaa tccacgggat gaaggctcga aaccgctcaa ttcatggaga tgtggtagtt       900
```

```
gtggagctgc ttcctaaaaa tgaatggaaa ggaagaaccg tagccctgtg tgagaatgac    960
tgtgacgaca aggcttcggg cgagtcccca agtgagccca tgcctacagg tcgagtggtg   1020
ggcatacttc agaagaactg gcgggattat gtggtgacat ttccgtccaa agaagaggtc   1080
caatctcagg gcaaaaatgc tcagaaaatc ctggttacac cttgggatta cagaattccc   1140
aaaattcgaa ttagcactca gcaagcagaa accctccagg acttcagggt ggtcgtgcgc   1200
atcgattcct gggagtcaac atctgtgtat ccaaatggac attttgtgcg tgttttagga   1260
agaatcggag atctggaagg ggaaattgca accatcctgg tggaaaacag tatttcagtt   1320
attcctttct cagaagctca gatgtgtgag atgccagtaa acacaccaga agtccctgg    1380
aaggtgagtc ctgaagagga acaaaaacgt aaagacttga ggaaaagcca tctcgtattc   1440
agcattgacc ccaaaggttg tgaagatgtg atgacacac tctcagtcag aaccttaaat    1500
aatggcaacc tggaacttgg ggtccacatc gcagatgtaa cacactttgt ggcaccaaat   1560
tcttacattg atattgaagc tagaacaagg gccaccactt attatctagc agatcgtcgc   1620
tatgacatgc tgccttccgt cctcagtgca gatttgtgtt cccttctggg aggcgttgat   1680
aggtatgctg taagcatcat gtgggaactg gataaagcct cttatgaaat taagaaagtg   1740
tggtatggca gaaccattat tcgatcagca tacaaactgt tctatgaagc agcccaagaa   1800
ctactggatg gaaacttaag cgttgttgat gatattccag aattcaaaga cttggatgag   1860
aagagcagac aagccaagct ggaggagttg gtgtgggcaa ttggaaagct gaccgacata   1920
gctcgccatg tcagagctaa acgagacgga tgtggtgccc tggaactgga aggggtagag   1980
gtttgcgtac agctagatga caaaaagaac attcacgacc tcatcccaa gcagcccctg    2040
gaagtccacg agacagtggc tgaatgcatg atcctggcca accactgggt cgccaaaaag   2100
atctgggaga gcttccctca tcaggccttg ctgcgccagc ccctcctcc acaccaggag    2160
ttcttttcag aactccggga atgtgctaaa gccaaaggct tcttcataga tacacggtcc   2220
aataaaacac tggctgattc tctggataat gcgaacgacc cccacgatcc cattgtgaac   2280
aggctactgc gctccatggc cacgcaggcc atgtcgaatg ctctgtactt ctccaccgga   2340
tcctgtgcgg aggaggagtt ccatcattac ggtcttgcat tagataaata tacccacttt   2400
acttctccaa taagaagata ttcagatatt gtagtacacc gcttgttaat ggcagccatt   2460
tcaaaagata agaaaatgga aattaaggga aatctgttca gcaacaaaga tcttgaggaa   2520
ttatgcagac atatcaacaa cagaaaccaa gcagcacagc attctcagaa gcagtctact   2580
gagctcttcc agtgcatgta cttcaaagac aaagaccctg ccaccgagga gcgttgcata   2640
tctgacggag ttatttattc aattagaaca aatggtgtgc ttctatttat accaaggttt   2700
gggattaaag gtgctgctta tctaaaaaat aaagatggtt tagtcatctc atgtggccca   2760
gatagctgtt ctgaatggaa accaggatcc cttcaacgat tcaaaacaa aattacctct    2820
actacaacag atggggaatc tgttacgttc catttgtttg accatgtaac cgtaagaata   2880
tccatacagg cctcacgttg ccattctgat acaatcagac ttgaaataat tagtaacaaa   2940
ccatacaaga taccaaatac agaacttatt catcagagtt ccccttgct gaagagtgag    3000
ttagtgaaag aagtaactaa atctgtggaa gaagctcagc ttgcccaaga agtcaaagta   3060
aacatcattc aggaggaata tcaagaatat cgccaaacaa agggaaggag cctatacaca   3120
cttctagagg agatacggga cctagctctc ctggatgttt caaacaatta tggaatatga   3180
gaggctctta cttcactaag agctgtcata tgtgaatgtt ttacagtctt ttcaaactta   3240
```

```
acatttaatg tgtgtcactc agtgctctag tcgatcagga ctgggtagct atttcgcata    3300
tatgtaaaat gttctcagcc gggcacggtg gctcacgcct gtaacccag cactttggga    3360 ggctgaggcg gcggatcac gaggtcagga gattgagacc atcctggcta acacggtgaa    3420
acccagtctc tactaaaaat acaaaaatta gccggcgtg gtggcatgcg cctgtagtcc    3480
cagctacttg ggaggctgaa gcaggagaat tgcctgaacc caggaagagg aggttgcagt    3540
gagccgagat cgcaccactg cattccagcc tgggcaacag agcgagactc catctcaaaa    3600
aaaaaaaaaa aaaaaaaaa agttctctca ttcattaaag ttgcattaaa taaagtataa    3660
ttaggtcact atggaaacag agttttcagt aatgagtgga cagtaagtgg tggctctgca    3720
gatggcccct ttctaataag tttaataaac ccgaaattac tggttaaaaa aaaaaaaaa    3780 aaaaaaaaaa aaaaa                                                    3795
```

<210> SEQ ID NO 7
<211> LENGTH: 3714
<212> TYPE: DNA
<213> ORGANISM: Homo sapiens

<400> SEQUENCE: 7

```
tcttggacag ctgcgcccag cccttcttca cctgccgtcc aggtatcatc ctagtcttcc      60
ctccgtctct gggatgggaa actcttgtct agtgatgtga ctcattacgt gatcccagac     120
tggaaagttg ttcaagatta tcttgagatc cttgagtttc ctgagttgaa gggaattatt     180
ttcatgcaga cagcttgtca agctgtgcag catcaaagag gcaggagaca gtataacaaa     240
ctgcgaaacc tgctgaagga tgcgcgtcat gattgcattc tctttgctaa tgaattccag     300
caatgctgct atctgccacg ggaaagagga gagtccatgg agaagtggca gaccaggagc     360
atatacaacg cagctgtttg gtactatcat cactgccagg acaggatgcc aattgttatg     420
gtgacagaag atgaagaggc aattcagcag tatggaagtg aaacagaagg agtattcgtg     480
attactttca gaattaccct ggacaatttc tggcctgatt taaaagctgc ccacgagctt     540
tgtgattcta tccttcagtc tcgacgggag agagagaatg agagtcagga gagccatggg     600
aaggagtacc cagaacatct tcccctggaa gtgttagaag ctgggattaa atctggacgc     660
tatatccagg gaattctgaa tgtcaacaaa cacagagccc aaatagaagc ttttgttcga     720
cttcaaggag ccagcagtaa agattcgat ttagtcagtg acatcctaat ccacgggatg     780
aaggctcgaa accgctcaat tcatggagat gtggtagttg tggagctgct tcctaaaaat     840
gaatggaaag gaagaaccgt agccctgtgt gagaatgact gtgacgacaa ggcttcgggc     900
gagtccccaa gtgagcccat gcctacaggt cgagtggtgg gcatacttca aagaactgg     960 cgggattatg tggtgacatt tccgtccaaa gaagaggtcc aatctcaggg caaaaatgct    1020
cagaaaatcc tggttacacc ttgggattac agaattccca aaattcgaat tagcactcag    1080
caagcagaaa ccctccagga cttcagggtg gtcgtgcgca tcgattcctg ggagtcaaca    1140
tctgtgtatc caaatggaca ttttgtgcgt gttttaggaa gaatcggaga tctggaaggg    1200
gaaattgcaa ccatcctggt ggaaaacagt atttcagtta ttcctttctc agaagctcag    1260
atgtgtgaga tgccagtaaa cacaccagaa agtccctgga aggtgagtcc tgaagaggaa    1320
caaaaacgta aagacttgag gaaaagccat ctcgtattca gcattgaccc caaaggttgt    1380
gaagatgtgg atgacacact ctcagtcaga accttaaata tggcaacct ggaacttggg    1440 gtccacatcg cagatgtaac acactttgtg gcaccaaatt cttacattga tattgaagct    1500
agaacaaggg ccaccactta ttatctagca gatcgtcgct atgacatgct gccttccgtc    1560
```

```
ctcagtgcag atttgtgttc ccttctggga ggcgttgata ggtatgctgt aagcatcatg   1620
tgggaactgg ataaagcctc ttatgaaatt aagaaagtgt ggtatggcag aaccattatt   1680
cgatcagcat acaaactgtt ctatgaagca gcccaagaac tactggatgg aaacttaagc   1740
gttgttgatg atattccaga attcaaagac ttggatgaga agagcagaca agccaagctg   1800
gaggagttgg tgtgggcaat tggaaagctg accgacatag ctcgccatgt cagagctaaa   1860
cgagacggat gtggtgccct ggaactggaa ggggtagagg tttgcgtaca gctagatgac   1920
aaaaagaaca ttcacgacct catccccaag cagcccctgg aagtccacga cagtggct     1980 gaatgcatga tcctggccaa ccactgggtc gccaaaaaga tctgggagag cttccctcat   2040
caggccttgc tgcgccagca ccctcctcca caccaggagt tcttttcaga actccgggaa   2100
tgtgctaaag ccaaaggctt cttcatagat acacggtcca ataaacact ggctgattct    2160 ctggataatg cgaacgaccc ccacgatccc attgtgaaca ggctactgcg ctccatggcc   2220
acgcaggcca tgtcgaatgc tctgtacttc tccaccggat cctgtgcgga ggaggagttc   2280
catcattacg gtcttgcatt agataaatat acccacttta cttctccaat aagaagatat   2340
tcagatattg tagtacaccg cttgttaatg gcagccattt caaaagataa gaaaatggaa   2400
attaagggaa atctgttcag caacaaagat cttgaggaat tatgcagaca tatcaacaac   2460
agaaaccaag cagcacagca ttctcagaag cagtctactg agctcttcca gtgcatgtac   2520
ttcaaagaca aagaccctgc caccgaggag cgttgcatat ctgacggagt tatttattca   2580
attagaacaa atggtgtgct tctatttata ccaaggtttg ggattaaagg tgctgcttat   2640
ctaaaaaata aagatggttt agtcatctca tgtggcccag atagctgttc tgaatggaaa   2700
ccaggatccc ttcaacgatt tcaaaacaaa attacctcta ctacaacaga tggggaatct   2760
gttacgttcc atttgtttga ccatgtaacc gtaagaatat ccatacaggc ctcacgttgc   2820
cattctgata caatcagact tgaaataatt agtaacaaac catacaagat accaaataca   2880
gaacttattc atcagagttc ccccttgctg aagagtgagt tagtgaaaga agtaactaaa   2940
tctgtggaag aagctcagct tgcccaagaa gtcaaagtaa acatcattca ggaggaatat   3000
caagaatatc gccaaacaaa gggaaggagc ctatacacac ttctagagga gatacgggac   3060
ctagctctcc tggatgtttc aaacaattat ggaatatgag aggctcttac ttcactaaga   3120
gctgtcatat gtgaatgttt tacagtcttt tcaaacttaa catttaatgt gtgtcactca   3180
gtgctctagt cgatcaggac tgggtagcta tttcgcatat atgtaaaatg ttctcagccg   3240
ggcacggtgg ctcacgcctg taaccccagc actttgggag gctgaggcgg gcggatcacg   3300
aggtcaggag attgagacca tcctggctaa cacggtgaaa cccagtctct actaaaaata   3360
caaaaattag cccggcgtgg tggcatgcgc ctgtagtccc agctacttgg gaggctgaag   3420
caggagaatt gcctgaaccc aggaagagga ggttgcagtg agccgagatc gcaccactgc   3480
attccagcct gggcaacaga gcgagactcc atctcaaaaa aaaaaaaaaa aaaaaaaaa    3540 gttctctcat tcattaaagt tgcattaaat aaagtataat taggtcacta tggaaacaga   3600
gttttcagta atgagtggac agtaagtggt ggctctgcag atggcccctt tctaataagt   3660
ttaataaacc cgaaattact ggttaaaaaa aaaaaaaaaa aaaaaaaaa aaaa          3714
```

<210> SEQ ID NO 8
<211> LENGTH: 2834
<212> TYPE: DNA
<213> ORGANISM: Homo sapiens

<400> SEQUENCE: 8

```
gtctcctcgg ccgacaagct ctcgcgagac gagccgtgca ggctgaaaaa atggcgccac    60
ccagtacccg ggagcccagg gtcctgtcgg cgaccagcgc aaccaaatcc gacggagaga   120
tggtgctgcc aggcttcccg gacgccgaca gctttgtgaa gtttgctctt gggtccgtgg   180
tggcagtcac caaggcatct gggggcctac acagtttgg cgatgagtat gatttttacc   240
gaagttttcc tggcttccaa gcattttgcg aaacacaggg agacaggttg cttcagtgca   300
tgagcagagt aatgcagtac catgggtgtc gcagcaacat taaggatcga agtaaagtga   360
ctgagctgga agacaagttt gatttactag ttgatgccaa tgatgtaatt ctggagagag   420
tgggtatttt actggatgaa gcctcaggtg taaacaagaa tcaacagcct gtcctccctg   480
ccggcttgca ggtccccaaa acggtagtgt ccagctggaa ccgtaaggca gcagaatatg   540
gcaaaaaagc aaaatctgaa actttccggc tgcttcatgc aaaaaatatc atccgacctc   600
agctcaagtt tcgagagaag attgacaatt ccaacacacc atttcttcct aaaatcttca   660
tcaaacccaa tgctcagaaa cctctcccct aagctctctc taaggaaagg cgggaacgcc   720
cacaggatcg tcctgaggac ttggacgtcc cccctgcact ggctgatttc atccatcagc   780
agagaaccca gcaggttgag caagacatgt ttgcacatcc ttatcaatat gaactaaatc   840
actttacccc agcagatgca gtgcttcaaa agccacaacc ccagttatac agacctatag   900
aagagacacc atgccatttc atatcctccc tggatgaact cgtggaactc aacgaaaagc   960
tcttgaattg tcaggaattt gcagttgact ggagcacca ctcttacagg agcttcctgg  1020
gactgacctg cctgatgcaa atttctactc ggacggaaga cttcatcatt gacaccctcg  1080
agcttcgaag tgacatgtac attctcaatg agagcctcac agacccagcc atcgttaagg  1140
tctttcatgg tgctgattca gacatagaat ggctacagaa agactttggg ttgtatgtag  1200
taaacatgtt tgatactcat caggcagcac gccttcttaa cctgggcagg cactcactcg  1260
atcatctcct gaaactctac tgcaacgtgg actcaaacaa gcaatatcag ctggctgatt  1320
ggagaatacg ccctctgccc gaggagatgc tcagctacgc ccgggatgac acccattacc  1380
tgctatatat ctatgacaaa atgaggctgg agatgtggga gcgcggcaac gggcagccgg  1440
tgcagctgca ggtggtgtgg caacggagca gggacatctg cctcaagaaa ttcatcaaac  1500
ctatcttcac ggatgagtcc taccttgaac tctataggaa gcagaagaag caccttaaca  1560
cacagcagtt gacagccttt cagctgctgt ttgcctggag ggataaaaca gctcgcaggg  1620
aagatgaaag ttacggatat gtactgccaa accacatgat gctgaaaata gctgaagaac  1680
tgcctaagga acctcagggc atcatagctt gctgcaaccc agtaccgccc cttgtgcggc  1740
agcagatcaa cgaaatgcac cttttaatcc agcaggcccg agagatgccc ctgctcaagt  1800
ctgaagttgc agccggagtg aagaagagcg gaccgctgcc cagtgctgag agattggaga  1860
atgttctctt tggaccctca gactgctccc atgcccctcc ggatggctat ccaatcatcc  1920
caaccagtgg atctgtgcca gttcagaagc aggcgagcct cttccctgat gaaaagaag  1980
ataacttgct gggtaccaca tgcctgattg ccacagctgt catcacgtta tttaatgaac  2040
ctagtgctga agacagtaaa aagggtccat tgacagttgc acagaaaaaa gcccagaaca  2100
tcatggagtc ctttgaaaat ccatttagga tgtttctgcc ctcactggga caccgtgctc  2160
ccgtctctca ggcagcgaag ttcgatccat caaccaaaat ctatgaaatc agcaaccgct  2220
ggaagctggc ccaggtacaa gtacaaaaag actctaaaga agctgtcaag aagaggcag  2280
ctgagcaaac agctgcccgg gaacaggcaa aggaggcgtg caaagctgca gcagaacagg  2340
```

```
ccatctccgt ccgacagcag gtcgtgctag aaaatgctgc aaagaagaga gagcgagcaa    2400
caagcgaccc aaggaccaca gaacagaaac aagagaagaa acgactcaaa atttccaaga    2460
agccaaagga cccagagcca ccagaaaaag agtttacgcc ttacgactac agccagtcag    2520
acttcaaggc ttttgctgga aacagcaaat ccaaagtttc ttctcagttt gatccaaata    2580
aacagacccc gtctggcaag aaatgcattg cagccaaaaa aattaaacag tcggtgggaa    2640
acaaaagcat gtcctttcca actggaaagt cagacagagg cttcaggtac aactggccac    2700
agagatagtc ctggaagaca cgtggcgcct gtggaccgga agcaccaaat gctggtgctg    2760
cttttgtaca tacatatttt taaaccatta aaattcttcc tgaagaaaaa aaaaaaaaa    2820 aaaaaaaaaa aaaa                                                       2834
```

<210> SEQ ID NO 9
<211> LENGTH: 1282
<212> TYPE: DNA
<213> ORGANISM: Mus musculus

<400> SEQUENCE: 9

```
cctgtgcact ggcttcaccc ctcgcgccgt gcagagcagc catctaagga tgcccggcgc     60
cgtggagggt tttagggtca ccccctttc atctcgtgcg cctgcgtgtg tgtgggagtg    120
tgttcgtgca caagcgcgcg ggcccgtggg accccgcgag attggcgact agcgggacgc    180
tcggggtggc cggagctggc gttaatgcct cgggcgcagg aacacggtag ctgcacttcc    240
ctaacccagg atccctccga gtgccctggg ctggaggcac gcctggcgac cggagggcgc    300
aggcgcggag ggctgcgcag gcgcagagcg ggccggaaaa atggcggctg ggttcaaaac    360
tgtggagccg ctggagtatt acaggagatt tctgaaggaa aactgccgtc ctgatggaag    420
agaacttggt gaattcagag ccacaactgt caacataggt tcaatcagta cagcggatgg    480
ctctgctctc gtgaagctgg ggaataccac ggtcatttgt ggcgttaaag cagaatttgc    540
agcaccacca gtagatgccc ccgatagagg atatgtcgtg tttctttcag tccctaatgt    600
ggatctacca ccgctgtgtt cttcgaggtt ccggacagga cctcctgggg aagaggctca    660
agtaaccagc cagttcattg cagatgtcgt tgacaactca caggtgatta agaaagagga    720
tttatgcatt tctccaggca agcttgcttg ggttctatac tgtgacctca tttgtctaga    780
ctacgatggg aacattttgg atgcctgcac atttgctttg ttagcagctt taagaatgt    840 acagttgcct gaagttacta taaacgaaga gactgcttta gccgaagtca atttaaagaa    900
gaaaagttat ttgaatgtta gaacaaaccc agttgctact tcctttgctg tgtttgatga    960
cactctactg atagtcgatc ctaccggcga ggaggagcac ctgtccacag gaaccctaac   1020
cgtagtcacg gacgaggacg gcaagctgtg ctgtcttcac aagccaggtg ggagtgggct   1080
gactggagct aaacttcagg actgcatgag tcgagcggta acgagacaca aagaagtgag   1140
caagctactg gatgaagtaa ttcagagcat gagacacaaa tgaacagaca ccacgactgc   1200
aaaacagctg taaaaattgt atttgttaca ctgcacaggc tttttatact aaataaatac   1260
ctaattccat tctttgaaag at                                            1282
```

<210> SEQ ID NO 10
<211> LENGTH: 1622
<212> TYPE: DNA
<213> ORGANISM: Mus musculus

<400> SEQUENCE: 10

```
gacgtcggtt ttccgcgccg ggaagaagcc ggtgtgcgga cttgtctcgg tgccgttcat      60
cctttgcgtg gcccgccact atgaaggaga cgccgctttc caactgtgag cgccgcttcc     120
tgctccgcgc aattgaggag aagaagcgcc tggacggcag acagacctat gattacagga     180
acatcaggat ctcattcgga acggattatg gatgctgtat tgtggaactg ggaaaaacaa     240
gagtccttgg acaggtttcc tgtgaacttg tttctccgaa actcaatagg caacggaag      300
gtatcctctt ttttaacctt gagctttctc agatggctgc tccagctttt gagcctggca     360
ggcagtcaga tctcttggtg aagctgaatc gactcttaga aaggtgtcta cgaaattcaa     420
agtgtataga cactgaatct ctctgtgttg tcgctggtga aaaggtttgg cagatccgtg     480
tagacctaca tttattaaat catgatggga atattattga tgctgctagc attgctgcaa     540
ttgtagcctt gtgtcacttc cgaagacctg atgtctctgt ccaaggagag gaagtaacac     600
tgtataccc tgaagagcgt gatcccgtgc cattgagcat ccaccatatg cccatttgtg      660
tcagttttgc tttctttcag caaggaacat acttattggt ggaccccaat gaacgtgaag     720
aacgagtaat ggatggcttg ctggtgattg ccatgaataa gcatcgagaa atttgtacta     780
ttcagtctag tggtgggata atgctgctta aagaccaggt tttcagatgc agtaaaatag     840
ctggtgtgaa agtagcagaa atcacagagc taatacagaa agctttggaa atgaccaga      900
gagtcaggaa agaaggtgga aaatttggct ttgcagagtc tatagcaaac caagaatca      960
cagcgtttaa aatggagacg gcccctattg atacctccaa catagaggag agagcagaag    1020
aaattattgc tgaagctgaa cctcccccag aagttgtttc tcaacctgtg ctgtggactc    1080
ctggaactgc ccagattgga gacggaatag aaaactcctg gggtgacctt gaagattctg    1140
agaaggaaga ggaagaggag gaaggtggca ttgatgaagc tgtcattctt gatgatacaa    1200
agatggcac tggagaagtt tctgatattg ggagtcaagg tgcccctata gtgctatcag     1260
atagtgaaga agaagaaatg attatttttgg agccagagaa gaacccaaag aaaataagag    1320
ctcagaccag tgcaaaccag aaggcaccaa gtaaaggcca agggaaaagg aagaagaaga    1380
agagaactgc taactaagct aaagtggtgg atctctgtgt gtgtgtgtgt gtatacatac    1440
tcagtgctaa cagctctggg tatcttacaa gctgaacttc ttgatacact gtttgtcttt    1500
aacattatgc tttgaataaa ctttctggaa aacttttctg ttgcacaagc ttcccaactc    1560
atgtaagacc ttatttgtta aagttgataa ataaaatgtc tccataaact actgtaaaaa    1620
aa                                                                   1622

<210> SEQ ID NO 11
<211> LENGTH: 3722
<212> TYPE: DNA
<213> ORGANISM: Mus musculus

<400> SEQUENCE: 11
gagagtgacc tcaccagcca gcgggcaaaa gcgggaatgc gcgtggccgc gcctcggttt      60
cttagctgac ggccgggatc ccacgccgcg aggcgagatg ctcaggtcca agacgttctt     120
gaagaagacc cgcgcgggcg gcgtggtgaa gatcgtgcgc gagcactacc tgcgggatga     180
catcggctgc ggcgcgccgg cttgctcggc ctgcggcggg gcgcacgcgg gcccggccct     240
ggagctgcag ccccgggacc aggcgagcag cctctgcccg tggccgcact accttctgcc     300
ggacaccaat gtgctgctgc accagattga tgtcctcgaa cacccggcca tcagaaatgt     360
cattgtgcta caaacagtga tgcaagaagt gagaaaccgg agcgccccca tctacaagcg     420
aatcagggat gtgaccaata accaggaaaa gcatttctat accttcacta atgagcacca     480
```

```
taaagaaacc tacatcgagc aagagcaggg agagaatgcc aatgacagga atgacagagc      540
catccgagtc gcagcgaagt ggtacaacga gcacctgaag agggtggcag cagacagtca      600
gctgcaagtt atcctgataa ccaatgacag gaagaacaaa gagaaagctg tgcaagaggg      660
gataccagcc ttcacgtgtg aagaatacgt aaagagcctg actgctaacc ctgaacttat      720
agaccgtctt gcttacttgt ccgatgaaat gaatgaaata gaaagtggga aataatatt       780 ttcagagcat cttcccttaa gcaagctcca acaaggcata aaatctggtt cctatcttca      840
aggaacattc agagctagca gggaaaatta tttggaggct acagtatgga ttcatggaga      900
caaagaagag gaaaaagaga tacttataca gggaattaag catctaaaca gagctgtgca      960
tgaagacatt gtggccgtgg agctactgcc caggagccag tgggtggcac cgtcttccgt     1020
ggttttagac gatgaaggtc aaaatgaaga cgatgtggag aaagatgagg agagagaact     1080
cctgcttaag actgctgtaa gtgaaaaaat gttacggcct acaggtcgag ttgtggggat     1140
aataaaaagg aactggagac cgtattgtgg catgcttttcc aagtctgata ttaaggagtc     1200
aagaagacat ctctttacac ccgctgataa agaattcca cgaattcgga tagaaaccag      1260
acaggcttct gcgttagaag gacggagaat tattgtcgct attgatggtt ggcctagaaa     1320
ttctagatat ccaaatggac actttgtaaa gaatttaggc gatgttggag agaaggagac     1380
agaaacggaa gtgttgctgc tcgagcacga tgttcctcat cagccctttt cccaggctgt     1440
gcttagcttc ctgcccagga tgccctggag cattactgag gaggacatga aaaaccgaga     1500
agacctgaga catctgtgtg tttgcagtgt ggaccctcca gggtgcactg acatagatga     1560
cgctctgcat tgtagagagc tcagcaatgg aaacttggag gttggtgttc atattgcgga     1620
tgttagccat tttatcaggc caggaaatgc gttggatcaa gaatctgcaa gaagaggaac     1680
aactgtttat ctttgtgaaa agaggattga catggttcca gagttgctca gctccaacct     1740
ctgttcctta agatccaacg ttgacaggtt ggcattttcc tgtatttggg aaatgaatca     1800
taatgctgaa atattaaaaa cgagatttac caaaagtgtc attaattcaa aggcttctct     1860
tacgtacgcg gaagcacaga tgagaattga ttcggcggct atgaatgatg atattaccac     1920
tagtctccgt ggactcaatc agctggctaa aattctaaaa aagggaagga ttgaaaaggg     1980
ggctttgact ctgtcttctc cagagatccg attccacatg gacagtgaaa cccacgaccc     2040
aatcgacctg cagacgaaag agctgagaga acaaattcc atggtggaag aatttatgtt      2100
acttgctaat atttctgtcg caaaaaaaat tcatgaagag ttttctgaac atgctctgct     2160
tcggaaacac ccagctccgc ctccctcgaa ttatgacatt cttgttaagg ctgcaaagtc     2220
caagaatttg caaattaaga ctgatacagc caaatctttg gccgactctt ggaccgggc      2280 tgaatctccg gatttcccat acctgaatac tctattaagg atactggcca ctcgctgtat     2340
gatgcaagct gtgtacttct gctctgggat ggataatgat tttcatcact atggcttagc     2400
ctcccccata tacacacatt tcacctctcc tatcagaaga tatgcagaca taattgtcca     2460
tcggctatta gctgtggcga ttggggctga ctgtacttac cctgagttga cagacaaaca     2520
caagctttca gatatatgta aaaacctcaa tttccggcat aaaatggctc agtatgccca     2580
gcgtgcttcg gtggcttttc atacacagtt gttttttcaaa agcaaaggaa tagtaagtga     2640
agaagcctat attctctttg taaggaaaaa tgcaattgtg gtgttaattc caaagtatgg     2700
cttagaaggt acagttttct ttgaagaaaa agataaaacca aagccacgcc ttgcttacga     2760
tgatgagatc ccttccctga aatagaagg tacagtgttc catgtgtttg ataaggttaa     2820
```

```
agtgaagatc acattagatt catcaaatct tcaacatcag aaaatccgca tggcccttgt    2880
agaaccacag atcccaggaa taaatattcc tcctaatgtt gcagacaagg ctcttactgc    2940
accaggggga agaagagga agcttgagaa gtagctacgt tcaacagaac atccaaagac    3000
tcaacagcaa caaatggag agcatactta cagactcctg tgcgatagct acttttaaat    3060
acatttcaat aattttaaca aatttgcatt tttattgagt tgctgactga atctatctta    3120
tactgtgctt ctgcaacaac aaaaattatg cagaaaaatt catttgaata tccatcactt    3180
aaatggtgac aataacaact tcagagatct gtgatgatca tttaaatgga gtactcatct    3240
tctcatagaa gagccgatta atattatcta agtactttag tagaaaacaa cctgtcaatt    3300
tctgaggaaa ataacatttt agaagcaaag aacaagcctt tctaaatctt cagctgtcag    3360
cgtttggcat ttaatctttt tgccatttta atttgcctac ttacattgtg ttcatatatt    3420
ttgaaaagac ttctctactt taccgtggtc ctccgttgtg agtgttgcag ggctatagga    3480
agacaaagcc tggggtaccc gcatctggtt tggaaccctg agttttgttg ttcagtcagc    3540
agccctagtc atggttgcca atagttttcc caagcaaggc gtcaccgagg aggaagaaag    3600
ggggtactct catgtctgct tactcacaaa aacagatagt ggcttaggaa ttgtggttat    3660
atccagttat acaggcgagg aggggctgtg gtaaagacag attaaaagga acaaatgaag    3720
tc                                                                  3722

<210> SEQ ID NO 12
<211> LENGTH: 3575
<212> TYPE: DNA
<213> ORGANISM: Mus musculus

<400> SEQUENCE: 12
gtgaacgctg ctgcctgccc gaccaggccc gaggggcggg cctcaggcct cggtctcgcc      60
tgagcctgcc gcctgccgcc cgccgcccgc cgcttcccgg ccacagtgcc gggcgacgcc     120
gccagcatgc tgcagaagcg ggagaaggtg ctgctgctga ggaccttcca gggtcggacg     180
ctgcggatcg tgcgtgaaca ctacctgcgg cccagcgtgc cttgcaacag cccgctgtgc     240
ccgcagcctg ccgcctgccg caacgatggg aagctcctgg ctgccgaagt cactcattac     300
gtgatcccag actggaaagt tgtccaggat tacctcgagg ttctggagtt cccggagttg     360
aagggagtta ttttcatgca aacggcctgt caagctgtgc agcaccagag aggccggaga     420
cagtataaca aactgcgaaa cctcctgaag gatgctcgcc atgactgcgt tctctttgct     480
aacgagttcc agcagcactg ttacctcccc cgggaaaagg gggaagccat ggagaagtgg     540
cagaccagga gcatatacaa ctcagcggtt tggtactatc accactgtga ggacaggatg     600
cccatcgtta tggtgacaga agatgaagag gccattcaga agtatggaag tgaaacagaa     660
ggcgtatttg tcatttcttt caagaattac ctggacaact tctggccaga tttgaaggct     720
gcccacgatc tctgtgactc catccttcag tctcgccggg aaagggagac tgagagtcag     780
gaaacccatg ggaaagagta cccagaacat cttcccctag aagtactgga agcgggcatc     840
aaatctggac gctacatcca gggaattctg aatgtcaaca agcacagagc tcagattgaa     900
gctttcgttc gcctacacgg agccagcagt aaggactcag gcttggtcag cgacatcctc     960
atccatggct cgaaggctcg gaaccgctcc atccatggag acgtcgtggt ggtggagatg    1020
ctcccccaaa gtgagtggaa agggagaaca gccgccctgg gtgagaacga cagtgatgac    1080
aaggcctcgg gcgagtcccc gagtgagccc atgcccacag gtcgagtggt aggcatcctt    1140
cagaagaact ggcgagatta tgtggtgaca tttccatcca aagaagaggt ccagtctcag    1200
```

```
ggcaaaaatg ctcagaagat cctggttacg ccgtgggatt acagaatccc taagatccgc    1260
atcagcaccc agcaagcaga agccctccag gatttcaggg tggttgtgcg cattgactcc    1320
tgggaggcaa catcagtgta tccaaatgga cattttgtgc gtgtcttagg gagaatcggt    1380
gatctggaag gggagattgc aaccatcctg gtagagaaca gtatctctgt ggtcccctcc    1440
tcagaagccc agatgtgtga gatgccagtg aacacaccag aaaacccttg gaaagtgagt    1500
cccaaagaag agcaagagcg gaaggacctg aggaccaccc acctcgtgtt cagcatcgac    1560
cccaaaggtt gtgaagatgt ggatgacaca ctctcagtca gaaccttgaa taacggcaac    1620
ctggagctgg gggtccacat cgctgacgtc acacactttg tggcccctaa ctcttacatc    1680
gatgttgaag ctagaacgag ggccaccact tactacctag cggaccgtcg ctatgacatg    1740
ctgccttcca tcctcagcgc agacctctgc tccctcctgg gaggcgttga ccggtatgct    1800
gtgtcagtca tgtgggaatt agataaaacc tcttatgaaa ttaagaaggt gtggtacggc    1860
agaaccatta tccgatcagc ttacaaactg ttctacgagg cggcccagga actactggac    1920
ggaaacttca gcattgttga tgatattcca gaacttaaag ccttggacaa gcagagccaa    1980
caggccaaac tagaggagtt agtgtgggca attggaaagt tgacagacat agctcgccac    2040
atccgagcaa agagagaccg ctgtggagcc ttggagctgg aaggggtaga ggttcgagtc    2100
cagctggatg acaagaagaa catccgtgac ctcatcccca agcagcccct ggaggttcac    2160
gagacggtgg ctgagtgcat gatcctagcc aaccactggg tggccaagaa gatctgggag    2220
agcttccccc accaggctct gctgcgccag cacctccac cacaccagga gttttttctca    2280 gagctccggg aatgtgctaa agcaaaaggc ttcttcatag acacacggtc caataaaacc    2340
ctggctgact ctctggatag tgcaaatgac cccaaggacc ccctggtaaa caagctgctg    2400
cgctccatgg ccacccaggc catgtccaac gcgctctact tctctacggg atcctgcgca    2460
gaggaggagt tccatcatta cgggctggcc ttagataaat acacccactt tacctctcca    2520
ataagaagat actcagatat tgtagtacat cggctattaa tggcagccat ttcaaaagac    2580
aagaaaatgg agattaaaga aaatttgttc agcaacaaaa atcttgagga attatgcaga    2640
cacattaaca acagaaaccg agcggcacag cggtctcaga agcagtccac cgagctcttc    2700
cagtgcatgt actttaaaga ccgagatgca gaaactgagg agcgctgcat agctgatgga    2760
gttatttatt ccattagaac aaatggtgta cttgtatttta taccaaggtt tgggattaaa    2820
ggtgctgctt atctgaagaa taaagatagc ttagtgatct cctgtggccc agagggcagc    2880
tctgaatgga agccaggatc cctacaaaga tctcaaaaca agatcatctc taccacagct    2940
ggagggcagt ctgttacatt tcatctattt gaccatgtga cggtaagaat ttctgtccag    3000
gcctcgcgct gccactctga tacaatcagg cttgaaatag taagcaacaa gccatacatg    3060 atcccaaaaca cagaactctg tcaccagagc tccctgctga gagtgagtt agtgaaggaa    3120 gtaacccgat ctgtggagga agcgcagctt gcacaagaag tcaaaggcaa ggtgattcag    3180
gaagagcatc aagaatactg ccagacaaag ggaagaagtc tgtacacact tctggaggag    3240
ataagggacc tagctcttct ggatgtctct gacagttgtg caatgtgaaa tacttccatg    3300
tcattaaaga cctttgtctt aagtggtgta cttttttttc ttcttcctt tcttcttttc    3360 tttcttttgtt gttgttgagg gtttctctgt gtagcccttg ctgtcctgga actcactatg    3420
taaaccaggc tgtccttgaa ttaagaaatc cgcccacctc tgcctcccaa gtgctgggat    3480
taaaggtgtg tgccaccacg cccagctttt ttttttttt aaacacctct tgcctctgtc    3540
```

```
ttcagactgt tgggattaaa gatatatgcc accac                                3575
```

<210> SEQ ID NO 13
<211> LENGTH: 3479
<212> TYPE: DNA
<213> ORGANISM: Mus musculus

<400> SEQUENCE: 13

```
atagccgggc taagtggaag agcctgcagg caccggatgc ttcggttttt ccaggggac       60
ctaagggcgt aggcacctcc tcctttctgc ccgaaaatgc tattggcacc ttactcctga     120
gcgtattacg ctggctggac atttgacatt gcctgctctg ctcctgccaa tgggaagctc     180
ctggctgccg aagtcactca ttacgtgatc ccagactgga agttgtcca ggattacctc      240
gaggttctgg agttcccgga gttgaaggga gttattttca tgcaaacggc ctgtcaagct     300
gtgcagcacc agagaggccg agacagtat aacaaactgc gaaacctcct gaaggatgct      360
cgccatgact gcgttctctt tgctaacgag ttccagcagc actgttacct cccccgggaa    420
aaggggaag ccatggagaa gtggcagacc aggagcatat acaactcagc ggtttggtac      480
tatcaccact gtgaggacag gatgcccatc gttatggtga cagaagatga agaggccatt     540
cagaagtatg aagtgaaac agaaggcgta tttgtcattt ctttcaagaa ttacctggac      600
aacttctggc cagatttgaa ggctgcccac gatctctgtg actccatcct tcagtctcgc     660
cgggaaaggg agactgagag tcaggaaacc catgggaaag agtacccaga acatcttccc    720
ctagaagtac tggaagcggg catcaaatct ggacgctaca tccagggaat tctgaatgtc     780
aacaagcaca gagctcagat tgaagctttc gttcgcctac acggagccag cagtaaggac    840
tcaggcttgg tcagcgacat cctcatccat ggctcgaagg ctcggaaccg ctccatccat    900
ggagacgtcg tggtggtgga gatgctcccc aaaagtgagt ggaaagggag aacagccgcc    960
ctgggtgaga acgacagtga tgacaaggcc tcgggcgagt ccccgagtga gcccatgccc   1020
acaggtcgag tggtaggcat ccttcagaag aactggcgag attatgtggt gacatttcca   1080
tccaaagaag aggtccagtc tcagggcaaa aatgctcaga agatcctggt tacgccgtgg   1140
gattacagaa tccctaagat ccgcatcagc acccagcaag cagaagccct ccaggatttc   1200
agggtggttg tgcgcattga ctcctgggag gcaacatcag tgtatccaaa tggacatttt   1260
gtgcgtgtct tagggagaat cggtgatctg aagggggaga ttgcaaccat cctggtagag   1320
aacagtatct ctgtggtccc cttctcagaa gcccagatgt gtgagatgcc agtgaacaca   1380
ccagaaaacc cttggaaagt gagtcccaaa gaagagcaag agcggaagga cctgaggacc   1440
acccacctcg tgttcagcat cgaccccaaa ggttgtgaag atgtggatga cacactctca   1500
gtcagaacct tgaataacgg caacctggag ctgggggtcc acatcgctga cgtcacacac   1560
tttgtggccc ctaactctta catcgatgtt gaagctagaa cgagggccac cacttactac   1620
ctagcggacc gtcgctatga catgctgcct tccatcctca gcgcagacct ctgctccctc   1680
ctgggaggcg ttgaccggta tgctgtgtca gtcatgtggg aattagataa aacctcttat   1740
gaaattaaga aggtgtggta cggcagaacc attatccgat cagcttacaa actgttctac   1800
gaggcggccc aggaactact ggacggaaac ttcagcattg ttgatgatat tccagaactt   1860
aaagccttgg acaagcagag ccaacaggcc aaactagagg agttagtgtg ggcaattgga   1920
aagttgacag acatagctcg ccacatccga gcaaagagag accgctgtgg agccttggag   1980
ctggaagggg tagaggttcg agtccagctg gatgacaaga gaacatccg tgacctcatc   2040
cccaagcagc ccctggaggt tcacgagacg gtggctgagt gcatgatcct agccaaccac   2100
```

```
tgggtggcca agaagatctg ggagagcttc ccccaccagg ctctgctgcg ccagcaccct    2160
ccaccacacc aggagttttt ctcagagctc cgggaatgtg ctaaagcaaa aggcttcttc    2220
atagacacac ggtccaataa aaccctggct gactctctgg atagtgcaaa tgacccaag    2280 gaccccctgg taaacaagct gctgcgctcc atggccaccc aggccatgtc caacgcgctc    2340
tacttctcta cgggatcctg cgcagaggag gagttccatc attacgggct ggccttagat    2400
aaatacaccc actttacctc tccaataaga agatactcag atattgtagt acatcggcta    2460
ttaatggcag ccatttcaaa agacaagaaa atggagatta agaaaatttt gttcagcaac    2520
aaaaatcttg aggaattatg cagacacatt aacaacagaa accgagcggc acagcggtct    2580
cagaagcagt ccaccgagct cttccagtgc atgtacttta agaccgaga tgcagaaact    2640 gaggagcgct gcatagctga tggagttatt tattccatta gaacaaatgg tgtacttgta    2700
tttataccaa ggtttgggat taaaggtgct gcttatctga agaataaaga tagcttagtg    2760
atctcctgtg gcccagaggg cagctctgaa tggaagccag gatccctaca aagatctcaa    2820
aacaagatca tctctaccac agctggaggg cagtctgtta catttcatct atttgaccat    2880
gtgacggtaa gaatttctgt ccaggcctcg cgctgccact ctgatacaat caggcttgaa    2940
atagtaagca acaagccata catgatccca aacacagaac tctgtcacca gagctccctg    3000
ctgaagagtg agttagtgaa ggaagtaacc cgatctgtgg aggaagcgca gcttgcacaa    3060
gaagtcaaag gcaaggtgat tcaggaagag catcaagaat actgccagac aaagggaaga    3120
agtctgtaca cacttctgga ggagataagg gacctagctc ttctggatgt ctctgacagt    3180
tgtgcaatgt gaaatacttc catgtcatta aagaccttg tcttaagtgg tgtactttt    3240 tttcttctt cctttcttct tttctttctt tgttgttgtt gagggtttct ctgtgtagcc    3300
cttgctgtcc tggaactcac tatgtaaacc aggctgtcct tgaattaaga aatccgccca    3360
cctctgcctc ccaagtgctg gggttaaagg tgtgtgccac cacgcccagc ttttttttt    3420 ttttaaacac ctcttgcctc tgtcttcaga ctgttgggat taaagatata tgccaccac    3479
```

<210> SEQ ID NO 14
<211> LENGTH: 3536
<212> TYPE: DNA
<213> ORGANISM: Mus musculus

<400> SEQUENCE: 14

```
aaagagcaaa gggaatcccg gcctggcgtc gcgatggcgg cggggcccta gtgaaggaag     60
cgggacccaa ggagagagga gagcgggaag ctgagcagcg agggcggctt agcgctggca    120
tcaagggcgg agccagaccc tcgcggactg taggcagccg gagcgagcat aaccgtctgg    180
gctcggcggt actggggcag ccgggagcgg ccctggagcg tccccgatgg gaagctcctg    240
gctgccgaag tcactcatta cgtgatccca gactggaaag ttgtccagga ttacctcgag    300
gttctggagt tcccggagtt gaagggagtt attttcatgc aaacggcctg tcaagctgtg    360
cagcaccaga gaggccggag acagtataac aaactgcgaa acctcctgaa ggatgctcgc    420
catgactgcg ttctctttgc taacgagttc cagcagcact gttacctccc ccgggaaaag    480
ggggaagcca tggagaagtg gcagaccagg agcatataca actcagcggt ttggtactat    540
caccactgtg aggacaggat gcccatcgtt atggtgacag aagatgaaga ggccattcag    600
aagtatggaa gtgaaacaga aggcgtattt gtcatttctt tcaagaatta cctgacaac    660 ttctggccag atttgaaggc tgcccacgat ctctgtgact ccatccttca gtctcgccgg    720
```

-continued

| | |
|---|---|
| gaaagggaga ctgagagtca ggaaacccat gggaaagagt acccagaaca tcttcccta | 780 |
| gaagtactgg aagcgggcat caaatctgga cgctacatcc agggaattct gaatgtcaac | 840 |
| aagcacagag ctcagattga agctttcgtt cgcctacacg gagccagcag taaggactca | 900 |
| ggcttggtca gcgacatcct catccatggc tcgaaggctc ggaaccgctc catccatgga | 960 |
| gacgtcgtgg tggtggagat gctccccaaa agtgagtgga aagggagaac agccgccctg | 1020 |
| ggtgagaacg acagtgatga caaggcctcg ggcgagtccc cgagtgagcc catgcccaca | 1080 |
| ggtcgagtgg taggcatcct tcagaagaac tggcgagatt atgtggtgac atttccatcc | 1140 |
| aaagaagagg tccagtctca gggcaaaaat gctcagaaga tcctggttac gccgtgggat | 1200 |
| tacagaatcc ctaagatccg catcagcacc cagcaagcag aagccctcca ggatttcagg | 1260 |
| gtggttgtgc gcattgactc ctgggaggca acatcagtgt atccaaatgg acattttgtg | 1320 |
| cgtgtcttag ggagaatcgg tgatctggaa ggggagattg caaccatcct ggtagagaac | 1380 |
| agtatctctg tggtcccctt ctcagaagcc cagatgtgtg agatgccagt gaacacacca | 1440 |
| gaaaacccctt ggaaagtgag tcccaaagaa gagcaagagc ggaaggacct gaggaccacc | 1500 |
| cacctcgtgt tcagcatcga ccccaaaggt tgtgaagatg tggatgacac actctcagtc | 1560 |
| agaaccttga ataacggcaa cctggagctg ggggtccaca tcgctgacgt cacacacttt | 1620 |
| gtggccccta actcttacat cgatgttgaa gctagaacga gggccaccac ttactaccta | 1680 |
| gcggaccgtc gctatgacat gctgccttcc atcctcagcg cagacctctg ctccctcctg | 1740 |
| ggaggcgttg accggtatgc tgtgtcagtc atgtgggaat tagataaaac ctcttatgaa | 1800 |
| attaagaagg tgtggtacgg cagaaccatt atccgatcag cttacaaact gttctacgag | 1860 |
| gcggcccagg aactactgga cggaaacttc agcattgttg atgatattcc agaacttaaa | 1920 |
| gccttggaca agcagagcca acaggccaaa ctagaggagt tagtgtgggc aattggaaag | 1980 |
| ttgacagaca tagctcgcca catccgagca aagagagacc gctgtggagc cttggagctg | 2040 |
| gaaggggtag aggttcgagt ccagctggat gacaagaaga acatccgtga cctcatcccc | 2100 |
| aagcagcccc tggaggttca cgagacggtg gctgagtgca tgatcctagc caaccactgg | 2160 |
| gtggccaaga gatctggga gagcttcccc caccaggctc tgctgcgcca gcaccctcca | 2220 |
| ccacaccagg agttttctc agagctccgg gaatgtgcta aagcaaaagg cttcttcata | 2280 |
| gacacacggt ccaataaaac cctggctgac tctctggata gtgcaaatga ccccaaggac | 2340 |
| cccctggtaa acaagctgct gcgctccatg gccacccagg ccatgtccaa cgcgctctac | 2400 |
| ttctctacgg gatcctgcgc agaggaggag ttccatcatt acgggctggc cttagataaa | 2460 |
| tacacccact ttacctctcc aataagaaga tactcagata ttgtagtaca tcggctatta | 2520 |
| atggcagcca tttcaaaaga caagaaaatg gagattaaag aaaatttgtt cagcaacaaa | 2580 |
| aatcttgagg aattatgcag acacattaac aacagaaacc gagcggcaca gcggtctcag | 2640 |
| aagcagtcca ccgagctctt ccagtgcatg tactttaaag accgagatgc agaaactgag | 2700 |
| gagcgctgca tagctgatgg agttatttat tccattagaa caaatggtgt acttgtattt | 2760 |
| ataccaaggt ttgggattaa aggtgctgct tatctgaaga ataaagatag cttagtgatc | 2820 |
| tcctgtggcc cagagggcag ctctgaatgg aagccaggat ccctacaaag atctcaaaac | 2880 |
| aagatcatct ctaccacagc tggagggcag tctgttacat ttcatctatt tgaccatgtg | 2940 |
| acggtaagaa tttctgtcca ggcctcgcgc tgccactctg atacaatcag gcttgaaata | 3000 |
| gtaagcaaca agccatacat gatcccaaac acagaactct gtcaccagag ctccctgctg | 3060 |
| aagagtgagt tagtgaagga agtaacccga tctgtggagg aagcgcagct tgcacaagaa | 3120 |

| | | |
|---|---|---|
| gtcaaaggca aggtgattca ggaagagcat caagaatact gccagacaaa gggaagaagt | 3180 |
| ctgtacacac ttctggagga gataagggac ctagctcttc tggatgtctc tgacagttgt | 3240 |
| gcaatgtgaa atacttccat gtcattaaag acctttgtct taagtggtgt acttttttt | 3300 |
| cttcttcct ttcttctttt ctttctttgt tgttgttgag ggtttctctg tgtagccctt | 3360 |
| gctgtcctgg aactcactat gtaaaccagg ctgtccttga attaagaaat ccgcccacct | 3420 |
| ctgcctccca agtgctgggg ttaaaggtgt gtgccaccac gcccagcttt ttttttttt | 3480 |
| taaacacctc ttgcctctgt cttcagactg ttgggattaa agatatatgc caccac | 3536 |

<210> SEQ ID NO 15
<211> LENGTH: 2803
<212> TYPE: DNA
<213> ORGANISM: Mus musculus

<400> SEQUENCE: 15

| | |
|---|---|
| ccggaacaat ctcgcgagaa gagccgccct aggacggaaa aatggcgcct cccagtcccc | 60 |
| gggagcatca gtccgcgccg gcgaccagtg cgaccaagcc tgacgcggag atggtactgc | 120 |
| ctggcttccc cgatgcagac agcttcgtaa agtttgcact tgggtcggta gtggcagtta | 180 |
| ccaaggcatc cgggggcctg ccacagttcg gtgacgagta tgattttttac agaagtttcc | 240 |
| ctgccttcca ggcattctgt gagacacaag gagacaggtt actgcagtgc atgagtcggg | 300 |
| taatgcagta ccatggctgt cgcagcaaca tcaaagaccg aagtaaagtg actgaattgg | 360 |
| aggacaagtt tgatttatta gtcgatacca atgacgtgat attggagaga gtgggcatgt | 420 |
| tactggatga agcctccggt gtgaacaagc atcagcagcc tgtccttcct gcagggctgc | 480 |
| aggtccccaa aacaatagta tccagctgga tcggaaggc aggagagtat ggcaaaaagg | 540 |
| caaaatcgga gactttccga ctgctgcatg caaaaaacat cgtgcgacct cagctcaggt | 600 |
| ttcgagagaa gatcgacaat tctaacacac catttctccc gaagatcttt gtcaaaccca | 660 |
| atgcccggaa gccactccct ctggctctct caaaagaaag gcgggaacgc ccgcaggacc | 720 |
| gtccggagga cctggatgtc cccccagccc tggcagattt catccatcag cagcgaaccc | 780 |
| agcaggtgga gcaggacatg tttgcacacc cttaccagta tgaactggat cactttactc | 840 |
| cgcctcagtc ggtgctgcag aggccgaagc ccagttgta ccgagctgtg ggagagactc | 900 |
| cctgccactt ggtgtcgtcc ctggatgagc tggtggagct caacgagaag ctcctgggct | 960 |
| gtcaggagtt tgccgtggac ttagagcatc actcttacag aagcttccta ggactcacct | 1020 |
| gcctcatgca gatctccacc cggacagaag acttcattgt cgacaccctc gagcttcgca | 1080 |
| gtgacatgta cattctcaac gagagcctca cggacccagc catcgttaag gtcttccatg | 1140 |
| gtgccgactg tgacattgag tggctgcaga agacttcgg actctatgtg gtgaacatgt | 1200 |
| ttgacacaca ccaggcagca cggcttctca acctggctcg gcactcactc gaccatctgc | 1260 |
| tgagactcta ctgcggtgtg aatcaaaca agcaatatca gctggcagac tggaggatac | 1320 |
| gtcctctgcc agaggaaatg ctgagctacg cccgggatga cacccattac ctgctctaca | 1380 |
| tctatgaccg aatgaggctg gaactgtggg aaagaggcaa ccaccagcct gtccagttgc | 1440 |
| aggtggtttg gcagcggagc agggacatct gcctcaagaa atttgtcaag cctatctta | 1500 |
| cggacgagtc ctacctggag ctctatcgaa agcaaaagaa gcacctgaac tcgcagcagc | 1560 |
| tgaccgcctt ccagctgctg tttgcttgga gggataagac agctcgcagg gaggatgaga | 1620 |
| gctacggata tgttctacca aatcacatga tgctaaagat agctgaggaa ctgcctaagg | 1680 |

```
agcctcaagg catcatagct tgctgtaacc cagtaccacc tcttgtccgg cagcagatca   1740
atgagatgca tctcctaatc cagcaggctc gagagatgcc cctgctcaag tctgaaaatg   1800
cagctggagt gaggaagagc ggaccactgc ctagcgccga gagattggag aatgatctct   1860
ttggacccca tgactgttcc cacgcccctc cagataacta ccagaacacc tcaactgatg   1920
ggaccctgcc acttcagaag cagccaagcc tattcactga gggcaaagaa gagacctctg   1980
tggatgccgg atgcctcctt gccacagccg tcatcactct gttcagtgaa cctaacactg   2040
aggaaggtgg aaagactcca ttgacggtgg cccagaaaaa agcccagaac ataatgcagt   2100
cctttgaaaa cccatttcgg atgttcctgc cttctctgga acacaaggcc cacatctctc   2160
aagcagcaaa gtttgatcct tcttcgaaaa tctatgaaat cagcaaccgc tggaagctgg   2220
ccagccaggt ccaggtccag aaagaaccta agaagcaac caagaagaag gtagctgagc    2280
aaacagctgc ccgggaggag gcgaaggagg aggctgcagc cggtgtgctg gaacaggcta   2340
tccctgtgcg gcagcaggcc gcgctagaaa atgctactaa gaagagagaa cgagccacca   2400
gtgacctgag gactatagag caaaaacagg agaagaaacg actaaaaagc tccaagaaag   2460
ccaaggaccc tgatccccca gggaaagact tcagtcccta tgactacagc cagtcagact   2520
tcagggcctt tgctggggac agtaaatcca agccttcctc ccagttcgac cccaataagc   2580 tggcacttc cggcaagaaa ggtgttggag ccaaaaaatg taaacagtcg gtgggaaaca    2640
aaagcatgtc atttgctgtt ggaaagtcgg acagaggctt ccgccacaac tggccaaaga   2700
gatagtgctg gagggactcc tggggctgcc gacagcgctg ctttgtacac acccatttta   2760
aaaccattaa aatgtattcc taccagaaga aaaaaaaaaa aaa                     2803
```

<210> SEQ ID NO 16
<211> LENGTH: 19
<212> TYPE: RNA
<213> ORGANISM: Artificial Sequence
<220> FEATURE:
<223> OTHER INFORMATION: Exosc8 siRNA

<400> SEQUENCE: 16
gaaagaggau uuaugcauu                                                 19

<210> SEQ ID NO 17
<211> LENGTH: 19
<212> TYPE: RNA
<213> ORGANISM: Artificial Sequence
<220> FEATURE:
<223> OTHER INFORMATION: Exosc8 siRNA

<400> SEQUENCE: 17
caacauaggu ucaaucagu                                                 19

<210> SEQ ID NO 18
<211> LENGTH: 19
<212> TYPE: RNA
<213> ORGANISM: Artificial Sequence
<220> FEATURE:
<223> OTHER INFORMATION: Exosc8 siRNA

<400> SEQUENCE: 18
uggagccgcu ggaguauua                                                 19

<210> SEQ ID NO 19
<211> LENGTH: 19
<212> TYPE: RNA
<213> ORGANISM: Artificial Sequence
<220> FEATURE:
<223> OTHER INFORMATION: Exosc8 siRNA

<400> SEQUENCE: 19
ggaauaccac ggucauuug                                                    19

<210> SEQ ID NO 20
<211> LENGTH: 97
<212> TYPE: DNA
<213> ORGANISM: Artificial Sequence
<220> FEATURE:
<223> OTHER INFORMATION: Exosc8 shRNA

<400> SEQUENCE: 20
tgctgttgac agtgagcgcc aggagatttc tgaaggaaaa tagtgaagcc acagatgtat      60
tttccttcag aaatctcctg ttgcctactg cctcgga                               97

<210> SEQ ID NO 21
<211> LENGTH: 97
<212> TYPE: DNA
<213> ORGANISM: Artificial Sequence
<220> FEATURE:
<223> OTHER INFORMATION: Exosc8 shRNA

<400> SEQUENCE: 21
tgctgttgac agtgagcgac gctggagtat tacaggagat tagtgaagcc acagatgtaa      60
tctcctgtaa tactccagcg gtgcctactg cctcgga                               97

<210> SEQ ID NO 22
<211> LENGTH: 97
<212> TYPE: DNA
<213> ORGANISM: Artificial Sequence
<220> FEATURE:
<223> OTHER INFORMATION: Exosc8 shRNA

<400> SEQUENCE: 22
tgctgttgac agtgagcgcc acaaagaagt gagcaagcta tagtgaagcc acagatgtat      60
agcttgctca cttctttgtg ttgcctactg cctcgga                               97

<210> SEQ ID NO 23
<211> LENGTH: 97
<212> TYPE: DNA
<213> ORGANISM: Artificial Sequence
<220> FEATURE:
<223> OTHER INFORMATION: Exosc9 shRNA

<400> SEQUENCE: 23
tgctgttgac agtgagcgac agattggaga cggaatagaa tagtgaagcc acagatgtat      60
tctattccgt ctccaatctg gtgcctactg cctcgga                               97

<210> SEQ ID NO 24
<211> LENGTH: 97
<212> TYPE: DNA
<213> ORGANISM: Artificial Sequence
<220> FEATURE:
<223> OTHER INFORMATION: Exosc9 shRNA

<400> SEQUENCE: 24
tgctgttgac agtgagcgaa agaagagaac tgctaactaa tagtgaagcc acagatgtat      60
tagttagcag ttctcttctt ctgcctactg cctcgga                               97

<210> SEQ ID NO 25

```
<211> LENGTH: 97
<212> TYPE: DNA
<213> ORGANISM: Artificial Sequence
<220> FEATURE:
<223> OTHER INFORMATION: Dis3 shRNA

<400> SEQUENCE: 25
tgctgttgac agtgagcgcc cacagatccc aggaataaat tagtgaagcc acagatgtaa    60
tttattcctg ggatctgtgg ttgcctactg cctcgga                             97

<210> SEQ ID NO 26
<211> LENGTH: 97
<212> TYPE: DNA
<213> ORGANISM: Artificial Sequence
<220> FEATURE:
<223> OTHER INFORMATION: Dis3 shRNA

<400> SEQUENCE: 26
tgctgttgac agtgagcgac agacagtcag ctgcaagtta tagtgaagcc acagatgtat    60
aacttgcagc tgactgtctg ctgcctactg cctcgga                             97

<210> SEQ ID NO 27
<211> LENGTH: 97
<212> TYPE: DNA
<213> ORGANISM: Artificial Sequence
<220> FEATURE:
<223> OTHER INFORMATION: Dis3L shRNA

<400> SEQUENCE: 27
tgctgttgac agtgagcgcg gccggagaca gtataacaaa tagtgaagcc acagatgtat    60
ttgttatact gtctccggcc ttgcctactg cctcgga                             97

<210> SEQ ID NO 28
<211> LENGTH: 97
<212> TYPE: DNA
<213> ORGANISM: Artificial Sequence
<220> FEATURE:
<223> OTHER INFORMATION: Dis3L shRNA

<400> SEQUENCE: 28
tgctgttgac agtgagcgct acatcgatgt tgaagctaga tagtgaagcc acagatgtat    60
ctagcttcaa catcgatgta atgcctactg cctcgga                             97

<210> SEQ ID NO 29
<211> LENGTH: 19
<212> TYPE: RNA
<213> ORGANISM: Artificial Sequence
<220> FEATURE:
<223> OTHER INFORMATION: Exosc10 siRNA

<400> SEQUENCE: 29
gaaguaaagu gacugaauu                                                 19

<210> SEQ ID NO 30
<211> LENGTH: 19
<212> TYPE: RNA
<213> ORGANISM: Artificial Sequence
<220> FEATURE:
<223> OTHER INFORMATION: Exosc10 siRNA

<400> SEQUENCE: 30
cgauaccaau gacgugaua                                                 19
```

```
<210> SEQ ID NO 31
<211> LENGTH: 19
<212> TYPE: RNA
<213> ORGANISM: Artificial Sequence
<220> FEATURE:
<223> OTHER INFORMATION: Exosc10 siRNA

<400> SEQUENCE: 31
acaguucggu gacgaguau                                                        19

<210> SEQ ID NO 32
<211> LENGTH: 19
<212> TYPE: RNA
<213> ORGANISM: Artificial Sequence
<220> FEATURE:
<223> OTHER INFORMATION: Exosc10 siRNA

<400> SEQUENCE: 32
acggauaugu ucuaccaaa                                                        19
```

COMPOSITIONS AND METHODS TO PROMOTE ERYTHROPOIESIS

CROSS-REFERENCE TO RELATED APPLICATIONS

This application claims priority to U.S. Provisional Application 61/842,569 filed on Jul. 3, 2014, which is incorporated herein by reference in its entirety.

STATEMENT REGARDING FEDERALLY SPONSORED RESEARCH & DEVELOPMENT

This invention was made with government support under HL116365 awarded by the National Institutes of Health. The government has certain rights in the invention.

FIELD OF THE DISCLOSURE

The present disclosure is related to compositions and methods to promote erythropoiesis.

BACKGROUND

Maintenance of an adequate supply of oxygen to the body tissues is necessary for survival. Because the oxygen-carrying capacity of blood is governed by the concentration of erythrocytes in the blood, the appropriate regulation of erythropoiesis, the process by which red blood cells are produced, is critical.

Anemia is generally defined as a decrease in the number of red blood cells or reduced hemoglobin in the blood, and can be caused by decreased erythropoiesis. Anemias associated with aging, infectious disease, chronic renal failure, end-stage renal disease, renal transplantation, cancer, AIDS, antiviral therapy, chronic stress, chemotherapy, radiation therapy, bone marrow transplantation, and of genetic origin generally require therapies to induce erythroid differentiation, and therefore to increase red blood cell output. Currently, erythropoietin (Epo), a glycoprotein hormone that controls erythropoiesis, and its pharmacological derivatives are used to treat anemias such as anemia resulting from chronic kidney disease. However, many anemias are Epo-insensitive. In addition, in certain contexts, Epo treatment has been associated with undesirable side effects such as myocardial infarction, stroke, venous thromboembolism and tumor recurrence. What is needed are novel modes of stimulating erythropoiesis.

BRIEF SUMMARY

In one aspect, a method of enhancing erythropoiesis in an individual in need thereof comprises administering an effective amount of an agent that decreases the expression of Exosc8, Exosc9, DIS3, DIS3L or Exosc10, wherein the agent produces an increase in red blood cell production in the individual.

In another aspect, a pharmaceutical composition comprises a pharmaceutically acceptable excipient and a small interfering RNA that reduces or inhibits the expression of Exosc8 (e.g., SEQ ID NO. 1 or 9), Exosc9 (e.g., SEQ ID NO. 2, 3 or 10), Dis3 (e.g., SEQ ID Nos. 4, 5 or 11), Dis3L (e.g., SEQ ID NOs. 6, 7, 12, 13, or 14), or Exosc10 (e.g., SEQ ID NO. 8 or 15).

BRIEF DESCRIPTION OF THE DRAWINGS

FIG. 37 shows the name and function of genes in "cell cycle arrest" category derived from GO term analysis from GATA-1-activated and Exosc8-repressed genes.

FIG. 38 shows quantitative real-time RT-PCR analysis of genes in "cell cycle arrest" category upon Exosc8 or Exosc9 knockdown in primary murine erythroid precursor cells under expansion conditions (mean+/−SE; 6 independent experiments). Values were normalized to 18S rRNA and the expression is shown relative to the control shRNA.

Figure 1:
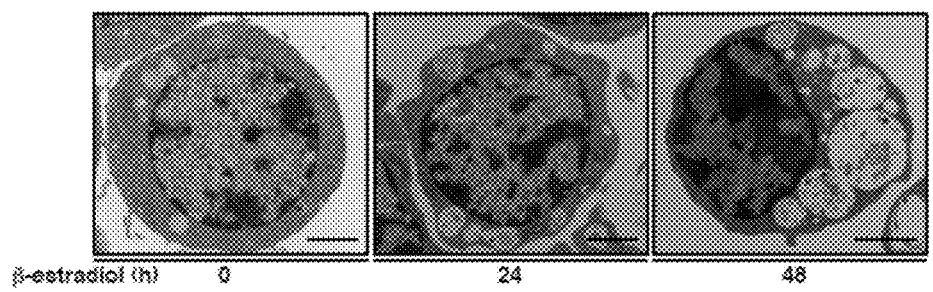
FIG. 1 shows representative TEM pictures of G1E-ER-GATA-1 cells with or without β-estradiol treatment. Scale bar, 2 μm.

The above-described and other features will be appreciated and understood by those skilled in the art from the following detailed description, drawings, and appended claims.

DETAILED DESCRIPTION

Hematopoietic stem cells give rise to lineage-committed progenitors that differentiate into erythroid precursors termed erythroblasts. Erythroblasts undergo sequential maturation steps, culminating in enucleation to yield reticulocytes and subsequently erythrocytes. A restricted cohort of transcription factors, including GATA-1, KLF1, and SCL/TAL1 are responsible for establishing and maintaining the expression of genes that endow the red cell with its unique identity. The present inventors previously established that that the Forkhead transcription factor Foxo3 amplifies GATA-1-mediated transcriptional activation of genes encoding components of the autophagy machinery. The Forkhead transcription factor Foxo3 is essential for regulating oxidative stress response genes in erythroblasts. GATA-1 directly upregulates Foxo3 expression, which in turn, amplifies GATA-1 activity to regulate autophagy gene expression.

Autophagy is the catabolic mechanism of cell degradation of cellular components through the lysosomal machinery. Autophagy mediates cellular quality control and organelle remodeling, including the consumption of mitochondria, as a critical determinant of physiological and pathological processes. A unique cellular structure, the autophagosome, engulfs damaged or aged organelles, such as mitochondria, and long-lived proteins. Following the regulated fusion of an autophagosome to a lysosome, components within the autophagosome are degraded.

Autophagy is essential for multiple aspects of hematopoiesis, from hematopoietic stem cell maintenance to the formation of specific blood cell types. Nucleated erythroid precursor cells undergo sequential maturation steps culminating in erythroblast enucleation to yield reticulocytes and subsequently erythrocytes. Autophagy-dependent disposal of mitochondria (mitophagy) is a critical component of the erythroid maturation process.

Previously, the present inventors described a function of the master regulator of erythropoiesis GATA-1 to transcriptionally upregulate genes encoding essential autophagy components. Dissecting how GATA-1 instigates autophagy, the inventors discovered that GATA-1 and the forkhead transcription factor Foxo3 function combinatorially in a feed-forward loop to repress expression of a key component of the exosome complex. The exosome complex mediates degradation of aberrant pre-mRNAs and mRNAs and is required for the processing and degradation of pre-rRNAs, pre-snRNAs, and pre-tRNAs. In addition to mediating RNA degradation, the exosome complex controls gene expression via regulating transcription start site usage, maintaining the heterochromatin mark H3K9 methylation, and regulating expression of non-coding RNAs. A recent study revealed exosome complex and chromatin insulator component co-occupancy at boundary elements and promoters in *Drosophila*. While the exosome complex is implicated in diverse molecular processes, whether its functions contribute to or orchestrate specific biological processes is largely unexplored.

Specifically, through analyzing genetic networks regulated combinatorially by both GATA-1 and the forkhead protein FOXO3, the present inventors discovered a feed-forward loop that promotes autophagy. GATA-1 induced FOXO3 expression, and GATA-1 and FOXO3 co-occupied and regulated autophagy genes. Genomic analysis of the GATA-1/FOXO3 target gene ensemble revealed GATA-1/FOXO3-dependent repression of Exosc8 (Rrp43), which encodes a pivotal component of the exosome that mediates RNA surveillance and epigenetic regulation. Strikingly, using shRNA to reduce Exosc8 or Exosc9 (Rrp45) expression in primary erythroid precursor cells induced autophagy and erythroid cell maturation. The exosome consists of nine essential core subunits and two catalytic subunits. The inventors knocked down Exosc8, Exosc9 and catalytic subunits, Dis3 (Rrp44), Dis3L and Exosc10 (Rrp6). Knocking down Dis3, Dis3L and Exosc10 had qualitatively similar but quantitatively reduced results as knocking down Exosc8 on red blood cell maturation.

More specifically, loss-of-function analysis revealed a mechanism in which the exosome components Exosc8 and Exosc9 create a blockade to primary erythroid cell maturation. Disruption of this blockade induced spontaneous erythroid maturation to yield late-stage erythroblasts and reticulocytes. The exosome complex had not been linked to hematopoiesis or erythroid cell biology, and therefore the results establish important biological functions for the exosome complex.

In one aspect, the inventors of the present application have discovered that reducing the levels of cellular RNA processing components of the RNA processing nuclear exosome (EXOSC8 and EXOSC9) stimulate the erythroid differentiation of primary erythroid cells. This finding has also been demonstrated with an erythroid cell line that mimics the normal physiology of primary erythroid cells. This stimulation of differentiation does not involve altered levels of the master regulator of erythropoiesis, GATA-1. The enhanced maturation was demonstrated using 1) RNA expression that provides a read-out for maturation and 2) Flow cytometric evaluation of erythroid surface protein expression that provides a read-out for maturation. Enhanced maturation was also demonstrated using morphology and cell cycle analysis. This molecular and cell biological evidence provides extremely strong evidence that lowering the levels of EXOSC8, EXOSC9, DIS3, DIS3L and EXOSC10 strongly induces erythroid maturation, promoting erythropoiesis.

In one embodiment, a method of enhancing erythropoiesis in an individual in need thereof comprises administering an effective amount of an agent that decreases the expression and/or activity of Exosc8, Exosc9, Dis3, Dis3L or Exosc10, wherein the agent produces an increase in red blood cell production in the individual.

As used herein "decreases" means a reduction of at least 5% relative to a reference level. A decrease may be by 5%, 10%, 15%, 20%, 25% or 50%, or even by as much as 75%, 85%, 95% or more.

As used herein "increases" means a stimulation of at least 5% relative to a reference level. An increase may be by 5%, 10%, 15%, 20%, 25% or 50%, or even by as much as 75%, 85%, 95% or more.

An "effective amount" is the amount of an agent required to ameliorate the symptoms of a disease or slow, stabilize, prevent, or reduce the severity of the pathology in a subject relative to an untreated subject. The effective amount of active agent(s) varies depending upon the manner of administration, the age, body weight, and general health of the subject. Ultimately, the attending physician or veterinarian will decide the appropriate amount and dosage regimen. Such amount is referred to as an "effective" amount.

The sequences of Exosc8, Exosc9, Dis3, Dis3L and Exosc10 are known in the art. Human Exosc8 has accession number NM_181503.2 (SEQ ID NO. 1); human Exosc9 has 2 transcript variants, Exosc9 variant 1 has accession number NM_001034194.1 (SEQ ID NO. 2), Exosc9 variant 2 has accession number NM_005033.2 (SEQ ID NO. 3); human Dis3 has 2 transcript variants, Dis3 variant 1 has accession number NM_014953.4 (SEQ ID No. 4), Dis3 variant 2 has accession number NM_001128226.2 (SEQ ID No. 5); human Dis3L has 2 transcript variants, Dis3L variant 1 has accession number NM_001143688.1 (SEQ ID No. 6), Dis3L variant 2 has accession number NM_133375.3 (SEQ ID No. 7); and human Exosc10 has accession number NM_001001998.1 (SEQ ID NO. 8). Mouse Exosc8 has accession number NM_001163570.1 (SEQ ID NO. 9); mouse Exosc9 has accession number NM_019393.2 (SEQ ID NO. 10); mouse Dis3 has accession number NM_028315.2 (SEQ ID No. 11); mouse Dis3L has 3 transcript variants, Dis3L variant 1 has accession number NM_001001295 (SEQ ID No. 12), Dis3L variant 2 has accession number NM_172519.3 (SEQ ID No. 13), Dis3L variant 3 has accession number NM_001177784.1 (SEQ ID No. 14); and mouse Exosc10 has accession number NM_016699.2 (SEQ ID NO. 15).

The term individual includes humans and other mammals, specifically humans.

In one aspect, the individual is a human in need of treatment for an anemic disorder, hemophilia, thalassemia, sickle cell disease, bone marrow transplantation, hematopoietic stem cell transplantation, thrombocytopenia, pancytopenia, or hypoxia.

As used herein, anemia is a decrease in the number of red blood cells caused by decreased production or increased destruction of red blood cells. Anemia can be characterized by a reduced hematocrit level, the volume % of red blood cells in the blood, also referred to as the packed cell volume (PCV) or the erythrocyte volume fraction (EVF). The hematocrit varies with age and gender. For children, anemia is generally defined as a hematocrit below about 35%, for adult non-pregnant women below about 36%, for adult pregnant women below about 33%, and for adult men below about 39%. In one aspect, the individual with an anemic disorder has a reduced hematocrit.

Anemic disorders are associated with aging, infectious disease, chronic renal failure, end-stage renal disease, renal transplantation, cancer, AIDS (e.g., zidovudine-induced anemia), antiviral therapy, chronic stress, chemotherapy, radiation therapy, bone marrow transplantation, nutritional iron deficiency, blood-loss such as preparation for surgery with a high risk of blood loss, hemolysis, and are of genetic origin such as congenital dyserythropoietic anemia.

Exemplary agents that decrease the expression and/or activity of Exosc8, Exosc9, Dis3, Dis3L or Exosc10 include inhibitory nucleic acids.

In one aspect, the agent that decreases the expression of Exosc8, Exosc9, Dis3, Dis3L or Exosc10 is an inhibitory nucleic acid molecule, wherein administration of the inhibitory nucleic acid molecule selectively decreases the expression of Exosc8, Exosc9, Dis3, Dis3L or Exosc10. The term "inhibitory nucleic acid molecule" means a single stranded or double-stranded RNA or DNA, specifically RNA, such as triplex oligonucleotides, ribozymes, aptamers, small interfering RNA including siRNA (short interfering RNA) and shRNA (short hairpin RNA), antisense RNA, or a portion thereof, or an analog or mimetic thereof, that is capable of reducing or inhibiting the expression of a target gene or sequence Inhibitory nucleic acids can act by, for example, mediating the degradation or inhibiting the translation of mRNAs which are complementary to the interfering RNA sequence. An inhibitory nucleic acid, when administered to a mammalian cell, results in a decrease (e.g., by 5%, 10%, 25%, 50%, 75%, or even 90-100%) in the expression (e.g., transcription or translation) of a target sequence. Typically, a nucleic acid inhibitor comprises or corresponds to at least a portion of a target nucleic acid molecule, or an ortholog thereof, or comprises at least a portion of the complementary strand of a target nucleic acid molecule. Inhibitory nucleic acids may have substantial or complete identity to the target gene or sequence, or may include a region of mismatch (i.e., a mismatch motif). The sequence of the inhibitory nucleic acid can correspond to the full-length target gene, or a subsequence thereof. In one aspect, the inhibitory nucleic acid molecules are chemically synthesized.

The specific sequence utilized in design of the inhibitory nucleic acids is a contiguous sequence of nucleotides contained within the expressed gene message of the target. Factors that govern a target site for the inhibitory nucleic acid sequence include the length of the nucleic acid, binding affinity, and accessibility of the target sequence. Sequences may be screened in vitro for potency of their inhibitory activity by measuring inhibition of target protein translation and target related phenotype, e.g., inhibition of cell proliferation in cells in culture. In general it is known that most regions of the RNA (5' and 3' untranslated regions, AUG initiation, coding, splice junctions and introns) can be targeted using antisense oligonucleotides. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference.

Phosphorothioate antisense oligonucleotides may be used. Modifications of the phosphodiester linkage as well as of the heterocycle or the sugar may provide an increase in efficiency. Phosphorothioate is used to modify the phosphodiester linkage. An N3'-P5' phosphoramidate linkage has been described as stabilizing oligonucleotides to nucleases and increasing the binding to RNA. A peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

Short interfering (si) RNA technology (also known as RNAi) generally involves degradation of an mRNA of a particular sequence induced by double-stranded RNA (dsRNA) that is homologous to that sequence, thereby "interfering" with expression of the corresponding gene. A selected gene may be repressed by introducing a dsRNA which corresponds to all or a substantial part of the mRNA for that gene. Without being held to theory, it is believed that when a long dsRNA is expressed, it is initially processed by a ribonuclease III into shorter dsRNA oligonucleotides of as few as 21 to 22 base pairs in length. Accordingly, siRNA may be effected by introduction or expression of relatively short homologous dsRNAs. Exemplary siRNAs have sense and antisense strands of about 21 nucleotides that form approximately 19 nucleotides of double stranded RNA with overhangs of two nucleotides at each 3' end.

siRNA has proven to be an effective means of decreasing gene expression in a variety of cell types. siRNA typically decreases expression of a gene to lower levels than that achieved using antisense techniques, and frequently eliminates expression entirely. In mammalian cells, siRNAs are effective at concentrations that are several orders of magnitude below the concentrations typically used in antisense experiments.

The double stranded oligonucleotides used to effect RNAi are specifically less than 30 base pairs in length, for example, about 29, 28, 27, 26, 25, 24, 23, 22, 21, 20, 19, 18, or 17 base pairs or less in length, and contain a segment sufficiently complementary to the target mRNA to allow hybridization to the target mRNA. Optionally, the dsRNA oligonucleotide includes 3' overhang ends. Exemplary 2-nucleotide 3' overhangs are composed of ribonucleotide residues of any type and may be composed of 2'-deoxythymidine residues, which lowers the cost of RNA synthesis and may enhance nuclease resistance of siRNAs in the cell culture medium and within transfected cells. Exemplary dsRNAs are synthesized chemically or produced in vitro or in vivo using appropriate expression vectors. Longer RNAs may be transcribed from promoters, such as T7 RNA polymerase promoters, known in the art.

Longer dsRNAs of 50, 75, 100, or even 500 base pairs or more also may be utilized in certain embodiments. Exemplary concentrations of dsRNAs for effecting RNAi are about 0.05 nM, 0.1 nM, 0.5 nM, 1.0 nM, 1.5 nM, 25 nM, or 100 nM, although other concentrations may be utilized depending upon the nature of the cells treated, the gene target and other factors readily identifies by one of ordinary skill in the art.

Compared to siRNA, shRNA offers advantages in silencing longevity and delivery options. Vectors that produce shRNAs, which are processed intracellularly into short duplex RNAs having siRNA-like properties provide a renewable source of a gene-silencing reagent that can mediate persistent gene silencing after stable integration of the vector into the host-cell genome. Furthermore, the core silencing 'hairpin' cassette can be readily inserted into retroviral, lentiviral, or adenoviral vectors, facilitating delivery of shRNAs into a broad range of cell types.

A hairpin can be organized in either a left-handed hairpin (i.e., 5'-antisense-loop-sense-3') or a right-handed hairpin (i.e., 5'-sense-loop-antisense-3'). The shRNA may also contain overhangs at either the 5' or 3' end of either the sense strand or the antisense strand, depending upon the organization of the hairpin. If there are any overhangs, they are specifically on the 3' end of the hairpin and include 1 to 6 bases. The overhangs can be unmodified, or can contain one or more specificity or stabilizing modifications, such as a halogen or O-alkyl modification of the 2' position, or internucleotide modifications such as phosphorothioate, phosphorodithioate, or methylphosphonate modifications. The overhangs can be ribonucleic acid, deoxyribonucleic acid, or a combination of ribonucleic acid and deoxyribonucleic acid.

Additionally, a hairpin can further comprise a phosphate group on the 5'-most nucleotide. The phosphorylation of the 5'-most nucleotide refers to the presence of one or more phosphate groups attached to the 5' carbon of the sugar moiety of the 5'-terminal nucleotide. Specifically, there is only one phosphate group on the 5' end of the region that will form the antisense strand following Dicer processing. In one exemplary embodiment, a right-handed hairpin can include a 5' end (i.e., the free 5' end of the sense region) that does not have a 5' phosphate group, or can have the 5' carbon of the free 5'-most nucleotide of the sense region being modified in such a way that prevents phosphorylation. This can be achieved by a variety of methods including, but not limited to, addition of a phosphorylation blocking group (e.g., a 5'-O-alkyl group), or elimination of the 5'-OH functional group (e.g., the 5'-most nucleotide is a 5'-deoxy nucleotide). In cases where the hairpin is a left-handed hairpin, preferably the 5' carbon position of the 5'-most nucleotide is phosphorylated.

Hairpins that have stem lengths longer than 26 base pairs can be processed by Dicer such that some portions are not part of the resulting siRNA that facilitates mRNA degradation. Accordingly the first region, which may include sense nucleotides, and the second region, which may include antisense nucleotides, may also contain a stretch of nucleotides that are complementary (or at least substantially complementary to each other), but are or are not the same as or complementary to the target mRNA. While the stem of the shRNA can include complementary or partially complementary antisense and sense strands exclusive of overhangs, the shRNA can also include the following: (1) the portion of the molecule that is distal to the eventual Dicer cut site contains a region that is substantially complementary/homologous to the target mRNA; and (2) the region of the stem that is proximal to the Dicer cut site (i.e., the region adjacent to the loop) is unrelated or only partially related (e.g., complementary/homologous) to the target mRNA. The nucleotide content of this second region can be chosen based on a number of parameters including but not limited to thermodynamic traits or profiles.

Modified shRNAs can retain the modifications in the post-Dicer processed duplex. In exemplary embodiments, in cases in which the hairpin is a right handed hairpin (e.g., 5'-S-loop-AS-3') containing 2-6 nucleotide overhangs on the 3' end of the molecule, 2'-O-methyl modifications can be added to nucleotides at position 2, positions 1 and 2, or positions 1, 2, and 3 at the 5' end of the hairpin. Also, Dicer processing of hairpins with this configuration can retain the 5' end of the sense strand intact, thus preserving the pattern of chemical modification in the post-Dicer processed duplex. Presence of a 3' overhang in this configuration can be particularly advantageous since blunt ended molecules containing the prescribed modification pattern can be further processed by Dicer in such a way that the nucleotides carrying the 2' modifications are removed. In cases where the 3' overhang is present/retained, the resulting duplex carrying the sense-modified nucleotides can have highly favorable traits with respect to silencing specificity and functionality. Examples of exemplary modification patterns are described in detail in U.S. Patent Publication No. 20050223427 and International Patent Publication Nos. WO 2004/090105 and WO 2005/078094, the disclosures of each of which are incorporated by reference herein in their entirety.

shRNA may comprise sequences that were selected at random, or according to a rational design selection procedure. For example, rational design algorithms are described in International Patent Publication No. WO 2004/045543 and U.S. Patent Publication No. 20050255487, the disclosures of which are incorporated herein by reference in their entireties. Additionally, it may be desirable to select sequences in whole or in part based on average internal stability profiles ("AISPs") or regional internal stability profiles ("RISPs") that may facilitate access or processing by cellular machinery.

Ribozymes are enzymatic RNA molecules capable of catalyzing specific cleavage of mRNA, thus preventing translation. The mechanism of ribozyme action involves sequence specific hybridization of the ribozyme molecule to complementary target RNA, followed by an endonucleolytic cleavage event. The ribozyme molecules specifically include (1) one or more sequences complementary to a target mRNA, and (2) the well-known catalytic sequence responsible for mRNA cleavage or a functionally equivalent sequence (see, e.g., U.S. Pat. No. 5,093,246, which is incorporated herein by reference in its entirety).

While ribozymes that cleave mRNA at site-specific recognition sequences can be used to destroy target mRNAs, hammerhead ribozymes may alternatively be used. Hammerhead ribozymes cleave mRNAs at locations dictated by flanking regions that form complementary base pairs with the target mRNA. Specifically, the target mRNA has the following sequence of two bases: 5'-UG-3'. The construction and production of hammerhead ribozymes is well known in the art and is described more fully in U.S. Pat. No. 5,633,133, the contents of which are incorporated herein by reference.

Gene targeting ribozymes may contain a hybridizing region complementary to two regions of a target mRNA, each of which is at least 5, 6, 7, 8, 9, 10, 11, 12, 13, 14, 15, 16, 17, 18, 19, or 20 contiguous nucleotides (but which need not both be the same length).

Hammerhead ribozyme sequences can be embedded in a stable RNA such as a transfer RNA (tRNA) to increase cleavage efficiency in vivo. In particular, RNA polymerase III-mediated expression of tRNA fusion ribozymes is well known in the art. There are typically a number of potential hammerhead ribozyme cleavage sites within a given target cDNA sequence. Specifically, the ribozyme is engineered so that the cleavage recognition site is located near the 5' end of the target mRNA—to increase efficiency and minimize the intracellular accumulation of non-functional mRNA transcripts. Furthermore, the use of any cleavage recognition site located in the target sequence encoding different portions of the target mRNA would allow the selective targeting of one or the other target genes.

Ribozymes also include RNA endoribonucleases ("Cech-type ribozymes") such as the one which occurs naturally in Tetrahymena thermophile, described in International Patent Publication No. WO 88/04300. The Cech-type ribozymes have an eight base pair active site which hybridizes to a target RNA sequence where after cleavage of the target RNA takes place. In one embodiment, Cech-type ribozymes target eight base-pair active site sequences that are present in a target gene or nucleic acid sequence.

Ribozymes can be composed of modified oligonucleotides (e.g., for improved stability, targeting, etc.) and can be chemically synthesized or produced through an expression vector. Because ribozymes, unlike antisense molecules, are catalytic, a lower intracellular concentration is required for efficiency. Additionally, in certain embodiments, a ribozyme may be designed by first identifying a sequence portion sufficient to cause effective knockdown by RNAi. Portions of the same sequence may then be incorporated into a ribozyme.

Alternatively, target gene expression can be reduced by targeting deoxyribonucleotide sequences complementary to the regulatory region of the gene (i.e., the promoter and/or enhancers) to form triple helical structures that prevent transcription of the gene in target cells in the body. Nucleic acid molecules to be used in triple helix formation for the inhibition of transcription are specifically single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the target sequences that can be targeted for triple helix formation may be increased by creating a so-called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

Inhibitory nucleic acids can be administered directly or delivered to cells by transformation or transfection via a vector, including viral vectors or plasmids, into which has been placed DNA encoding the inhibitory oligonucleotide with the appropriate regulatory sequences, including a promoter, to result in expression of the inhibitory oligonucleotide in the desired cell. Known methods include standard transient transfection, stable transfection and delivery using viruses ranging from retroviruses to adenoviruses. Delivery of nucleic acid inhibitors by replicating or replication-deficient vectors is contemplated. Expression can also be driven by either constitutive or inducible promoter systems. In other embodiments, expression may be under the control of tissue or development-specific promoters.

Vectors may be introduced by transfection using carrier compositions such as Lipofectamine 2000 (Life Technologies) or Oligofectamine™ (Life Technologies). Transfection efficiency may be checked using fluorescence microscopy for mammalian cell lines after co-transfection of hGFP-encoding pAD3.

The effectiveness of the inhibitory oligonucleotide may be assessed by any of a number of assays, including reverse transcriptase polymerase chain reaction or Northern blot analysis to determine the level of existing human sclerostin mRNA, or Western blot analysis using antibodies which recognize the human sclerostin protein, after sufficient time for turnover of the endogenous pool after new protein synthesis is repressed.

In one embodiment, the inhibitory nucleic acid is an siRNA or an shRNA comprising 19 to 29 nucleotides that are substantially complementary to a sequence of 19 to 29 nucleotides of Exosc8 (SEQ ID NO. 1 or 9), specifically in the region of nucleotides 363 to 405, nucleotides 1129-1150, nucleotides 712-730, nucleotides 451 to 469 or nucleotides 501 to 519 of SEQ ID NO. 9 and the corresponding regions of SEQ ID NO. 1. Within the region of nucleotides 363 to 405, the regions of nucleotides 363 to 381, 384 to 405 or 371 to 392 may be employed.

Exemplary siRNAs for Exosc8 (SEQ ID NO. 9) include GAAAGAGGAUUUAUGCAUU (nucleotides 712-730, SEQ ID NO. 16), CAACAUAGGUUCAAUCAGU (nucleotides 451-469, SEQ ID NO. 17), UGGAGCCGCUG-GAGUAUUA (nucleotides 363-381, SEQ ID NO. 18), GGAAUACCACGGUCAUUUG (nucleotides 501-519, SEQ ID NO. 19), the corresponding nucleotides of SEQ ID NO. 1, and combinations thereof.

In one aspect, shRNAs that inhibit Exosc8 (SEQ ID NO. 9) include:

TGCTGTTGACAGTGAGCGCCAGGAGATTTCTGAAGGAAAATAGTGAAGC
CACAGATGTATTTTCCTTCAGAAATCTCCTGTTGCCTACTGCCTCGGA
(nucleotides 384-405, SEQ ID NO. 20)

TGCTGTTGACAGTGAGCGACGCTGGAGTATTACAGGAGATTAGTGAAGC
CACAGATGTAATCTCCTGTAATACTCCAGCGGTGCCTACTGCCTCGGA
(nucleotides 371-392, SEQ ID NO. 21)

TGCTGTTGACAGTGAGCGCCACAAAGAAGTGAGCAAGCTATAGTGAAGC
CACAGATGTATAGCTTGCTCACTTCTTTGTGTTGCCTACTGCCTCGGA
(nucleotides 1129-1150, SEQ ID NO. 22)

in SEQ ID NO. 9, and the corresponding regions of SEQ ID NO. 1.

In one embodiment, the inhibitory nucleic acid is a siRNA or a shRNA comprising 19 to 29 nucleotides that are substantially complementary to a sequence of 19 to 29 nucleotides of Exosc9 (SEQ ID NO. 2, 3 or 10). In one aspect, shRNAs that inhibit Exosc9 include:

TGCTGTTGACAGTGAGCGACAGATTGGAGACGGAATAGAATAGTGAAGCC
ACAGATGTATTCTATTCCGTCTCCAATCTGGTGCCTACTGCCTCGGA
(nucleotides 1094-1116 SEQ ID NO. 23)

TGCTGTTGACAGTGAGCGAAAAGAAGAGAACTGCTAACTAATAGTGAAGCC
ACAGATGTATTAGTTAGCAGTTCTCTTCTTCTGCCTACTGCCTCGGA
(nucleotides 1379-1401 SEQ ID NO. 24)

in SEQ ID NO. 10, and the corresponding regions of SEQ ID NO. 2 or 3.

In one embodiment, the inhibitory nucleic acid is a siRNA or a shRNA comprising 19 to 29 nucleotides that are substantially complementary to a sequence of 19 to 29 nucleotides of Dis3 (SEQ ID NO. 4, 5 or 11). In one aspect, shRNAs that inhibit Dis3 include TGCTGTTGACAGTGAGCGCCCACAGATCCCAGGAATAAATTAGTGAAGCC
ACAGATGTAATTTATTCCTGGGATCTGTGGTTGCCTACTGCCTCGGA
(nucleotides 2887-2909 SEQ ID NO. 25)

TGCTGTTGACAGTGAGCGACAGACAGTCAGCTGCAAGTTATAGTGAAGCC
ACAGATGTATAACTTGCAGCTGACTGTCTGCTGCCTACTGCCTCGGA
(nucleotides 593-615 SEQ ID NO. 26)

in SEQ ID NO 11 or the corresponding regions of SEQ ID NOs. 4 or 5.

In one embodiment, the inhibitory nucleic acid is an siRNA or an shRNA comprising 19 to 29 nucleotides that are substantially complementary to a sequence of 19 to 29 nucleotides of Dis3L (SEQ ID NO. 6, 7, 12, 13 or 14). In one aspect, shRNAs that inhibit Dis3L include:

TGCTGTTGACAGTGAGCGCGGCCGGAGACAGTATAACAAATAGTGAAGCC
ACAGATGTATTTGTTATACTGTCTCCGGCCTTGCCTACTGCCTCGGA
(nucleotides 414-436 SEQ ID NO. 27)

TGCTGTTGACAGTGAGCGCTACATCGATGTTGAAGCTAGATAGTGAAGCC
ACAGATGTATCTAGCTTCAACATCGATGTAATGCCTACTGCCTCGGA
(nucleotides 1677-1699 SEQ ID NO. 28)

in SEQ ID NO 12 or the corresponding regions of SEQ ID NOs. 6, 7, 13 or 14.

In one embodiment, the inhibitory nucleic acid is an siRNA or an shRNA comprising 19 to 29 nucleotides that are substantially complementary to a sequence of 19 to 29 nucleotides of Exosc10 (SEQ ID NO. 8 or 15), specifically in the region of nucleotides 340-401, 203 to 221, or 1624-1642 of SEQ ID No. 15, and the corresponding regions of SEQ ID NO. 8. Specific regions within 340-401 include 340-358 and 383-401.

In one aspect, siRNAs to Exosc10 (SEQ ID NO. 15) include GAAGUAAAGUGACUGAAUU (nucleotides 340-358, SEQ ID NO. 29), CGAUACCAAUGACGUGAUA (nucleotides 383-401, SEQ ID NO. 30), ACAGUUCG-GUGACGAGUAU (nucleotides 203-221, SEQ ID NO. 31), ACGGAUAUGUUCUACCAAA (nucleotides 1624-1642, SEQ ID NO. 32), the corresponding nucleotides of SEQ ID NO. 8, and combinations thereof.

As used herein, the term substantially complementary means that the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, or at least 95% identical. Optimal alignment of sequences for comparisons of identity may be conducted using a variety of algorithms known in the art. Sequence identity may also be determined using the BLAST algorithm.

Also included herein is a composition comprising a small interfering RNA, the small interfering RNA comprising 19 to 29 nucleotides that are substantially complementary to a sequence of 19 to 29 nucleotides of Exosc8, Exosc9, Dis3, Dis3L or Exosc10. In one aspect, the small interfering nucleic acid comprises 19 to 29 nucleotides that are substantially complementary to a sequence of 19 to 29 nucleotides of Exosc8 (SEQ ID NO. 1 or 9). In another aspect, the small interfering nucleic acid comprises 19 to 29 nucleotides that are substantially complementary to a sequence of 19 to 29 nucleotides of Exosc9 (SEQ ID NO. 2, 3 or 10). In another aspect, the small interfering nucleic acid comprises 19 to 29 nucleotides that are substantially complementary to a sequence of 19 to 29 nucleotides of Dis3 (SEQ ID NO. 4, 5 or 11). In another aspect, the small interfering nucleic acid comprises 19 to 29 nucleotides that are substantially complementary to a sequence of 19 to 29 nucleotides of Dis3L (SEQ ID NO. 6, 7, 12, 13 or 14). In another aspect, the small interfering nucleic acid comprises 19 to 29 nucleotides that are substantially complementary to a sequence of 19 to 29 nucleotides of Exosc10 (SEQ ID NO. 8 or 15). Exemplary small interfering RNAs are siRNA and shRNA.

Further included are pharmaceutical compositions comprising a pharmaceutically acceptable excipient and a small interfering RNA, the small interfering RNA comprising 19 to 29 nucleotides that are substantially complementary to a sequence of 19 to 29 nucleotides of Exosc8, Exosc9, Dis3, Dis3L or Exosc10. In one aspect, the small interfering nucleic acid comprises 19 to 29 nucleotides that are substantially complementary to a sequence of 19 to 29 nucleotides of Exosc8 (SEQ ID NO. 1 or 9). In another aspect, the small interfering nucleic acid comprises 19 to 29 nucleotides that are substantially complementary to a sequence of 19 to 29 nucleotides of Exosc9 (SEQ ID NO. 2, 3 or 10). In another aspect, the small interfering nucleic acid comprises 19 to 29 nucleotides that are substantially complementary to a sequence of 19 to 29 nucleotides of Dis3 (SEQ ID NO. 4, 5 or 11). In another aspect, the small interfering nucleic acid comprises 19 to 29 nucleotides that are substantially complementary to a sequence of 19 to 29 nucleotides of Dis3L (SEQ ID NO. 6, 7, 12, 13 or 14) In another aspect, the small interfering nucleic acid comprises 19 to 29 nucleotides that are substantially complementary to a sequence of 19 to 29 nucleotides of Exosc10 (SEQ ID NO. 8 or 15). Exemplary small interfering RNAs are siRNA and shRNA including the molecules specifically described herein, or the corresponding sequences in the human Exosc8, Exosc9, Dis3, Dis3L and Exosc10.

The invention is further illustrated by the following non-limiting examples.

EXAMPLES

Methods

Cell culture: G1E-ER-GATA-1 cells were cultured in Iscove's Modified Dulbecco's Medium (IMDM) (Gibco®) containing 15% FBS (Gemini Bio Products), 1% penicillin-streptomycin (Cellgro®), 2 U/ml erythropoietin, 120 nM monothioglycerol (Sigma-Aldrich®), 0.6% conditioned medium from a kit ligand producing CHO cell line, and 1 µg/ml puromycin (Gemini Bio Products). Cells were treated with 1 µM β-estradiol (Steraloids, Inc) to induce ER-GATA-1 activity. G1E cells were cultured in the same media as G1E-ER-GATA-1 cells without puromycin. Primary fetal liver erythroid progenitor cells were cultured in StemPro®-34 (Gibco®) supplemented with 10% nutrient supplement (Gibco), 2 mM L-glutamine (Cellgro®), 1% penicillin-streptomycin (Cellgro®), 100 µM monothioglycerol (Sigma-Aldrich®), 1 µM dexamethasone (Sigma-Aldrich®), 0.5 U/ml of erythropoietin, and 1% conditioned medium from a kit ligand producing CHO cell line for expansion. For differentiation, cells were cultured in ES IMDM (glutamine-free) (Hyclone®) containing 10% FBS (Gemini Bio Products), 10% PDS (Animal Technologies), 5% PFHM II (Gibco®), 2 mM L-glutamine (Cellgro®), 1% penicillin-streptomycin (Cellgro®), 100 µM monothioglycerol (Sigma-Aldrich®), and 5 U/ml of erythropoietin. Cells were grown in a humidified incubator at 37° C. with 5% carbon dioxide. All percentages are vol/vol unless otherwise noted.

Transmission electron microscopy (TEM). Cells were fixed in 0.1M sodium cacodylate buffer, pH 7.4, containing 2.5% glutaraldehyde and 2% paraformaldehyde overnight at 4° C. The cells were then post-fixed in 2% Osmium Tetroxide in 0.1 M sodium cacodylate for 2 h at room temperature. Following post-fixation, the samples were dehydrated in a graded ethanol series, then further dehydrated in propylene oxide and embedded in Epon epoxy resin. Samples were sectioned for TEM using a Reichert-Jung Ultracut-E Ultra-microtome and contrasted with Reynolds lead citrate and 8% uranyl acetate in 50% EtOH. Ultrathin sections were observed with a Philips CM120 electron microscope, and images were captured with a MegaView III side mounted digital camera.

TEM immunogold staining. Cells were washed with PBS and fixed in 0.1 M PB buffer (0.2 M sodium phosphate monobasic combined with 0.2 M sodium phosphate dibasic, pH 7.4) containing 0.1% glutaraldehyde and 4% paraformaldehyde overnight at 4° C. Fixed cells were embedded in 3% agarose, which was sectioned using a vibratome. After washing with 0.1 M PB buffer, freshly prepared 0.1% $NaBH_4$ in 0.1 M PB was used to inactivate residual aldehyde groups for 10 min. Following rinsing with 0.1 M PB buffer, specimens were permeabilized in PBS containing 0.2% Triton X-100 for 30 min at room temperature with gentle agitation, followed by PBS washes. AURION blocking solution was used to block for 1 h at room temperature. After washing with incubation buffer (0.2% AURION BSA-c in PBS), specimens were incubated with LC3 rabbit polyclonal antibody (PM036, MBL) overnight at 4° C., followed by extensive washing with incubation buffer. Samples were incubated with ultra-small gold-conjugated secondary antibody (1/100 dilution) in incubation buffer overnight at 4° C. Following extensive washing with incubation buffer, specimens were washed with PBS before post-fixation with 0.1 M PB containing 2% glutaraldehyde for 1 h at room temperature. After washing with 0.1 M PB followed by ECS solution, specimens were incubated with silver enhancement solution for 2 h, washed extensively with ECS solution, dehydrated, and embedded following the TEM procedure described above.

Protein analysis. Equal numbers of cells were boiled for 10 min in SDS sample buffer (25 mM Tris, pH 6.8, 2% β-mercaptoethanol, 3% SDS, 0.005% bromophenol blue, and 5% glycerol). Samples were resolved by SDS-PAGE, and proteins were measured by semi-quantitative Western blotting with ECL Plus™ (Pierce®). GATA-1 rat monoclonal antibody (SC-265) and Foxo3 rabbit polyclonal antibody (07-702) were from Santa Cruz Biotechnology and Millipore, respectively. β-actin mouse monoclonal antibody (3700) was from Cell Signaling Technology, and LC3B mouse monoclonal antibody (M115-3) (Medical and Biological Laboratories) were used.

Quantitative real-time RT-PCR. Total RNA was purified with Trizol® (Invitrogen™). cDNA was prepared by annealing 1.5 mg of RNA with 250 ng of a 5:1 mixture of random hexamer and oligo (dT) primers heated at 68° C. for 10 min. This was followed by incubation with Murine Moloney Leukemia Virus Reverse Transcriptase (Invitrogen™) combined with 10 mM DTT, RNasin (Promega), and 0.5 mM dNTPs at 42° C. for 1 h. The mixture was diluted to a final volume of 120 µl and heat inactivated at 95° C. for 5 min. RT-PCR reactions (20 µl) contained 2 µl of cDNA, appropriate primers, and 10 µl of SYBR green master mix (Applied Biosystems®). Product accumulation was monitored by SYBR green fluorescence. A standard curve of serial dilutions of cDNA samples was used to determine relative expression. mRNA levels were normalized to 18S rRNA.

Quantitative chromatin immunoprecipitation (ChIP) assay. ChIP was conducted as known in the prior art. ER-GATA-1 and endogenous GATA-1 were immunoprecipitated with rabbit anti-GATA-1 antibody, and Foxo3 was immunoprecipitated with rabbit anti-Foxo3 antibodies (Millipore and Santa Cruz Biotechnology). Rabbit preimmune sera (PI, Covance) was used as a control. Phosphorylated RNA Polymerase II was immunoprecipitated with mouse anti-pSer5 Pol II antibody (Covance). Mouse IgMµ (Sigma) was used as a control. Samples were analyzed by quantitative real-time PCR (ABI StepOnePlus™), and product was measured by SYBR Green fluorescence. The amount of product was determined relative to a standard curve generated from a serial dilution of input chromatin. Dissociation curves revealed that primer pairs generated single products.

Primary murine bone marrow erythroid precursors. Murine bone marrow erythroblasts were isolated from femur and tibia from 8 week old mice. Bone marrow cells were resuspended in 90 µl of MACS buffer (PBS containing 0.5% BSA and 2 mM EDTA) per $5 \times 10^6$ cells and 10 µl of Anti-Ter119 Microbeads (Miltenyi Biotec) were added. After 15 min incubation at 4° C., a 15 fold volume of MACS buffer was added to wash microbead-cell complexes. After centrifugation at 1200 rpm for 10 min at 4° C., cells were resuspended in 1 ml MACS buffer per $1 \times 10^8$ cells and applied to the MACS LS column. After washing the column four times with 3 ml of MACS buffer, Ter119 microbead-conjugated cells were eluted twice with 2.5 ml MACS buffer.

Primary fetal liver erythroid progenitor cell isolation. Embryonic day 14.5 fetal livers were used to isolate primary erythroid progenitor cells using EasySep™ negative selection Mouse Hematopoietic Progenitor Cell Enrichment Kit (StemCell™ Technologies). Briefly, fetal liver cells were resuspended at a concentration of 5×10$^7$ cells/ml in PBS containing 2% FBS, 2.5 mM EDTA, and 10 mM glucose, and EasySep™ Mouse Hematopoietic Progenitor Cell Enrichment Cocktail was added at 50 µl/ml supplemented with 2.5 µg/ml biotin-conjugated CD71 antibody (eBioscience). After 15 min incubation on ice, cells were washed once by centrifugation for 5 min at 1200 rpm at 4° C. Cells were resuspended at a concentration of 5×10$^7$ cells/ml in PBS containing 2% FBS, 2.5 mM EDTA, and 10 mM glucose, and EasySep™ Biotin Selection Cocktail was added at 100 µl/ml. After 15 min on ice, EasySep™ Mouse Progenitor Magnetic Microparticles were added at 50 µl/ml. After 10 min on ice, cells were resuspended to a total volume of 4 ml and incubated with a magnet for 3 min. Unbound progenitor cells were transferred into a 15 ml tube and used for subsequent experiments.

siRNA-mediated knockdown. Dharmacon siGENOME® Smartpools against mouse Foxo3, Exosc8, Exosc10, Dis3, Dis3l were used with non-targeting siRNA pool as a control. siRNA (240 pmol) was transfected into 3×10$^6$ of G1E-ER-GATA-1 cells or G1E cells using the Amaxa® Nucleofector™ Kit R (Amaxa® Inc.) with program G-16. siRNA was transfected twice at 0 and 24 h. G1E-ER-GATA-1 cells were treated with β-estradiol for the indicated times. The smartpool for Exosc8 includes GAAAGAGGAUUUAUGCAUU (nucleotides 712-730, SEQ ID NO. 16), CAACAUAG-GUUCAAUCAGU (nucleotides 451-469, SEQ ID NO. 17), UGGAGCCGCUGGAGUAUUA (nucleotides 363-381, SEQ ID NO. 18), and GGAAUACCACGGUCAUUUG (nucleotides 501-519, SEQ ID NO. 19). The smartpool for Exosc10 includes GAAGUAAAGUGACUGAAUU (nucleotides 340-358, SEQ ID NO. 29), CGAUAC-CAAUGACGUGAUA (nucleotides 383-401, SEQ ID NO. 30), ACAGUUCGGUGACGAGUAU (nucleotides 203-221, SEQ ID NO. 31), and ACGGAUAUGUUCUAC-CAAA (nucleotides 1624-1642, SEQ ID NO. 32).

shRNA-mediated knockdown. MiR-30 context Exosc8 (Rrp43), Dis3 (Rrp6), Dis3L and Exosc9 (Rrp45) shRNAs were cloned into MSCV-PIG vector kindly provided by Dr. Mitchell Weiss using BglII and XhoI sites. 1×10$^5$ primary erythroid progenitor cells were spinfected with 100 µl of retrovirus supernatant and 8 µg/ml polybrene in 400 µl of fetal liver expansion media at 1200×g for 90 min at 30° C.

MiR-30 context Exosc8 shRNA 1 sequence:
(SEQ ID NO. 20)
TGCTGTTGACAGTGAGCGCCAGGAGATTTCTGAAGGAAAATAGTGAA
GCCACAGATGATTTTCCTTCAGAAATCTCCTGTTGCCTACTGCCTCG
GA.

MiR-30 context Exosc8 shRNA 2 sequence:
(SEQ ID NO. 21)
TGCTGTTGACAGTGAGCGACGCTGGAGTATTACAGGAGATTAGTGAA
GCCACAGATGTAATCTCCTGTAATACTCCAGCGGTGCCTACTGCCTC
GGA.

MiR-30 context Exosc9 shRNA 1 sequence:
(SEQ ID NO. 23)
TGCTGTTGACAGTGAGCGACAGATTGGAGACGGAATAGAATAGTGAA
GCCACAGATGTATTCTATTCCGTCTCCAATCTGTGCCTACTGCCTC
GGA MiR-30 context Exosc9 shRNA 2 sequence:
(SEQ ID NO. 24)
TGCTGTTGACAGTGAGCGAAAGAAGAGAACTGCTAACTAATAGTGAA
GCCACAGATGTATTAGTTAGCAGTTCTCTTCTTCTGCCTACTGCCTC
GGA.

MiR-30 context Dis3 shRNA 1 sequence
(SEQ ID No. 25):
TGCTGTTGACAGTGAGCGCCCACAGATCCCAGGAATAAATTAGTGAA
GCCACAGATGTAATTTATTCCTGGGATCTGTGGTTGCCTACTGCCTC
GGA MiR-30 context Dis3 shRNA 2 sequence
(SEQ ID No. 26):
TGCTGTTGACAGTGAGCGACAGACAGTCAGCTGCAAGTTATAGTGAA
GCCACAGATGTATAACTTGCAGCTGACTGTCTGCTGCCTACTGCCTC
GGA MiR-30 context Dis3L shRNA 1 sequence
(SEQ ID No. 27):
TGCTGTTGACAGTGAGCGCGGCCGGAGACAGTATAACAAATAGTGAA
GCCACAGATGTATTTGTTATACTGTCTCCGGCCTTGCCTACTGCCTC
GGA MiR-30 context Dis3 shRNA 1 sequence
(SEQ ID No. 28):
TGCTGTTGACAGTGAGCGCTACATCGATGTTGAAGCTAGATAGTGAA
GCCACAGATGTATCTAGCTTCAACATCGATGTAATGCCTACTGCCTC
GGA Bold sequences denote sense and antisense sequences.

Flow cytometry. Cells were washed with PBS once, and 1×10$^6$ cells were stained with 0.8 µg of anti-mouse Ter119-APC and anti-mouse CD71-PE (eBioscience) at 4° C. for 30 min in the dark. After staining, cells were washed three times with 2% BSA in PBS. For Exosc8 knockdown experiments, samples were analyzed using a BD LSR II flow cytometer (BD Biosciences). For Exosc9 knockdown experiments, which included an Exosc8 knockdown positive control, Ter119 and CD71 staining was analyzed using a BD FACSAria II cell sorter (BD Biosciences), at which time shRNA expressing cells were sorted from the total population, utilizing the GFP marker which is co-expressed with the shRNA, for subsequent transcriptional analysis. DAPI (Sigma) staining discriminated dead cells.

Cell cycle analysis. Cells were resuspended at 5×10$^5$ cells/ml in medium containing 20 µg/ml Hoechst 33342 (Invitrogen) and incubated at 37° C. for 30 min. After incubation, this cell suspension was adjusted to 2×10$^6$ cells/ml. DNA contents were measured using BD™ LSR II (BD™ Biosciences) and Modfit LT 3.2.1 (Verity software house) was used to analyze the data.

Transcriptional profiling. Amino Allyl RNA was synthesized from mRNA, labeled, and hybridized to 8×60K Mouse Whole Genome arrays (Agilent) with three biological replicates. Arrays were read utilizing a G-2505C DNA Microarray Scanner with Surescan High Resolution (Agilent). EDGE3 web-based two-color microarray analysis software and Microsoft Excel were used for data analysis.

Immunofluorescence. To detect endogenous LC3B, cytospun cells were fixed with 3.7% paraformaldehyde in PBS for 10 min at room temperature. After washing with PBS, cells were permeabilized using 0.2% Triton X-100 in PBS for 15 min at room temperature. After washing with PBS, slides were blocked with 10% blocking solution BlokHen® (Aves Labs, Inc.) in PBS-T for 1 h at 37° C. and then incubated with 1.6 µg/ml LC3 rabbit polyclonal antibody (Medical and Biological Laboratories) in 2% BlokHen® in PBS-T overnight at 4° C. After washing three times with PBS-T, slides were incubated with 8 μg/ml Alexa Fluor 488 goat anti-rabbit IgG antibody (Invitrogen) for 1 h at 37° C. Slides were washed three times with PBS-T and mounted using Vectashield® mounting medium with DAPI (Vector Laboratories, Inc.). Cells were photographed using a 100×/1.4 oil objective (Olympus IX2-UCB). For quantitation, cells containing more than two LC3-positive punctae structures were scored as autophagosome-positive cells. At least 200 cells were counted per slide, and three independent biological replicates were counted.

Generation of 3D exosome structure: Protein structure coordinate files for the human exosome complex were downloaded from the Research Collaboratory for Structural Bioinformatics Protein Data Bank (accession number 2NN6). Structural images were generated using PyMOL.

Statistical analysis. Paired Student's T-test with the web-based tool was used to calculate statistical significance. EDGE3 analysis software and online NIH DAVID tool were used for statistical analysis of microarray data and gene ontology (GO) terms analysis, respectively.

Example 1

Autophagy Induction Via GATA-1/Foxo3 Feed-Forward Loop

To gain mechanistic insights into how autophagy is initiated in a specific developmental context, a genetic complementation analysis was conducted in GATA-1-null G1E-ER-GATA-1 cells that stably express ER-GATA-1 (subsequently referred to as GATA-1). Conditional GATA-1 activation with estradiol induces a physiological erythroid gene expression program and erythroid maturation, recapitulating a window of the maturation process that occurs in vivo. GATA-1 directly induces select autophagy genes and MAP1LC3B (LC3B)-positive punctae. Transmission electron microscopy (TEM) was used to test whether GATA-1-induced punctae detected by immunofluorescence analysis represent autophagosomes/autolysosomes. GATA-1 activation for 24 or 48 hours induced erythroid maturation associated with accumulation of large cytoplasmic vesicles (FIG. 1). Both the number of vesicles per cell and vesicle size increased, although mature cells retained some small vesicles (<0.5 μm$^2$) (data not shown). Immunogold TEM analysis with anti-LC3B antibody confirmed that GATA-1-induced vesicles contain the autophagosome marker LC3B and bear morphological attributes of autophagosomes/autolysosomes (data not shown). Thus, GATA-1 increases the number and size of these autophagy structures as an important step in erythroid cell maturation.

Figure 2:
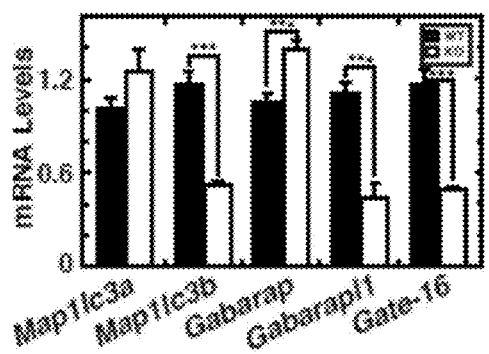
FIG. 2 shows real-time RT-PCR analysis of mammalian ATG8 homolog transcript levels in bone marrow Ter119+ cells from wild type and Foxo3$^{-/-}$ mice (mean+/−SE; 6 independent biological samples).

It has been shown that as siRNA-mediated downregulation of Foxo3 decreased GATA-1-induced expression of select autophagy genes, without affecting all GATA-1 target genes. Foxo3 amplifies GATA-1 activity in a context-dependent manner. To test the implications of this Foxo3 activity for autophagy gene expression in vivo, autophagy gene expression in primary bone marrow Ter119+ cells from wild type and Foxo3$^{-/-}$ mice was quantitated. Foxo3 mRNA was undetectable, and Gata1 mRNA was approximately 30% higher in Ter119+ cells from Foxo3$^{-/-}$ versus Foxo3$^{+/+}$ bone marrow (data not shown). Foxo3 and GATA-1 protein levels were concordant with mRNA levels (data not shown). The expression of autophagy genes regulated by GATA-1 in G1E-ER-GATA-1 cells (Map1lc3b, Gabarapl1, Gate-16) decreased significantly by 50-60% (FIG. 2). Thus, Foxo3 amplifies expression of these genes in vivo, validating the G1E-ER-GATA-1 results.

To elucidate how GATA-1 and Foxo3 function combinatorially to regulate autophagy genes, it was determined whether they co-occupy chromatin at autophagy gene loci. Using a quantitative ChIP assay, GATA-1 and Foxo3 occupancy was measured at chromatin sites containing Foxo3 DNA motifs. GATA-1 and Foxo3 occupied indistinguishable sites at Gabarapl1 and Gate-16 (data not shown). To test whether endogenous GATA-1 and Foxo3 co-occupy chromatin in primary erythroblasts, quantitative ChIP analysis was conducted with primary Ter119+ cells from mouse bone marrow. GATA-1 and Foxo3 co-occupied sites at Gabarapl1 and Gate-16, recapitulating the G1E-ER-GATA-1 results (data not shown). GATA-1 and FOXO3 co-occupancy at GABARAPL1 and GATE-16 was also confirmed in primary erythroblasts derived from human CD34+ peripheral blood mononuclear cells (data not shown). The co-occupancy might reflect the presence of both factors in a complex at an identical chromatin site or independent occupancy of neighboring sites that cannot be segregated due to resolution limitations (data not shown). To test these models, tiled primers were used to quantitate GATA-1 and Foxo3 occupancy over a broader chromosomal region (data not shown). Maximal GATA-1 and Foxo3 occupancy occurred at distinct sites containing GATA and Foxo3 DNA motifs respectively, suggesting that GATA-1 and Foxo3 occupy neighboring sites (data not shown).

Figure 3:
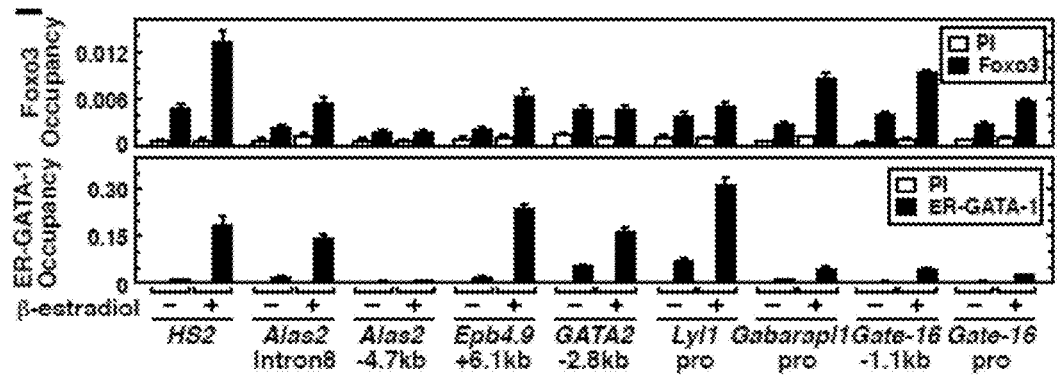
FIG. 3 shows a ChIP analysis of Foxo3 and GATA-1 occupancy at select autophagy genes and GATA-1 target gene loci in untreated and β-estradiol treated (24 hours) G1E-ER-GATA-1 cells (mean+/−SE; 4 independent experiments).
Figure 4:
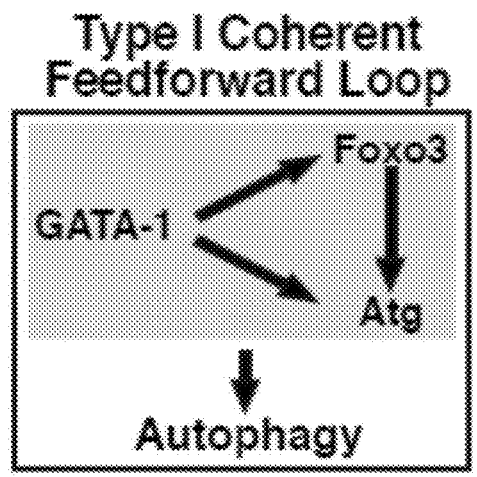
FIG. 4 illustrates a GATA-1/Foxo3 network motif.
Figure 5:
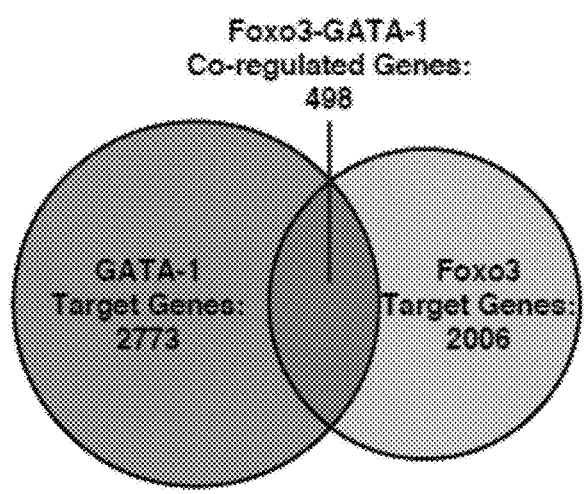
FIG. 5 shows Venn diagrams depicting the number of genes regulated uniquely or co-regulated by GATA-1 and Foxo3.

Given the close proximity of the GATA-1 and Foxo3 occupancy sites, it was investigated whether GATA-1 regulates Foxo3 chromatin occupancy and vice versa. GATA-1 induced Foxo3 chromatin occupancy at select autophagy loci and at additional GATA-1 target genes (≤3 fold, p<0.0001), but not at all GATA-1 target genes (e.g., at Ly11 promoter and Gata2−2.8 site) in G1E-ER-GATA-1 cells (FIG. 3). The Alas2 −4.7 kb site, which was not bound by GATA-1, served as a negative control. It was also determined whether Foxo3 increases GATA-1 chromatin occupancy. Knocking-down Foxo3 expression (data not shown) increased GATA-1 occupancy up to 30% at autophagy and non-autophagy gene loci (data not shown). Thus, while GATA-1 induced Foxo3 chromatin occupancy, downregulating Foxo3 did not decrease GATA-1 chromatin occupancy. As suggested previously that GATA-1 induces Foxo3 mRNA and occupies the FOXO3 locus, GATA-1 induced Foxo3 protein 6.7 fold (p<0.001) (data not shown). These results illustrate a type I coherent feed-forward loop, in which GATA-1 directly activates autophagy genes and induces Foxo3, and Foxo3 also activates the autophagy genes (FIG. 4). The model predicts that the feed-forward loop would buffer against transiently elevated input stimuli (e.g., active GATA-1 and/or Foxo3), thereby suppressing the premature induction of autophagy, which would be deleterious to the erythroblast.

Example 2

GATA-1/Foxo3 Cooperativity in Erythroid Cell Biology

To determine the extent of the GATA-1/Foxo3-regulated genetic network in erythroid cells, the transcriptome of Foxo3-knockdown versus control cells was profiled in the context of active GATA-1. Comparison of the Foxo3-regulated genes to the existing GATA-1 target gene dataset in G1E-ER-GATA-1 cells revealed 498 of the 2006 Foxo3-regulated genes (approximately 25%) as GATA-1-regulated. GATA-1/Foxo3 co-regulate a cohort of genes in erythroid cells more extensive than solely the autophagy genes (FIG.

Figure 6:
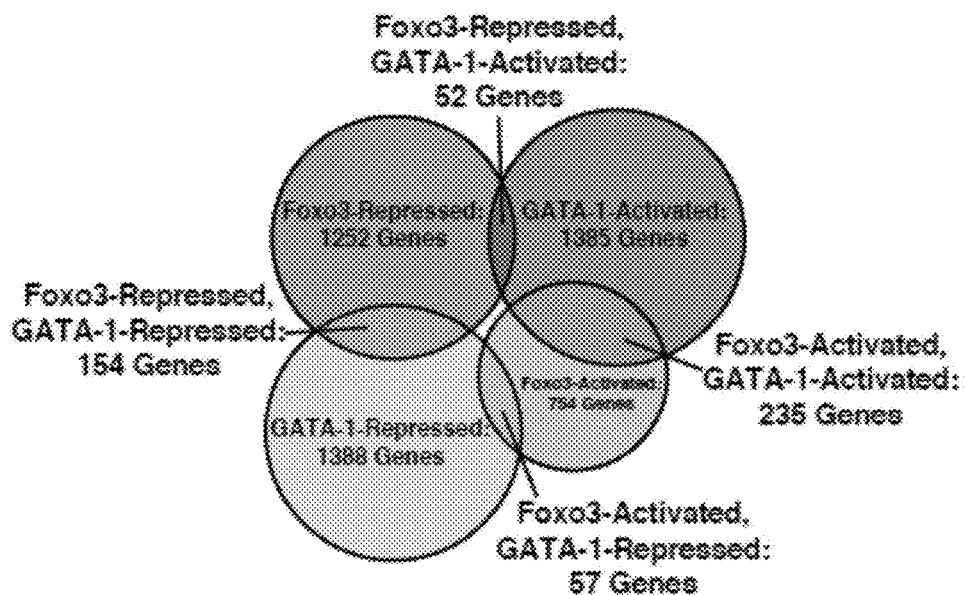
FIG. 6 shows Venn diagrams demonstrating relationships between GATA-1- and Foxo3-activated and -repressed genes.
Figure 7:
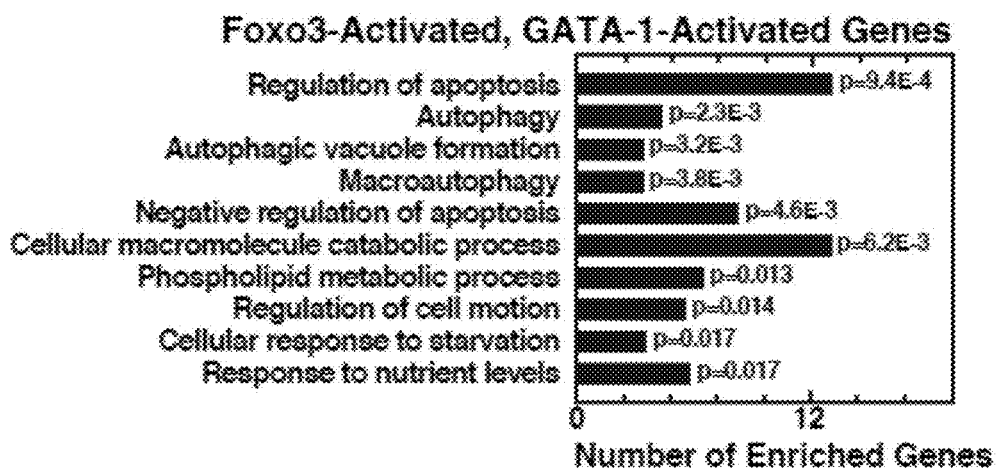
FIG. 7 shows a gene ontology analysis of GATA-1/Foxo3-co-activated genes.
Figure 8:
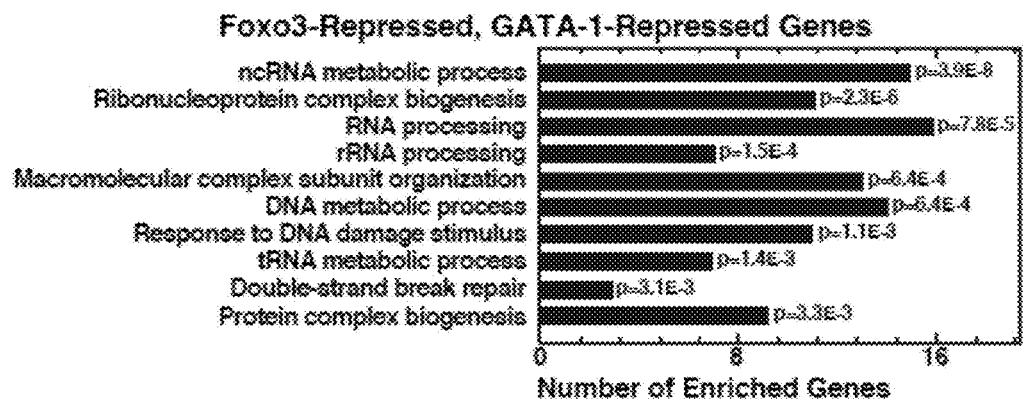
FIG. 8 shows a gene ontology analysis of GATA-1/Foxo3-co-repressed genes.

5). The co-regulated genes were classified as GATA-1- or Foxo3-activated or -repressed. GATA-1 and Foxo3 regulated 78% of the co-regulated genes in the same direction (FIG. 6). GATA-1/Foxo3 activated and repressed 235 and 154 genes, respectively (FIG. 6). Gene ontology (GO) analysis was conducted to assess whether these distinct regulatory modes have hallmark functional signatures, and the top five GO terms ascribed to the co-activated genes implicate apoptosis and autophagy (FIG. 7). Genes involved in "non-coding RNA metabolic process" or "RNA processing" were uniquely and significantly enriched in the co-repressed cohort (FIG. 8). Genes assigned to these categories are listed Table 1A and B. Importantly, these genes could not have been predicted from prior genomic analyses of GATA factor function or hematopoiesis.

TABLE 1A

Regulation of Apoptosis

| Gene Name | Fold Change | |
|---|---|---|
| | GATA-1 | Foxo3 |
| Atf5 | 1.81 | 2.85 |
| B4galt1 | 4.49 | 2.61 |
| Cdkn1b | 6.59 | 2.33 |
| Cln8 | 7.43 | 1.88 |
| Ddit3 | 4.39 | 1.88 |
| Dedd2 | 3.13 | 1.90 |
| Il4 | 13.6 | 1.88 |
| Rb1cc1 | 2.49 | 2.56 |
| Serinc3 | 3.84 | 2.39 |
| Sgms1 | 2.58 | 1.89 |
| Ube2b | 1.87 | 2.11 |
| Tax1bp1 | 2.24 | 1.75 |
| Trp53inp1 | 10.7 | 3.73 |

TABLE 1B ncRNA Metabolic Process

| Gene Name | Fold Change | |
|---|---|---|
| | GATA-1 | Foxo3 |
| Aarsd1 | −2.10 | −1.71 |
| Cars2 | −3.51 | −1.71 |
| Exosc5 | −2.07 | −1.77 |
| Exosc8 | −1.74 | −2.40 |
| Lin28b | −2.97 | −2.19 |
| Nafl | −3.85 | −1.71 |
| Nop10 | −1.78 | −1.57 |
| Nsa2 | −2.27 | −2.08 |
| Nsun2 | −3.51 | −1.73 |
| Rpp38 | −2.57 | −1.80 |
| Tarsl2 | −1.85 | −2.68 |
| Tsen2 | −2.46 | −2.06 |
| Wdr4 | −3.67 | −2.05 |
| Wdr36 | −2.38 | −1.64 |
| Wdr55 | −2.19 | −1.57 |

Example 3

Linking the GATA-1/Foxo3 Feed-Forward Loop to RNA Surveillance Machinery

Figure 9:
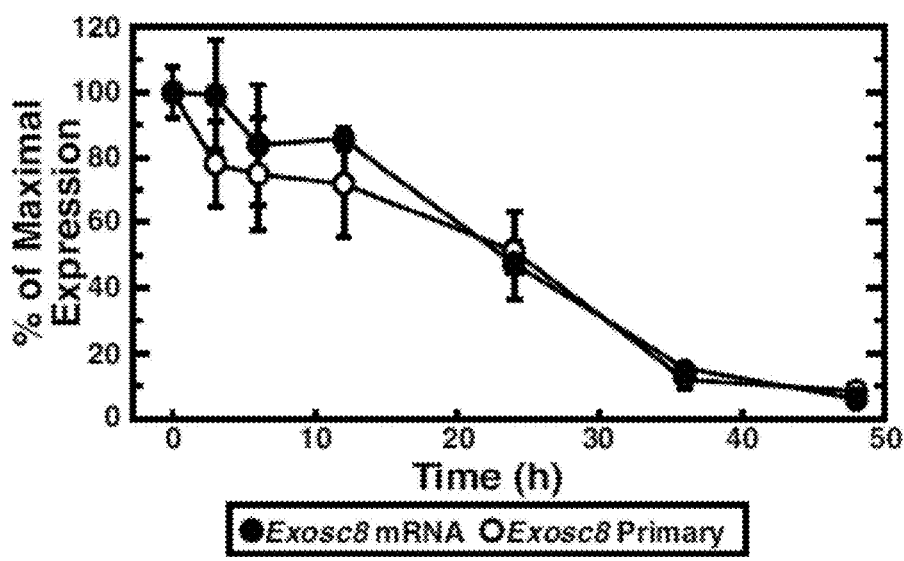
FIG. 9 shows an RT-PCR analysis of Exosc8 expression upon GATA-1 activation in G1E-ER-GATA-1 cells (mean+/−SE; 3 independent experiments). Values were normalized to 18S rRNA expression.
Figure 10:
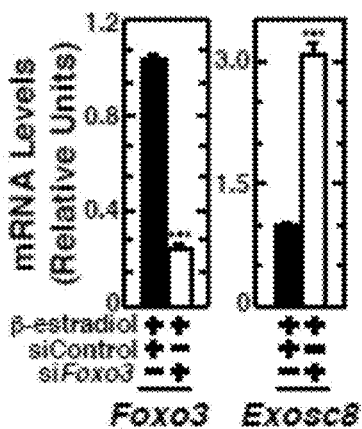
FIG. 10 shows an RT-PCR analysis of Exosc8 mRNA level upon Foxo3 knockdown in G1E-ER-GATA-1 cells (mean+/−SE; 4 independent experiments). Values were normalized to 18S rRNA expression.
Figure 11:
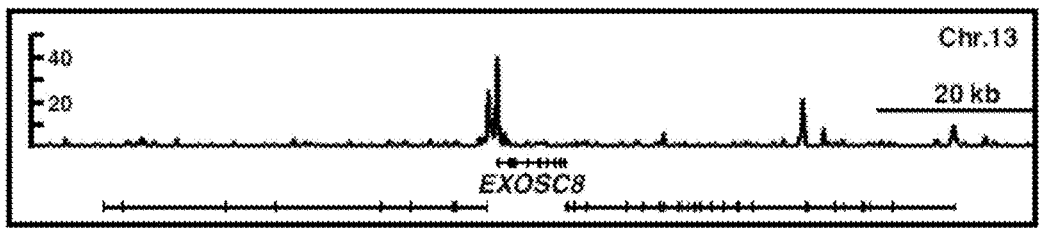
FIG. 11 shows a ChIP-seq profile of GATA-1 occupancy at EXOSC8 in primary human erythroblasts.

Two of the highly GATA-1/Foxo3-repressed genes implicated in "non-coding RNA metabolic process" were Exosc8 and Exosc5 (Rrp46), essential core components of the exosome complex. Exosc8 contains a catalytically inactive RNase PH domain. Using real-time RT-PCR to confirm the microarray data, GATA-1 repressed Exosc8 expression 25 fold, and knocking-down Foxo3 de-repressed Exosc8 expression 3 fold (FIGS. 9 and 10). Endogenous GATA-1 occupied the EXOSC8 promoter in primary human erythroblasts, suggesting direct GATA-1 transcriptional regulation (FIG. 11). The kinetics of GATA-1-mediated Exosc8 repression are slower than prototypical GATA-1-repressed target genes and resemble the slow induction of the direct GATA-1 target βmajor, which has been attributed to a GATA-1 requirement to upregulate FOG-1 expression. GATA-1 would be required to upregulate Foxo3 as a prelude to functioning combinatorially with Foxo3 to confer maximal Exosc8 repression. This method of gene regulation delays the reversal of the response (Exosc8 repression) upon loss of the activating stimuli (GATA-1 and Foxo3).

Example 4

Figure 12:
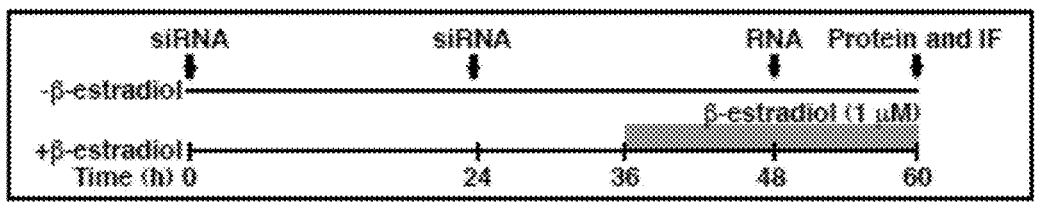
FIG. 12 illustrates the Exosc8 knockdown strategy in G1E-ER-GATA-1 cells. IF, immunofluorescence.
Figure 13:
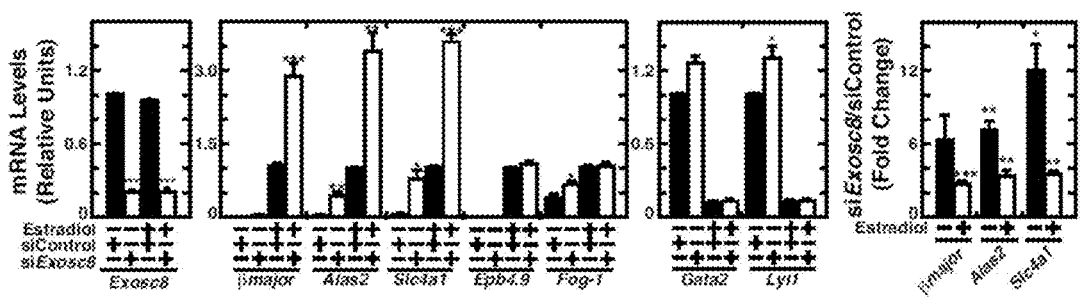
FIG. 13 shows quantitative real-time RT-PCR analysis of mRNA levels in control versus Exosc8 knockdown G1E-ER-GATA-1 cells (mean+/−SE; 3 independent experiments). Values were normalized to 18S rRNA expression. mRNA levels are shown relative to the control siRNA with estradiol treatment for activated genes (left) and without estradiol treatment for repressed genes (middle). (Right) Fold changes upon Exosc8 knockdown relative to control.

Exosc8 Regulates a Cohort of GATA-1 Target Genes Essential for Erythroid Maturation Though GATA-1 represses as many genes as it activates, the functional significance of many of the GATA-1-repressed genes is not established. Without being held to theory, it is believed that a cohort of the encoded proteins promote precursor cell expansion or survival, thus actively counteracting maturation. Since GATA factors have not been linked to the exosome complex, the functional consequences of GATA-1-mediated Exosc8 repression were investigated by knocking-down Exosc8 in G1E-ER-GATA-1 cells. (FIG. 12) Knocking down Exosc8 by approximately 80% significantly enhanced expression of several GATA-1-activated genes by 3 to 12-fold (βmajor, Alas2, and Slc4a1), while other GATA-1 activated genes (Epb4.9 and Fog-1) were largely unaffected. GATA-1-mediated repression of Gata2 and Lyl1 were unaltered by the knockdown (FIG. 13).

Figure 14:
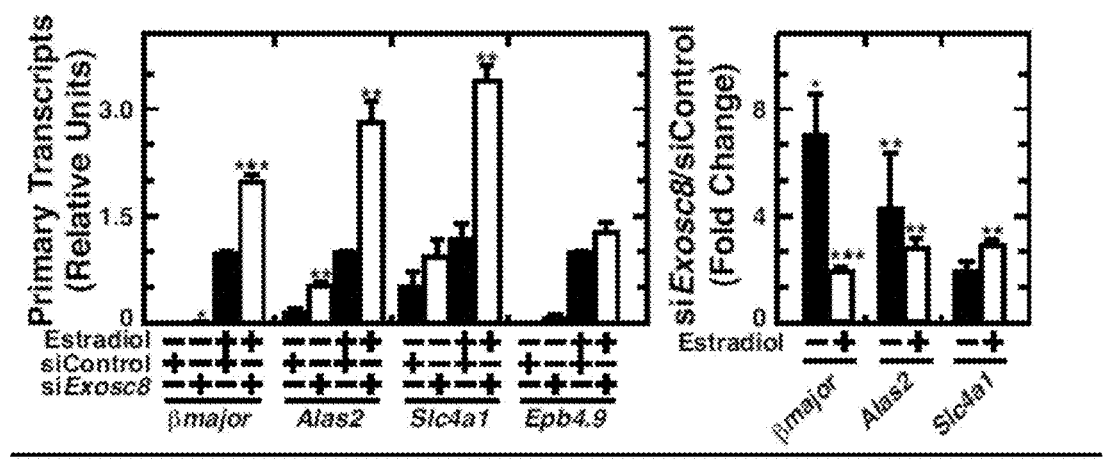
FIG. 14 shows quantitative real-time RT-PCR analysis of primary transcripts in control versus Exosc8 knockdown G1E-ER-GATA-1 cells (mean+/−SE; 3 independent experiments). Values were normalized to 18S rRNA expression and the expression is shown relative to estradiol treated control siRNA. Fold changes are also depicted upon Exosc8 knockdown relative to control (right). *, p<0.05; , p<0.01; *, p<0.001.

In principle, impairing the mRNA degradation function of the exosome complex by disturbing a core subunit could lead to the accumulation of mRNAs. To determine whether the gene expression alterations upon Exosc8 downregulation resulted solely from altered mRNA degradation, primary unprocessed transcripts were quantitated for Exosc8-responsive, GATA-1-activated genes, using the Exosc8-unresponsive gene Epb4.9 as a control. Similar to the mRNA analysis, βmajor, Alas2, and Slc4a1 primary transcripts increased 2 to 7-fold, while Epb4.9 primary transcripts were largely insensitive (FIG. 14) Additionally the expression of the gene encoding the large subunit of RNA polymerase II (RPII215) and an autophagy gene that is not GATA-1-regulated, Atg16l1 was measured. RPII215 and Atg16l1 expression levels were unaffected (data not shown). Thus, Exosc8 suppression of a select cohort of erythroid mRNAs does not involve an exclusive mRNA degradation mechanism.

Example 5

The Exosome Complex as an Endogenous Suppressor of Autophagy

Figure 15:
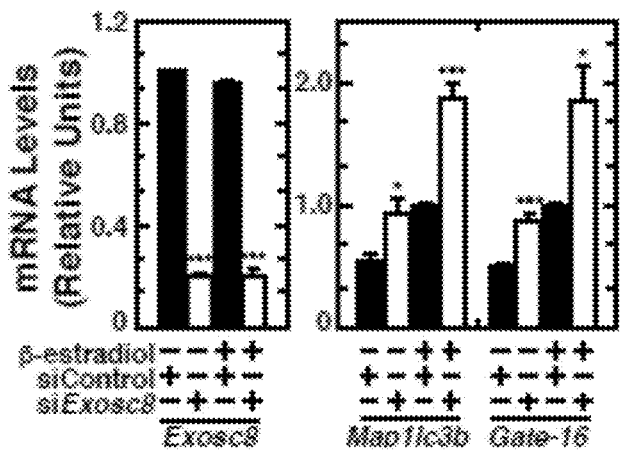
FIG. 15 shows a real-time RT-PCR analysis of Exosc8 and GATA-1-regulated autophagy gene mRNA levels in control versus Exosc8 knockdown G1E-ER-GATA-1 cells (mean+/−SE; 3 independent experiments). Values were normalized to 18S rRNA expression.
Figure 16:
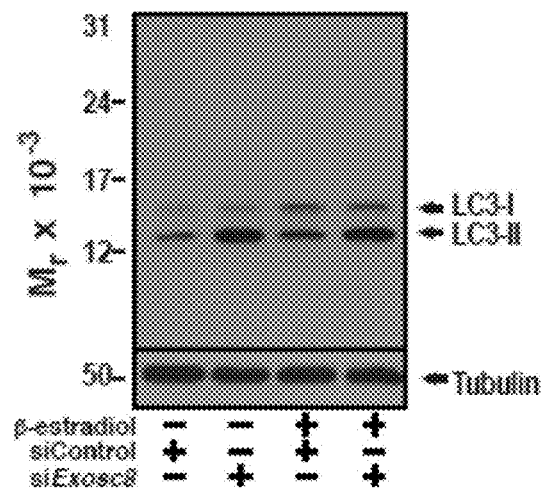
FIG. 16 shows semi-quantitative Western blot analysis of LC3B in Exosc8 knockdown G1E-ER-GATA-1 cells. A representative image is shown from 3 independent experiments.

Since autophagy genes are GATA-1/Foxo3-activated and mediate an important aspect of erythroid maturation, it was hypothesized that GATA-1/Foxo3-repressed genes may also be essential for the maturation program. Knocking-down Exosc8 by approximately 80% significantly upregulated Map1lc3b and Gate-16 expression approximately 2-fold (FIG. 15) and upregulated the active, lipid-conjugated form of LC3B (LC3-II), even without GATA-1 activity (FIG. 16).

Figure 17:
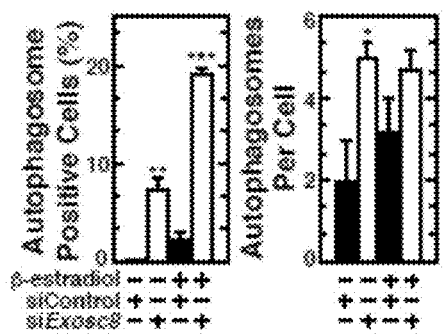
FIG. 17 shows quantitation of cells containing LC3B-positive autophagosomes (left) and the number of autophagosomes per cell (right) (mean+/−SE; 3 independent experiments).

Since LC3-II is a hallmark of autophagy, it was tested whether knocking-down Exosc8 induces autophagosome accumulation. Consistent with the LC3B upregulation detected by Western blotting, immunofluorescence analysis indicated that knocking-down Exosc8 significantly induced autophagosome accumulation in cells lacking or containing active GATA-1 (data not shown and FIG. 17). The number of autophagosomes per cell was higher in Exosc8-knockdown cells lacking GATA-1 activity (FIG. 17). As the Exosc8 knockdown induced autophagy, these results suggest that GATA-1-dependent Exosc8 repression in a physiological context instigates and/or enhances autophagy during erythroid cell maturation.

Example 6

Exosome Complex Structure and Expression During Primary Erythroblast Maturation

Figure 18:
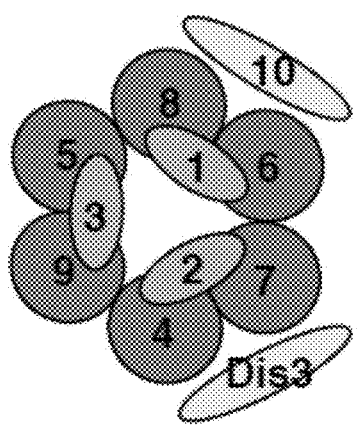
FIG. 18 is a schematic diagram of the exosome complex.

The exosome complex consists of 9 core subunits (Exosc1-9). Exosc1 (Csl4), Exosc2 (Rrp4) and Exosc3 (Rrp40) are RNA binding proteins. Biochemical analyses demonstrate that Exosc4/Exosc9 (Rrp41/Rrp45), Exosc6/Exosc7 (Mtr3/Rrp42) and yeast, but not human, Exosc5/Exosc8 (Rrp46/Rrp43) form stable dimers. Human EXOSC6/EXOSC7/EXOSC8 form a stable trimer (FIG. 18). Exosc1 interacts with Exosc6, Exosc2 interacts with both Exosc4 and Exosc7, and Exosc3 interacts with both Exosc5 and Exosc9. Thus, the RNA binding proteins stabilize subunit interactions within the complex (FIG. 18). Three catalytic subunits, Exosc10 (Rrp6), Dis3 (Rrp44) and Dis3l (a human homologue of yeast Dis3, not found in yeast) can bind to the core exosome. Exosc10 and Dis3l are 3' to 5' exoribonucleases, while Dis3 exhibits both endoribonuclease and exoribonuclease activity. Dis3 is mainly associated with the nuclear exosome complex and is involved in the degradation of rRNA and PROMTs (promoter upstream transcripts). Dis3l localizes in the cytoplasm where it mediates selective mRNA degradation. Exosc10 increases the stability of the exosome complex and interacts directly with Exosc1, Exosc6, and Exosc8 (FIG. 18). Exosc10 improves the ability of the exosome complex to process substrates using the long RNA-binding pathway by positioning Exosc1 correctly to bind RNA. Exosc10 localizes predominantly in the nucleus and is highly enriched in the nucleolus, indicating a role in pre-rRNA processing, although a small percentage is cytoplasmic. Dis3 or Dis3l binds to the exosome core opposite of Exosc10. The Dis3 (or Dis3l) N-terminus wedges between Exosc4 and Exosc7 and approaches the Exosc2 N-terminus (FIG. 18).

Figure 19:
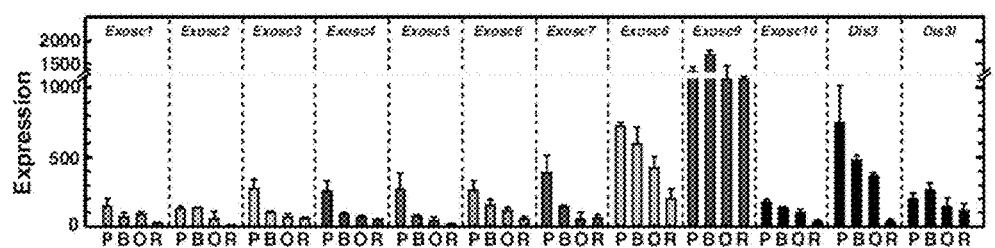
FIG. 19 shows an expression profile of mRNA levels for exosome complex components in primary mouse bone marrow erythroblasts during distinct maturation stages mined from the Erythron DB. P, proerythroblast; B, basophilic erythroblast; O, orthochromatic erythroblast; R, reticulocyte.
Figure 20:
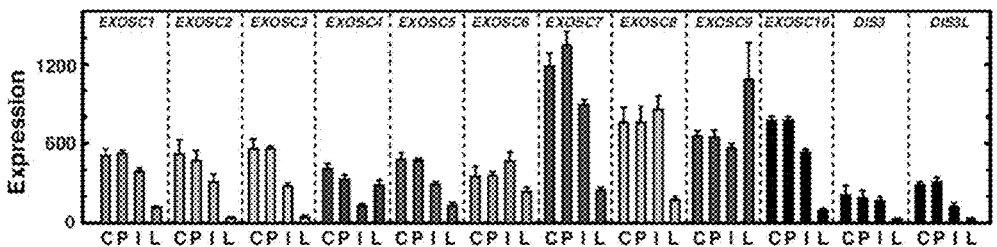
FIG. 20 shows an expression profile of mRNAs encoding exosome complex components during primary human erythroid differentiation mined from the Human Erythroblast Maturation (HEM) Database. C, Colony-Forming Unit-Erythroid (CFU-E); P, proerythroblast; I, intermediate-stage erythroblast; L, late-stage erythroblast.

To assess whether Exosc8 expression in G1E-ER-GATA-1 cells reflects its behavior upon primary erythroblast maturation, genomic databases were mined and the expression pattern of the exosome components in primary erythroblasts were determined. During definitive erythropoiesis in the mouse (FIG. 19) and human (FIG. 20), expression of exosome complex components, including Exosc8, decreased. The direct repression of Exosc8 by GATA-1/Foxo3, and Exosc8 repression upon murine and human erythroid cell maturation suggest important functional implications of the exosome complex in erythroid cell biology.

Example 7

Exosc8 Suppresses Primary Erythroblast Maturation

Figure 21:
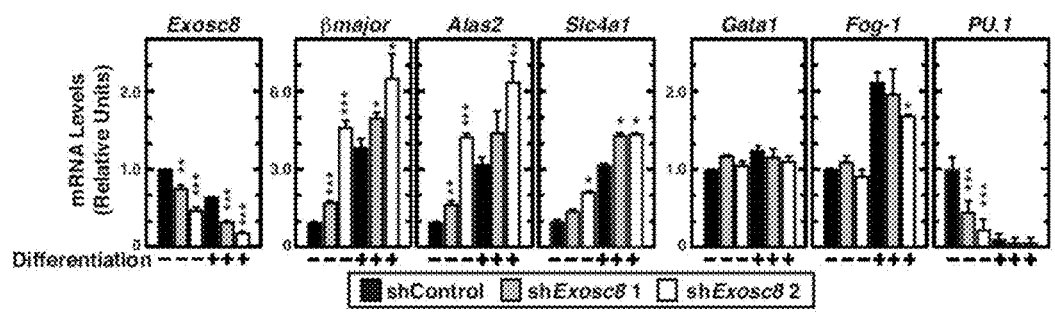
FIG. 21 shows quantitative real-time RT-PCR analysis of Exosc8 and selected GATA-1 target gene mRNA levels in control versus Exosc8 knockdown primary murine erythroid precursor cells cultured under expansion (−) or differentiation conditions (+) (mean+/−SE; 3 independent experiments). Values were normalized to 18S rRNA expression and the expression is shown relative to control shRNA under expansion conditions.

It was further tested whether Exosc8 suppresses a cohort of erythroid-specific RNAs in primary murine erythroid precursor cells isolated from embryonic day 14.5 fetal livers. Freshly isolated cells were infected with two distinct Exosc8 shRNA-expressing retroviruses, expanded for 3 days, and differentiated for 1 day. shRNA targeting luciferase was used as a control. The two Exosc8 shRNAs induced qualitatively similar results. Consistent with the G1E-ER-GATA-1 cell results, Exosc8 shRNA upregulated βmajor, Alas2, and Slc4a1 expression, while GATA-1 and Fog-1 expression were largely unaffected during expansion culture conditions (FIG. 21). The expression of the transcription factor PU.1, which can oppose GATA-1 activity in certain contexts, was significantly decreased in the Exosc8-knockdown cells under expansion conditions (FIG. 21). These data suggest that GATA-1-mediated repression of Exosc8 during erythropoiesis contributes to activation of GATA-1 target genes important for erythroid maturation.

Figure 22:
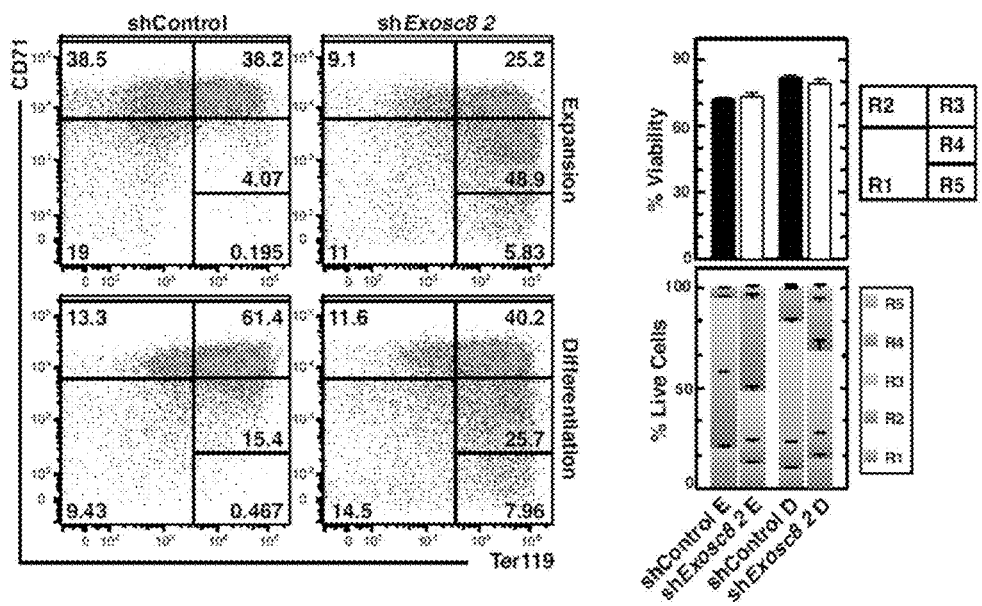
FIG. 22 shows flow cytometric quantitation of erythroid developmental stage by CD71 and Ter119 staining upon Exosc8 knockdown in primary erythroid precursor cells. Representative flow cytometry data, with the R1-R5 gates denoted, is shown from 3 independent experiments. The percentage of live cells from each condition and the cell populations in R1-R5 stages are from 3 independent experiments (mean+/−SE). E, Expansion; D, Differentiation.
Figure 23:
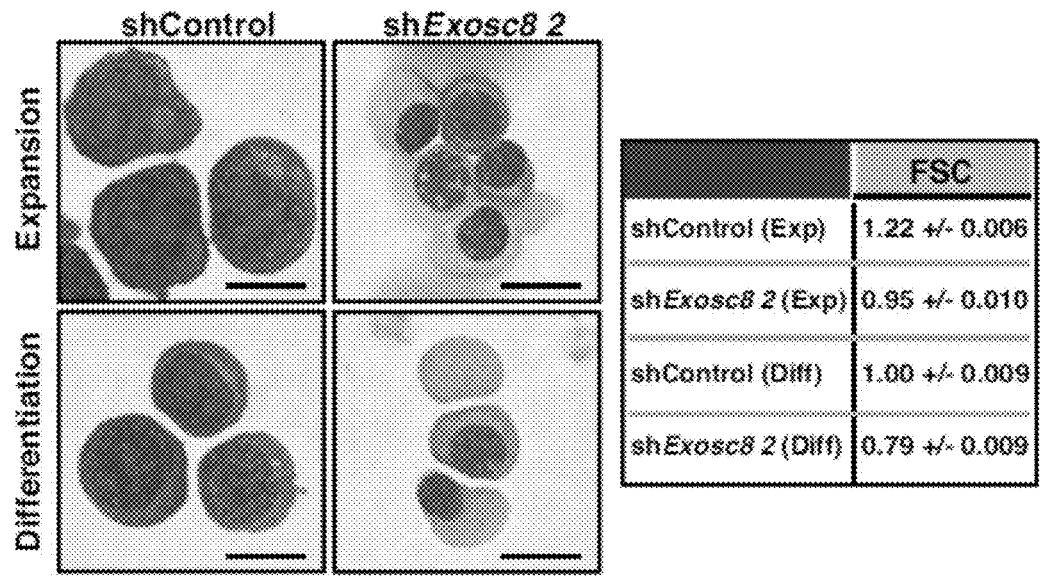
FIG. 23 shows representative images of Wright-Giemsa staining in control versus Exosc8 shRNA infected primary erythroid precursor cells cultured in expansion or differentiation media (Scale bar, 10 μm) and quantitation of cell size by flow cytometry.

Consistent with the upregulation of erythroid-specific genes, Exosc8 knockdown cells were considerably smaller and red, indicating hemoglobinization, versus control cells, even when differentiation was not induced. The maturation status of control and Exosc8-knockdown cells were assessed using flow cytometric quantitation of erythroid surface markers Ter119 and CD71 and Wright-Giemsa staining. Based on CD71 and Ter119 expression during expansion culture conditions, most cells represented R2 (proerythroblasts and early basophilic erythroblasts) and R3 (early and late basophilic erythroblasts) populations in the control (FIG. 22). The Exosc8 knockdown induced a major shift from R2 to R3 and R4 (polychromatophilic and orthochromatic erythroblasts) and even to R5 (late orthochromatic erythroblasts and reticulocytes) populations, without influencing cell viability, in every condition tested (FIG. 22). Consistent with enhanced erythroid maturation, the Exosc8-knockdown cells exhibited hallmark morphological features of mature erythroblasts and reticulocytes. The knockdown induced accumulation of cells with more condensed nuclei, and the cytoplasmic color became slate blue indicating hemoglobinization (FIG. 23). Forward scatter (FSC) measurements confirmed that the Exosc8-knockdown cells were significantly smaller than control cells (FIG. 23).

Figure 24:
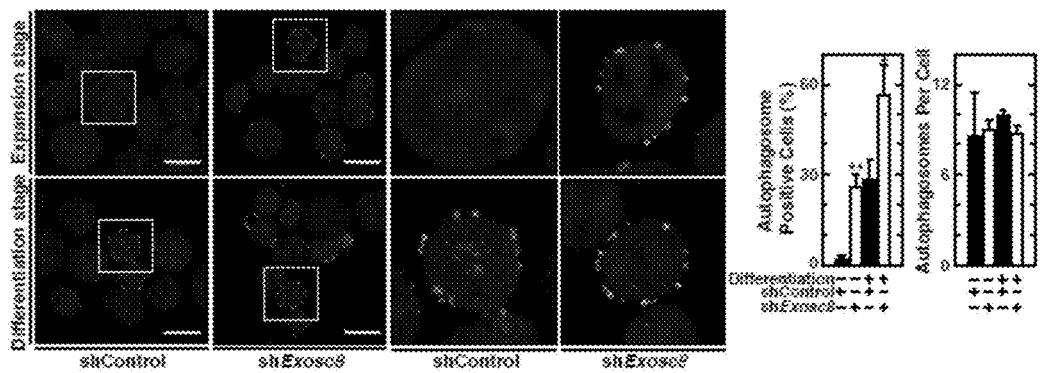
FIG. 24 shows representative images of LC3B punctae after Exosc8 knockdown in primary erythroid precursor cells under expansion and differentiation culture conditions. LC3B-positive autophagosomes (left) containing cells where quantified and the number of autophagosomes per cell (right) (mean+/−SE; 3 independent experiments).

Similar to G1E-ER-GATA-1 cells, knocking-down Exosc8 increased autophagosome-positive erythroid precursor cells 13 fold in the expansion stage and 2 fold upon differentiation (FIG. 24). The number of autophagosomes per positive cell was similar in all conditions (FIG. 24). Thus, Exosc8 suppresses autophagy in primary erythroid precursor cells.

Figure 25:
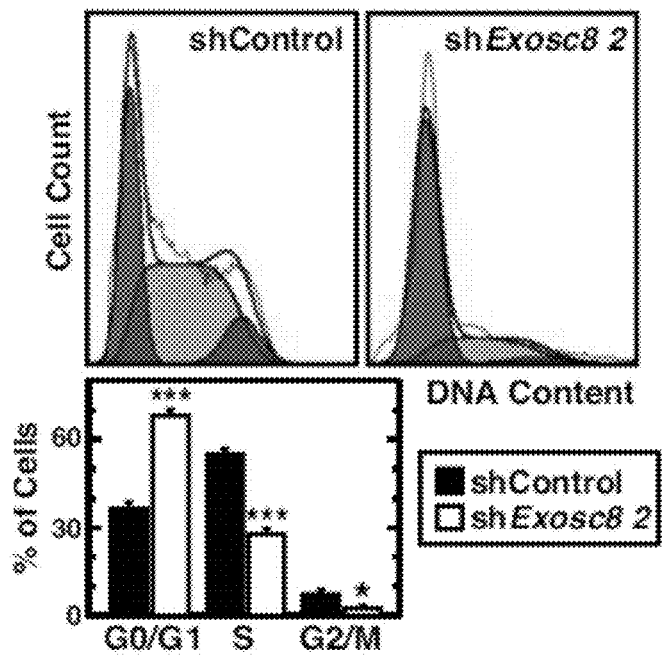
FIG. 25 shows flow cytometric cell cycle analysis of primary erythroid precursor cells infected with retrovirus expressing control or Exosc8 2 shRNA. Representative cell cycle profile is shown from 3 independent experiments. The percentage of the cell population in each cell cycle stage is from 3 independent experiments (mean+/−SE). Blue, S phase; Red, $G_0/G_1$ or $G_2/M$ phase.

During expansion of the primary erythroblasts, it was observed that Exosc8-knockdown samples consistently contained fewer cells than the control samples, leading to the analysis of their cell cycle status. $G_0/G_1$ populations increased approximately 2-fold, while S and $G_2/M$ phase cells decreased approximately 2-fold, indicating that the Exosc8 knockdown induced cell cycle exit, consistent with expectations for erythroid cell maturation. (FIG. 25).

Figure 26:
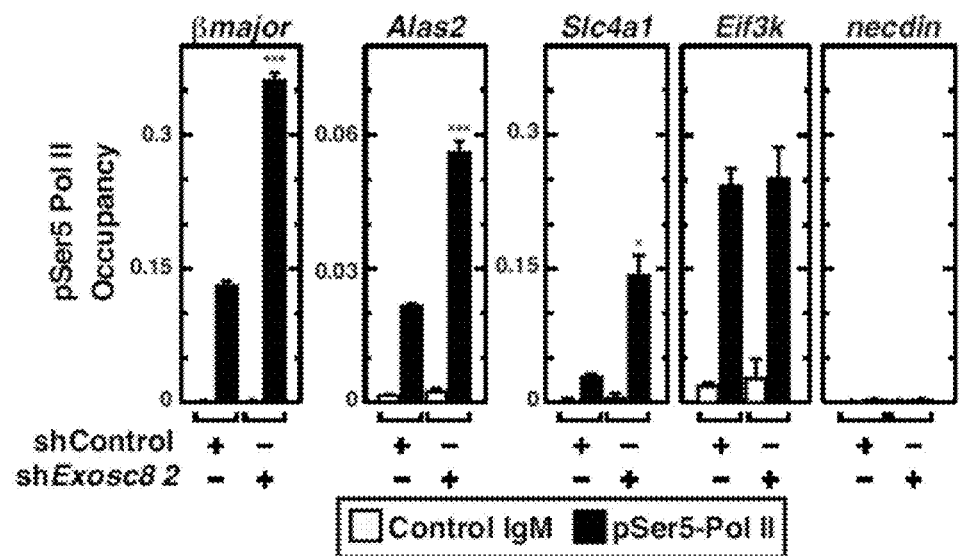
FIG. 26 shows quantitative ChIP analysis of serine 5-phosphorylated RNA Polymerase II occupancy at Exosc8-regulated GATA-1 target and control genes in control and Exosc8-knockdown primary murine erythroid precursor cells (mean+/−SE; 3 independent experiments). *, $p<0.05$; , $p<0.01$; *, $p<0.001$.

The Exosc8 knockdown would be expected to impair exosome complex activity to degrade certain mRNAs, thereby post-transcriptionally upregulating mRNAs. However, the Exosc8 knockdown also increased primary transcripts (FIGS. 14 and 15), suggesting a mechanism not restricted to cytoplasmic mRNA degradation. The possibility that elevated primary transcripts resulting from Exosc8 knockdown may reflect increased transcription of the respective genes was explored. In this regard, the exosome complex can function via epigenetic regulation and non-coding RNA surveillance, which impact transcription. It was tested whether Exosc8 regulates serine 5-phosphorylated RNA Polymerase II (pSer5-Pol II) occupancy at the affected promoters. Quantitative ChIP analysis in primary fetal liver erythroid progenitors revealed that the Exosc8 knockdown elevated pSer5-Pol II occupancy at βmajor, Alas2 and Slc4a1 promoters, but not at the active Eif3k promoter and the repressed Necdin promoter, indicating that Exosc8 represses transcription of these erythroid genes (FIG. 26). In aggregate, these data demonstrate that Exosc8 suppresses maturation of primary erythroid precursor cells.

Example 8

The Exosome Complex as an Endogenous Suppressor of Erythroid Cell Maturation

Figure 27:
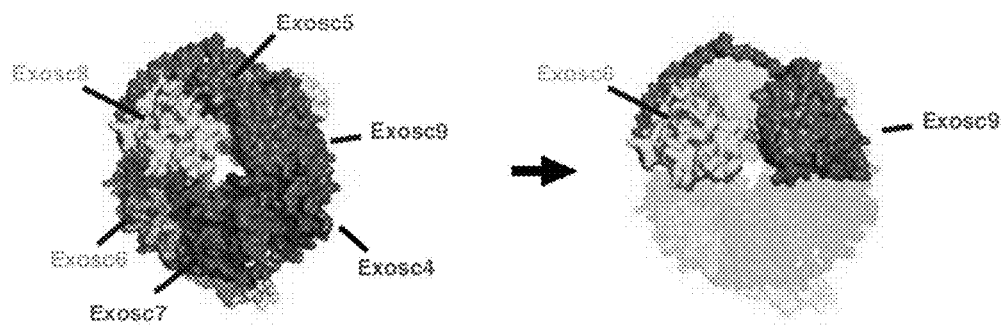
FIG. 27 shows the crystal structure of the human exosome complex demonstrating the interaction between Exosc8 and Exosc9.
Figure 28:
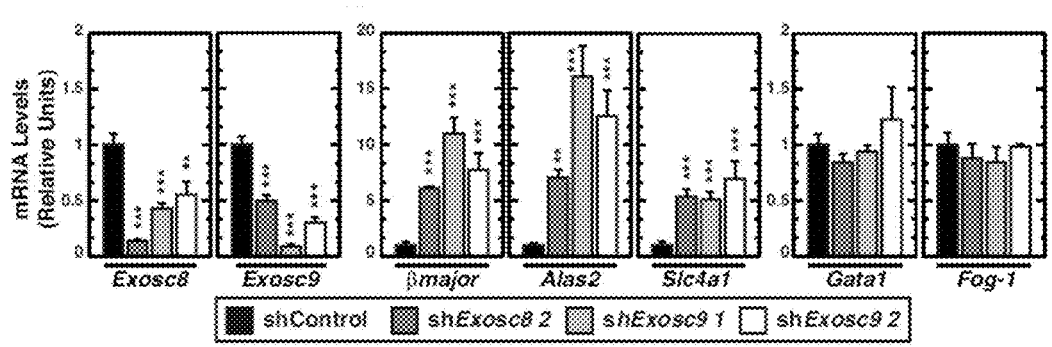
FIG. 28 shows quantitative real-time RT-PCR analysis of Exosc9 and selected GATA-1 target gene mRNA levels in control versus Exosc9 knockdown in expanding primary murine erythroid precursor cells (mean+/−SE; 4 independent experiments). Values were normalized to 18S rRNA level and the expression is shown relative to the control shRNA condition.
Figure 29:
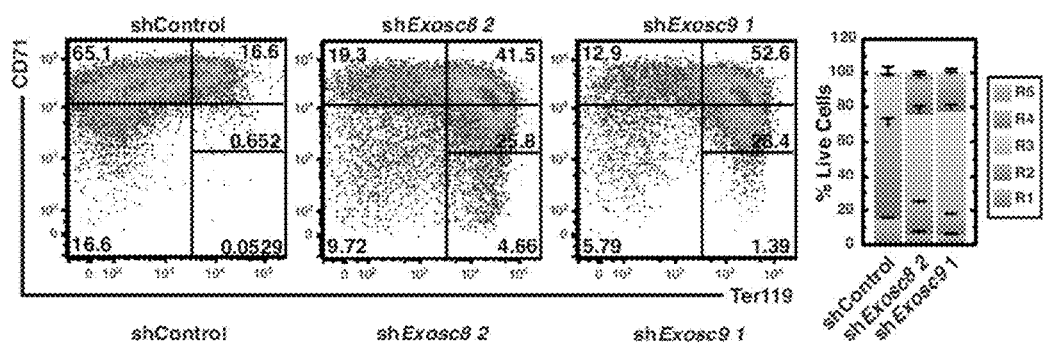
FIG. 29 shows flow cytometric quantitation of erythroid maturation stage by CD71 and Ter119 staining upon Exosc8 or Exosc9 knockdown in primary erythroid precursor cells. Representative flow cytometry data, with the R1-R5 gates denoted, is shown from 4 independent experiments. The percentage of the cell populations in R1-R5 stages are an average of 4 independent experiments.
Figure 30:
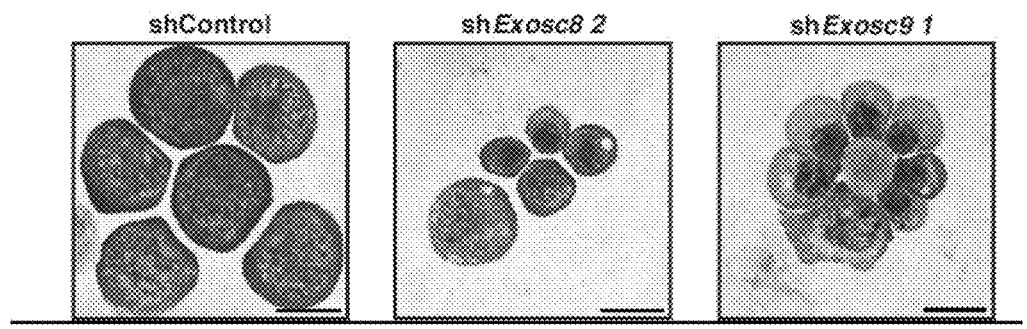
FIG. 30 shows representative images of Wright-Giemsa stained cells infected with control versus Exosc8 or Exosc9 shRNA-expressing virus. Cells were cultured under expansion conditions (Scale bar, 10 μm). *, $p<0.05$; , $p<0.01$; *, $p<0.001$.
Figure 31:
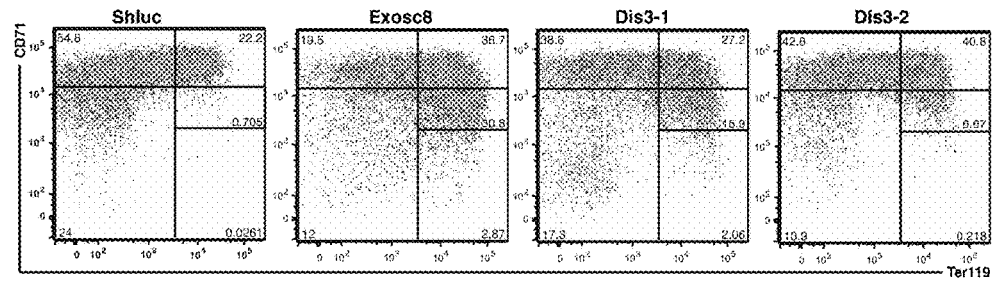
FIG. 31 shows flow cytometric quantitation of erythroid developmental stage by CD71 and Ter119 staining upon Exosc8 or Dis3 knockdown in primary erythroid precursor cells. Representative flow cytometry data, with the R1-R5 gates denoted, is shown from 3 independent experiments.
Figure 32:
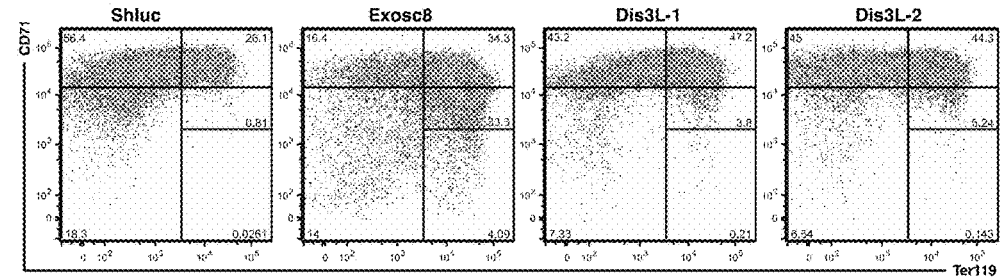
FIG. 32 shows flow cytometric quantitation of erythroid developmental stage by CD71 and Ter119 staining upon Exosc8 or Dis3L knockdown in primary erythroid precursor cells. Representative flow cytometry data, with the R1-R5 gates denoted, is shown from 3 independent experiments.

It was considered whether Exosc8 suppresses erythroid maturation by functioning within the exosome complex or independent of the exosome complex. To distinguish between these models, it was tested whether another exosome component, Exosc9, also suppresses erythroid maturation. Exosc9 was prioritized due to its integral position within the exosome complex, where it binds Exosc4 and interacts with Exosc8 via its C-terminal tail, which first interfaces with Exosc5 and then wraps around Exosc5 and Exosc8 (FIG. 27). Fetal liver-derived primary erythroid precursor cells were infected with two distinct Exosc9 shRNA-expressing retroviruses and the cells were expanded for 3 days and included Exosc8 shRNA as a positive control. Utilizing the GFP marker co-expressed with the shRNA, shRNA-expressing cells were sorted from the whole population. Recapitulating the results for Exosc8, reducing Exosc9 in primary erythroid precursor cells significantly increased the expression of βmajor, Alas2, and Slc4a1 without affecting GATA-1 and Fog-1 (FIG. 28). Similar to Exosc8 knockdown, immunophenotypical analysis using CD71 and Ter119 staining showed a major shift from R2 (proerythroblasts and early basophilic erythroblasts) to R3 (early and late basophilic erythroblasts) and R4 (polychromatophilic and orthochromatic erythroblasts) upon Exosc9 knockdown (FIG. 29). Wright-Giemsa staining demonstrated enhanced erythroid maturation in the Exosc9 knockdown cells (FIG. 30). To identify the role of the catalytic activity of the exosome in the Exosc8/Exosc9 mediated repression of erythroid maturation we knocked down two catalytic components of the exosome, Dis3 and Dis3L. Knockdown of both Dis3 (FIG. 31) and Dis3L (FIG. 32) reduced the number of cells in the R1 population and increased the R3, R4 and R5 cell populations, although to a lesser degree than either Exosc8 or Exosc9 knockdown. The ability of Exosc9, Dis3 and Dis3L knockdown to phenocopy the maturation effect resulting from the Exosc8 knockdown suggests that Exosc8 functions within the exosome complex, and/or select components of the complex, to suppress erythroid maturation.

Figure 33:
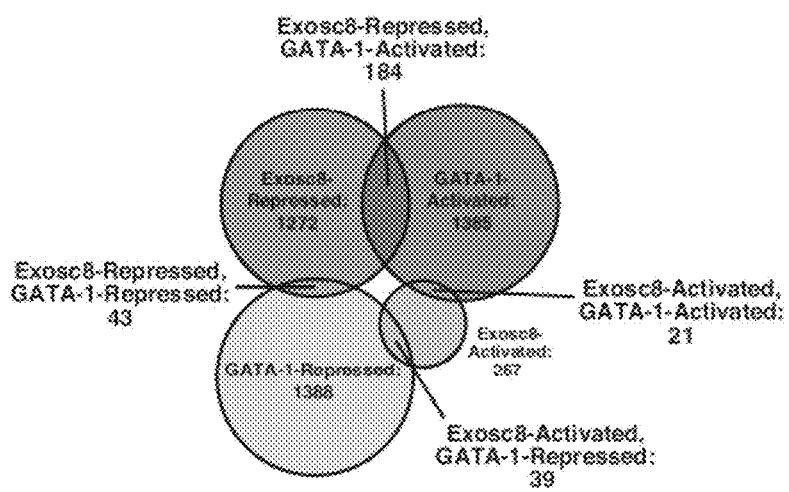
FIG. 33 shows the classification of GATA-1 and Exosc8 regulated genes based on activation or repression.
Figure 34:
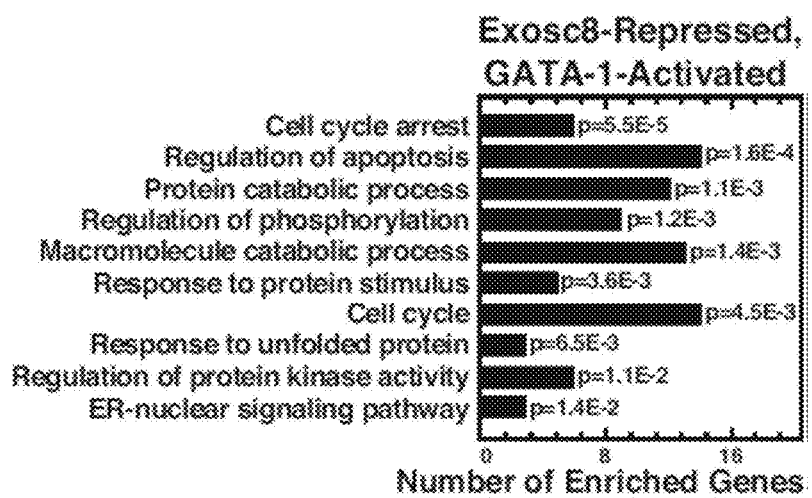
FIG. 34 shows a gene ontology analysis of GATA-1-activated, Exosc8-repressed genes. Redundant Gene Ontology categories were curated and removed.
Figure 35:
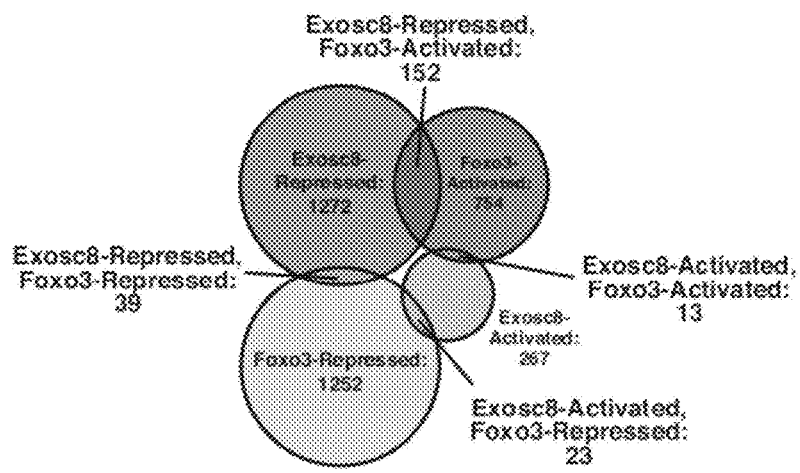
FIG. 35 shows classification of Foxo3 and Exosc8 regulated genes based on activation or repression.
Figure 36:
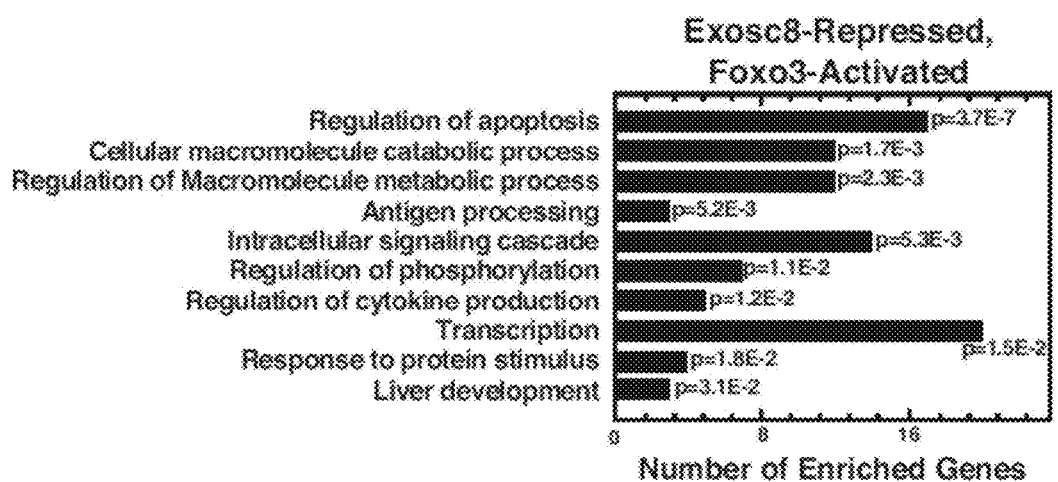
FIG. 36 shows a gene ontology analysis of Foxo3-activated, Exosc8-repressed genes. Redundant Gene Ontology categories were curated and removed.

To further dissect how downregulating Exosc8 promotes erythroid maturation, the transcriptomes of Exosc8-knockdown primary murine erythroid precursor cells and control cells were compared. The Exosc8-regulated genes were also compared to either GATA-1- or Foxo3-regulated genes. To interrogate the relationship between GATA-1- and Exosc8-regulated genes, GATA-1 and Excs8-regulated genes were classified as repressed or activated. The most frequent mode of co-regulation was Exosc8-repressed and GATA-1-activated (FIG. 33). The differentially regulated transcripts included those important for erythroid cell maturation, specifically heme biosynthesis (Alas2), anti-apoptosis (Bcl-xL), and the red cell cytoskeleton (Gypa). Gene ontology analysis was conducted to gain functional insights into the GATA-1-activated/Exosc8-repressed genes. The top three GO terms were cell cycle arrest, regulation of apoptosis, and cellular protein catabolic process (FIG. 34). Analysis of the Exosc8/Foxo3-regulated gene cohort revealed that like the GATA-1/Exosc8-regulated genes, the most frequent mode of regulation was Exosc8-repressed and Foxo3-activated (FIG. 35). Gene ontology analysis indicated that Exosc8- and Foxo3-regulate genes involved in apoptosis and macromolecular metabolism in maturing erythroid cells (FIG. 36).

Given that the Exosc8 knockdown caused cells to accumulate in $G_0/G_1$ phase, the GATA-1-activated, Exosc8-repressed genes involved in cell cycle arrest were further explored (FIG. 37). This category included Cdkn1b ($p27^{kip1}$), Ddit3 (CHOP), Gas2l1 (Gar22), Trp53inp1, Gadd45a, and Ern1 (FIG. 37). Cdkn1b controls the activity of cyclin-dependant kinases that bind to Cyclin D and Cyclin E, arresting cells in $G_1$. Ddit3 (CHOP) is a DNA damage-inducible $G_1/S$ transition inhibitor. Trp53inp1 functions downstream of p53 and p73 to induce $G_1$ arrest and to enhance apoptosis in multiple cell types. Ern1 is a component of the unfolded protein response, which is stimulated by unfolded proteins in the endoplasmic reticulum, leading to $G_1$ arrest. Gas2l1 (Gar22) is a downstream effector molecule of thyroid receptor and enhances Gata2 and c-Kit repression during erythroid maturation. Gas2l1 is highly expressed in cells arrested in $G_1$, and its overexpression in erythroid cells is associated with a lengthened cell cycle, especially S phase. Gadd45a responds to genotoxic stress by interacting with CDK1/Cyclin B1 to induce $G_2/M$ arrest; no specific role for Gadd45a in erythropoiesis has been reported (FIG. 37).

Figure 39:
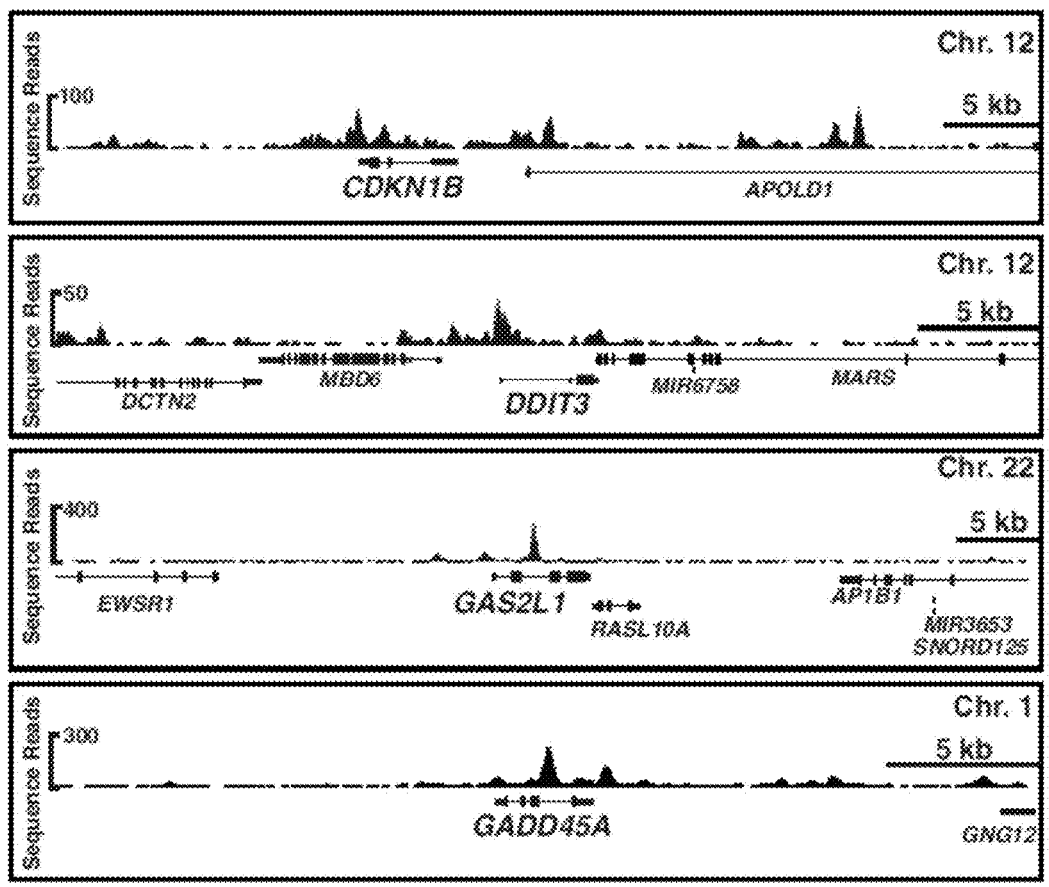
FIG. 39 shows ChIP-seq profiles of GATA-1 occupancy at cell cycle regulatory genes in primary human erythroblasts. All genes were orientated left to right. *, $p<0.05$; , $p<0.01$; *, $p<0.001$.

RT-PCR analysis confirmed that Exosc8 knockdown in primary murine erythroid precursor cells significantly elevated Cdkn1b, Ddit3, Gas2l1, Trp53inp1, and Gadd45a mRNAs, validating the array results. In addition, the Exosc9 knockdown significantly upregulated the same mRNAs, suggesting that the exosome complex suppresses these RNAs encoding cell cycle regulatory proteins (FIG. 38). In primary human erythroblasts, GATA-1 occupies intronic sites at CDKN1B, GAS2L1, and GADD45A and promoter regions of CDKN1B, DDIT3, GAS2L1, and GADD45A, suggesting direct GATA-1 regulation of these genes (FIG. 39). The Exosc8- and Exosc9-mediated suppression of genes mediating $G_1$ cell cycle arrest upon Exosc8 knockdown reveals insights regarding how exosome complex components control the erythroid cell cycle.

Figure 40:
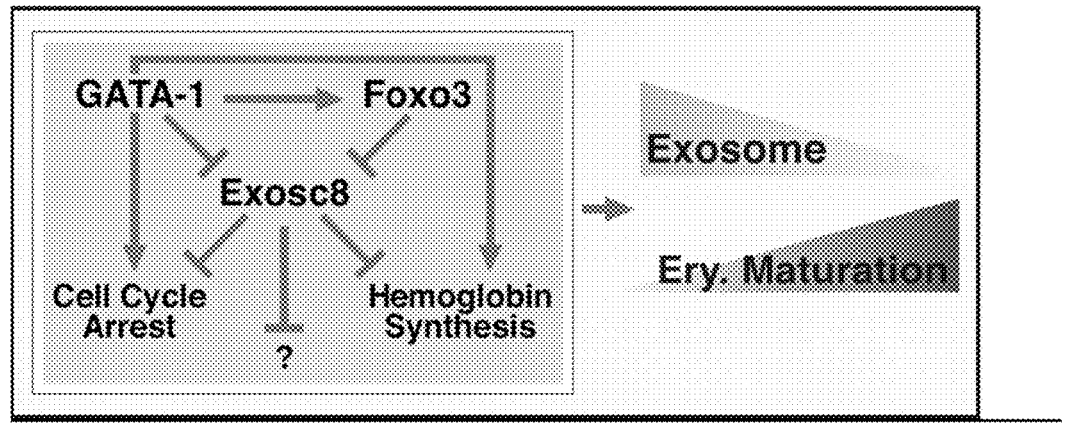
FIG. 40 is a schematic showing that GATA-1/Foxo3 overcome the exosome complex-dependent erythroid maturation barricade.

GATA-1 directly represses Exosc8 expression during maturation, thus indirectly upregulating Exosc8 targets. Given that GATA-1 also directly activates these Exosc8-repressed genes, this suggests that GATA-1/Foxo3 abrogates the Exosc8-mediated suppression, thus activating genes that promote erythroid maturation, including those involved in cell cycle arrest and hemoglobin synthesis (FIG. 40).

Example 9

Role of Additional Exosome Components to Control Autophagy

Figure 41:
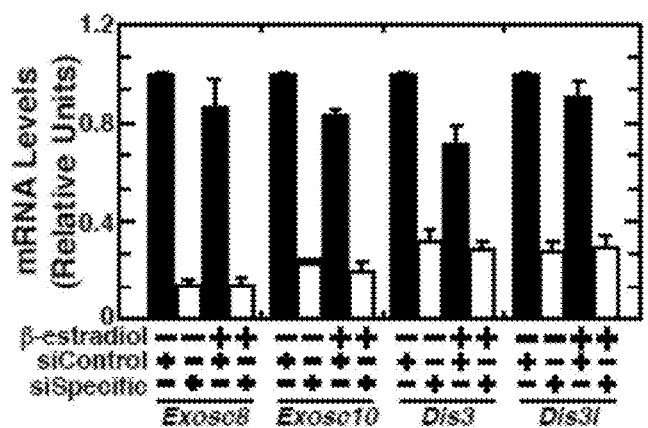
FIG. 41 shows a real-time RT-PCR analysis of Exosc8 and exosome complex catalytic subunits (Exosc10, Dis3, and Dis3l) mRNA levels in control versus exosome complex component knockdown G1E-ER-GATA-1 cells (mean+/−SE; 3 independent experiments).
Figure 42:
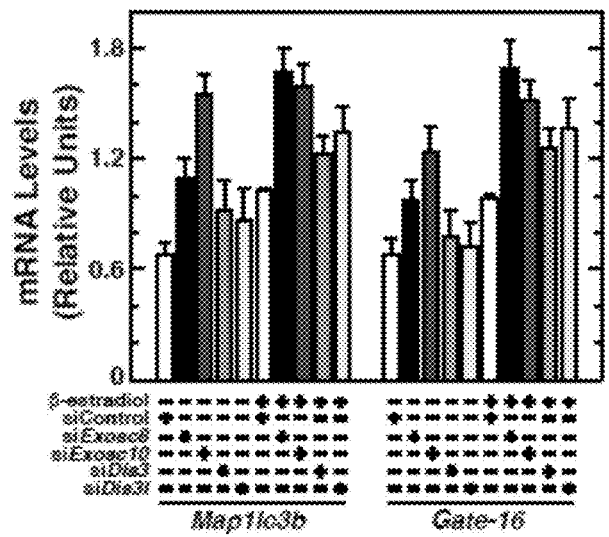
FIG. 42 shows representative GATA-1-regulated autophagy gene mRNA levels in control versus exosome complex component knockdown G1E-ER-GATA-1 cells (mean+/−SE; 3 independent experiments). Values were normalized to 18S rRNA expression.
Figure 43:
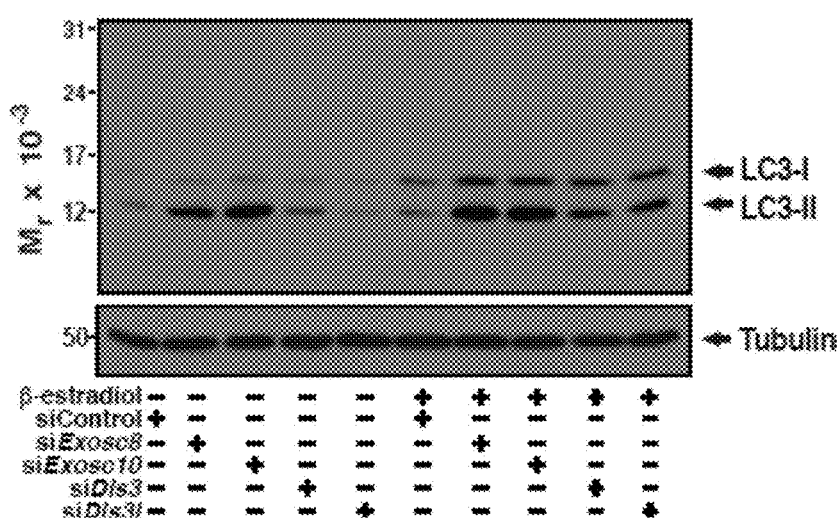
FIG. 43 shows semi-quantitative Western blot analysis of LC3B in exosome complex component knockdown G1E-ER-GATA-1 cells. A representative image is shown from 3 independent experiments.
Figure 44:
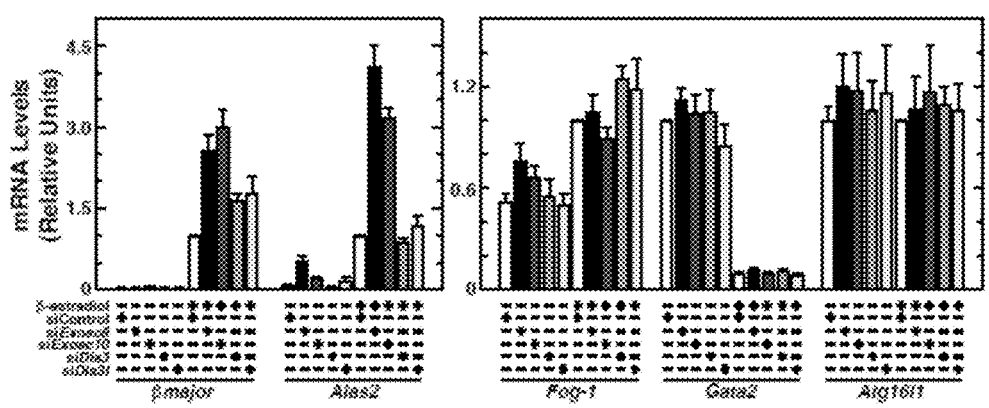
FIG. 44 shows real-time RT-PCR analysis of gene expression levels in control versus specific exosome complex component knockdown G1E-ER-GATA-1 cells (mean+/−SE; 3 independent experiments).

If Exosc8 functions through the exosome complex to control autophagy and erythroid gene expression, reducing the levels of additional exosome complex components should phenocopy the Exosc8 knockdown. Exosc10, Dis3, and Dis3l were knocked down (FIG. 41) and it was tested whether they resemble Exosc8 in regulating gene expression in G1E-ER-GATA-1 erythroid cells. The Exosc10 knockdown had a similar or quantitatively greater influence on autophagy gene expression versus the Exosc8 knockdown (FIG. 42). Resembling the RNA analysis, Western blotting also revealed significantly increased LC3-II upon Exosc8 or Exosc10 knockdown (FIG. 43), indicating increased autophagy. Knocking-down Exosc10 also increased βmajor and Alas2 expression without affecting Fog-1 or Gata2 expression (FIG. 44). Atg16l1, which is not GATA-1-regulated, was unaffected by the knockdown, analogous to the Exosc8 knockdown (FIG. 22). Reducing Dis3 or Dis3/levels either did not significantly alter the gene expression or slightly increased expression (FIGS. 42 and 44). The similar Exosc8 and Exosc10 activities implicate the exosome complex in selectively mediating gene expression changes and in inducing autophagy.

Discussion: Described herein is a novel genetic network regulated combinatorially by two proteins that control erythropoiesis, GATA-1 and Foxo3. In addition to GATA-1/Foxo3-activated autophagy genes, this network includes GATA-1/Foxo3-repression of Exosc8. Functional analyses established a mechanism in which GATA-1/Foxo3 pro-erythroid maturation activity is opposed by exosome complex components. By downregulating these components, GATA-1/Foxo3 overcome a barrier to erythroid cell maturation.

Knocking down Exosc8 or Exosc9 resulted in upregulation of genes encoding proteins that control multiple aspects of erythroid maturation. Morphological and flow cytometric analysis provided strong evidence that Exosc8/Exosc9 repress maturation of primary erythroid precursor cells. Exosc8/Exosc9 do not regulate GATA-1 and FOG-1 expression, excluding a potentially simple mechanism to alter GATA-1 target gene expression. Exosc8 does not exclusively function by suppressing erythroid cell mRNAs, as it also regulates primary transcripts and suppresses pSer5-Pol II occupancy at erythroid gene promoters. These results demonstrate that Exosc8 function in erythroid cells can regulate erythroid gene transcription. In Drosophila, exosome complex components colocalize with chromatin insulator factors at boundary elements and also localize to promoters. In yeast, the exosome complex localizes to nucleoli and subnuclear regions enriched in actively transcribed genes. The exosome complex can regulate gene expression through alternative transcription start site selection and may directly impact heterochromatin formation and gene silencing through post-transcriptional regulation.

GATA-1/Exosc8 co-regulate genes involved in cell cycle arrest, especially those that establish $G_1$ arrest. Cell cycle arrest in $G_1$ is one of the hallmarks of late-stage erythroblast differentiation. Enforced cell proliferation of late-stage bone marrow erythroblasts leads to decreased hemoglobin production, retention of mitochondria, and apoptosis. Cdkn1b ($p27^{kip1}$), which is GATA-1-activated and Exosc8-repressed, is a highly studied cell cycle arrest protein. Cdkn1b controls the levels and activity of cyclin-dependent kinases (CDK2, CDK4 and CDK6), which bind Cyclin D and Cyclin E, inducing $G_1$ arrest in multiple cell types. Cdkn1b appears to be important for erythroid maturation, as it is induced by GATA-1 and accumulates during terminal maturation of erythroblasts. Furthermore, ectopic expression of Cdkn1b promotes erythroid maturation of K562 erythroleukemia cells. Although the other GATA-1-activated, Exosc8-repressed $G_1$ arrest genes had not been linked to erythropoiesis, based on their established functions in other systems, we predict that these genes contribute to $G_1$ arrest during erythroid maturation.

GATA-1 directly upregulates Foxo3 expression and then functions in combination with Foxo3 to repress Exosc8 expression. Exosc8, as a component of the exosome complex, establishes a blockade to erythroid maturation by suppressing GATA-1-activated genes that contribute to essential erythroid maturation processes including hemoglobin synthesis, cell cycle arrest, and other key processes. Reduced expression of the exosome complex components, either physiologically through GATA-1/Foxo3-mediated co-repression, or experimentally, eliminates this blockade, allowing thus facilitating erythroid maturation (FIG. 40).

Foxo3 and GATA-2 are important regulators of hematopoietic stem cells and neural stem/progenitor cells. Considering certain similarities between GATA-1 and GATA-2, it is attractive to propose that GATA-2 may also function with Foxo3 to establish genetic networks in distinct cell types. GATA factor-Foxo3 interactions may therefore have broader functional roles in the context of stem cell biology.

In summary, the discoveries of novel genetic networks and unexpected biological functions of exosome complex components described herein provide new mechanistic insights into the essential process of red blood cell development. Key nodal points in the respective mechanisms will be vulnerable to perturbations that cause and/or contribute to human red cell disorders, and this work establishes a new framework for controlling erythroid maturation.

As used herein, "nucleic acid" means single-, double-, or multiple-stranded DNA, RNA and derivatives thereof. In certain embodiments, the nucleic acid is single stranded. Modifications may include those that provide other chemical groups that incorporate additional charge, polarizability, hydrogen bonding, electrostatic interaction, and functionality to the nucleic acid. Such modifications include, but are not limited to, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping moieties. A 2' deoxy nucleic acid linker is a divalent nucleic acid of any appropriate length and/or internucleotide linkage wherein the nucleotides are 2' deoxy nucleotides.

Certain nucleic acid compounds can exist in unsolvated forms as well as solvated forms, including hydrated forms. In general, the solvated forms are equivalent to unsolvated forms. Certain nucleic acid compounds may exist in multiple crystalline or amorphous forms. In general, all physical forms are equivalent for the uses contemplated by the methods provided herein.

Certain nucleic acid compounds may possess asymmetric carbon atoms (optical centers) or double bonds; the racemates, diastereomers, geometric isomers and individual isomers.

In general, complementary nucleic acid strands hybridize under stringent conditions. The term "stringent hybridization conditions" or "stringent conditions" refers to conditions under which a nucleic acid hybridizes to an inhibitory nucleic acid, for example, to form a stable complex (e.g. a duplex), but to a minimal number of other sequences. The stability of complex is a function of salt concentration and temperature (See, for example, Sambrook et al., Molecular Cloning: A Laboratory Manual 2d Ed. (Cold Spring Harbor Laboratory, (1989); incorporated herein by reference). Stringency levels used to hybridize a nucleic acid to an inhibitory nucleic acid can be readily varied by those of skill in the art. The phrase "low stringency hybridization conditions" refers to conditions equivalent to hybridization in 10% formamide, 5 times Denhart's solution, 6 times SSPE, 0.2% SDS at 42° C., followed by washing in 1 times SSPE, 0.2% SDS, at 50° C. Denhart's solution and SSPE are well known to those of skill in the art as are other suitable hybridization buffers. (See, e.g., Sambrook et al.). The term "moderately stringent hybridization conditions" refers to conditions equivalent to hybridization in 50% formamide, 5 times Denhart's solution, 5 times SSPE, 0.2% SDS at 42° C., followed by washing in 0.2 times SSPE, 0.2% SDS, at 60° C. The term "highly stringent hybridization conditions" refers to conditions equivalent to hybridization in 50% formamide, 5 times Denhart's solution, 5 times SSPE, 0.2% SDS at 42° C., followed by washing in 0.2 times SSPE, 0.2% SDS, at 65° C.

"Complementary," as used herein, refers to the capacity for precise pairing of two nucleobases (e.g. A to T (or U) and G to C) regardless of where in the nucleic acid the two are located. For example, if a nucleobase at a certain position of nucleic acid is capable of hydrogen bonding with a nucleobases at a certain position of an inhibitory nucleic acid, then the position of hydrogen bonding between the nucleic acid and the inhibitory nucleic acid is considered to be a complementary position. The nucleic acid and inhibitory nucleic acid are "substantially complementary" to each other when a sufficient number of complementary positions in each molecule are occupied by nucleobases that can hydrogen bond with each other. Thus, the term "substantially complementary" is used to indicate a sufficient degree of precise pairing over a sufficient number of nucleobases such that stable and specific binding occurs between the nucleic acid and an inhibitory nucleic acid. The phrase "substantially complementary" thus means that there may be one or more mismatches between the nucleic acid and the inhibitory nucleic acid when they are aligned, provided that stable and specific binding occurs. The term "mismatch" refers to a site at which a nucleobases in the nucleic acid and a nucleobases in the inhibitory nucleic acid with which it is aligned are not complementary. The nucleic acid and inhibitory nucleic acid are "perfectly complementary" to each other when the nucleic acid is fully complementary to the inhibitory nucleic acid across the entire length of the nucleic acid.

Generally, a nucleic acid is "antisense" to an inhibitory nucleic acid when, written in the 5' to 3' direction, it comprises the reverse complement of the corresponding region of the target nucleic acid. "Antisense compounds" are also often defined in the art to comprise the further limitation of, once hybridized to a target, being able to modulate levels, expression or function of the target compound.

As used herein, "sequence identity" or "identity" refers to the nucleobases in two sequences that are the same when aligned for maximum correspondence over a specified comparison window. As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "pharmaceutically acceptable salts" is meant to include salts of the active compounds which are prepared with relatively nontoxic acids or bases, depending on the particular substituents found on the compounds described herein. When nucleic acid compounds contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When nucleic acid compounds contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Certain nucleic acid compounds contain both basic and acidic functionalities that allow the compounds to be converted into either base or acid addition salts.

The neutral forms of the nucleic acid compounds may be regenerated by contacting the salt with a base or acid and isolating the parent compound in the conventional manner. The parent form of the compound differs from the various salt forms in certain physical properties, such as solubility in polar solvents.

As used herein, "pharmaceutical composition" means therapeutically effective amounts of the compound together with a pharmaceutically acceptable excipient, such as diluents, preservatives, solubilizers, emulsifiers, and adjuvants. As used herein "pharmaceutically acceptable excipients" are well known to those skilled in the art.

Tablets and capsules for oral administration may be in unit dose form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

For topical application to the skin, the drug may be made up into a cream, lotion or ointment. Cream or ointment formulations which may be used for the drug are conventional formulations well known in the art. Topical administration includes transdermal formulations such as patches.

For topical application to the eye, the inhibitor may be made up into a solution or suspension in a suitable sterile aqueous or non-aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium, either subcutaneously, or intravenously, or intramuscularly, or intrasternally, or by infusion techniques, in the form of sterile injectable aqueous or oleaginous suspensions. Depending on the vehicle and concentration used, the drug can either be suspended or dissolved in the vehicle. Advantageously, adjuvants such as a local anaesthetic, preservative and buffering agents can be dissolved in the vehicle.

Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of enhancing erythropoiesis in an individual in need thereof, comprising administering an effective amount of an agent that decreases the expression of Exosc8, wherein the agent produces an increase in red blood cell production in the individual, and wherein the agent is an inhibitory nucleic acid molecule that selectively decreases the expression of Exosc8.

2. The method of claim 1, wherein the individual is a human in need of treatment for an anemic disorder, hemophilia, thalassemia, sickle cell disease, bone marrow transplantation, hematopoietic stem cell transplantation, thrombocytopenia, pancytopenia, or hypoxia.

3. The method of claim 2, wherein the anemic disorder is associated with aging, infectious disease, chronic renal failure, end-stage renal disease, renal transplantation, cancer, AIDS, antiviral therapy, chronic stress, chemotherapy, radiation therapy, bone marrow transplantation, nutritional iron deficiency, blood-loss, hemolysis, or is of genetic origin.

4. The method of claim 3, wherein the individual has a reduced hematocrit.

5. The method of claim 1, wherein the inhibitory nucleic acid molecule is a small interfering RNA, an antisense RNA, a ribozyme, or a triple helix nucleic acid.

6. The method of claim 5, wherein the small interfering RNA is an siRNA or an shRNA.

7. The method of claim 6, wherein the small interfering RNA comprises 19 to 29 nucleotides that are substantially complementary to a sequence of 19 to 29 nucleotides of Exosc8.

8. The method of claim 7, wherein the small interfering RNA comprises 19 to 29 nucleotides that are substantially complementary to a sequence of 19 to 29 nucleotides in the region of nucleotides 363 to 405 of SEQ ID NO. 9, nucleotides 1129-1150 of SEQ ID NO. 9, nucleotides 712-730 of SEQ ID NO. 9, nucleotides 451 to 469 of SEQ ID NO. 9, nucleotides 501 to 519 of SEQ ID NO. 9, or the corresponding regions of SEQ ID NO. 1.

9. The method of claim 8, wherein the small interfering RNA is an siRNA having SEQ ID NO. 16, 17, 18, 19, the corresponding sequence of SEQ ID NO. 1, or a combination thereof.

10. The method of claim 8, wherein the small interfering RNA is an shRNA having SEQ ID NO. 20, 21, 22, the corresponding sequence of SEQ ID NO. 1, or a combination thereof.

* * * * *